(12) United States Patent
Jovanov

(10) Patent No.: US 12,343,164 B1
(45) Date of Patent: Jul. 1, 2025

(54) SYSTEMS AND METHODS FOR MONITORING PHYSIOLOGICAL PARAMETERS WITH CAPACITIVE SENSING

(71) Applicant: Board of Trustees of the University of Alabama, for and on behalf of the University of Alabama in Huntsville, Huntsville, AL (US)

(72) Inventor: Emil Jovanov, Huntsville, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 0 days.

(21) Appl. No.: 18/182,193

(22) Filed: Mar. 10, 2023

Related U.S. Application Data

(63) Continuation of application No. 16/174,163, filed on Oct. 29, 2018, now Pat. No. 11,622,717, which is a
(Continued)

(51) Int. Cl.
*A61B 5/00* (2006.01)
*A61B 5/024* (2006.01)
*G06F 3/044* (2006.01)

(52) U.S. Cl.
CPC .......... *A61B 5/6801* (2013.01); *A61B 5/0024* (2013.01); *A61B 5/02405* (2013.01); *A61B 5/7445* (2013.01); *G06F 3/044* (2013.01)

(58) Field of Classification Search
CPC ... A61B 5/0537; A61B 5/6801; A61B 5/0024; A61B 5/02405
See application file for complete search history.

(56) References Cited

U.S. PATENT DOCUMENTS

| | | |
|---|---|---|
| 3,391,547 A | 7/1968 | Kingston |
| 4,343,316 A | 8/1982 | Jespersen |
| (Continued) | | |

FOREIGN PATENT DOCUMENTS

| | | |
|---|---|---|
| CN | 205054984 U | 3/2016 |
| EP | 3000385 A1 | 3/2016 |
| (Continued) | | |

OTHER PUBLICATIONS

Jovanov, et al., "Guest Editoral Body Sensor Networks: From Theory to Emerging Applications," IEEE Transactions on Information Technology in Biomedicine, Nov. 2009, pp. 859-863, vol. 13, No. 6.
(Continued)

*Primary Examiner* — Curtis B Odom
(74) *Attorney, Agent, or Firm* — Jon E. Holland; Butler Snow LLP

(57) ABSTRACT

A smart object may be used to monitor physiological parameters of a user. The object has at least one capacitive sensor to sense a change in capacitance when a tissue of the user comes into contact with the at least one capacitive sensor. The change in capacitance can be used to detect physiological parameters of a user such as heart rate, inter-beat interval and respiratory rate. The smart object may also be used with another smart object to determine the identity of the user or other physiological parameters of the user such as blood pressure.

27 Claims, 35 Drawing Sheets

Related U.S. Application Data continuation-in-part of application No. 15/239,810, filed on Aug. 17, 2016, now Pat. No. 10,433,666.

(60) Provisional application No. 62/578,209, filed on Oct. 27, 2017, provisional application No. 62/205,839, filed on Aug. 17, 2015, provisional application No. 62/241,494, filed on Oct. 14, 2015, provisional application No. 62/330,692, filed on May 2, 2016.

(56) References Cited

U.S. PATENT DOCUMENTS

| | | | |
|---|---|---|---|
| 5,135,485 | A | 8/1992 | Cohen et al. |
| 5,182,545 | A | 1/1993 | Goekler et al. |
| 7,928,835 | B1 | 4/2011 | Jovanov et al. |
| 8,574,165 | B2 | 11/2013 | Marsh |
| 8,754,769 | B2 | 6/2014 | Stein et al. |
| 8,863,649 | B1 | 10/2014 | Rao et al. |
| 9,125,798 | B2 | 9/2015 | Stein et al. |
| 9,358,183 | B2 | 6/2016 | Stein et al. |
| 10,433,666 | B1 | 10/2019 | Jovanov |
| 11,622,717 | B1 | 4/2023 | Jovanov |
| 11,678,812 | B1 | 6/2023 | Jovanov |
| 2004/0215521 | A1 | 10/2004 | Crisp, III |
| 2005/0215915 | A1* | 9/2005 | Noda ............ A61B 5/113 600/500 |
| 2008/0039700 | A1* | 2/2008 | Drinan ........... A61B 5/6887 600/301 |
| 2011/0224529 | A1* | 9/2011 | Lading ........... A61B 5/021 600/382 |
| 2013/0066168 | A1* | 3/2013 | Yang ............. G01L 1/146 600/301 |
| 2013/0211208 | A1 | 8/2013 | Varadon et al. |
| 2014/0221849 | A1 | 8/2014 | Farringdon |
| 2015/0282768 | A1* | 10/2015 | Luna ............. A61B 5/0205 600/386 |
| 2016/0007935 | A1* | 1/2016 | Hernandez ....... A61B 5/024 600/595 |
| 2016/0018274 | A1* | 1/2016 | Seitz ............ A61B 5/6843 73/862.626 |
| 2016/0220184 | A1 | 8/2016 | Manion |
| 2018/0055455 | A1 | 3/2018 | Hu |

FOREIGN PATENT DOCUMENTS

| | | |
|---|---|---|
| WO | 2007057014 A1 | 5/2007 |
| WO | 2013186688 A1 | 12/2013 |

OTHER PUBLICATIONS

Brüser, et al., "Ambient and Unobtrusive Cardiorespiratory Monitoring Techniques," IEEE Reviews in Biomedical Engineering, Jan. 2014, 18 pages.

Jovanov, et al., "SmartStuff: A Case Study of a Smart Water Bottle," 38th Annual International of the IEEE Engineering in Medicine and Biology Society, Aug. 2016, 4 pages.

Marasco, et al., "A Survey on Anti-Spoofing Schemes for Fingerprint Recognition Systems," ACM Computing Surveys, Sep. 2014, 36 pages, vol. 47, No. 2, Article A.

Ding, et al., "A Comprehensive Survey on Pose-Invariant Face Recognition," ACM Transactions on Intelligent Systems and Technology, Mar. 2016, 40 pages, vol. 7, Issue 3.

Jovanov, et al., "Design and Feasibility of a Safe Pill Bottle," Applied System Innovation, 2018, 11 pages, vol. 1.

Talukder, et al., "A New Method to Prevent Unintentional Child Poisoning," 40th Annual International Conference of the IEEE Engineering in Medicine and Biology Society, Jul. 2018, 4 pages.

Brotfain, et al., "Urine Flow Rate Monitoring in Hypovolemic Multiple Trauma Patients," World Journal of Emergency Surgery, 2017, 6 pages.

Garrett, et al., "Engineering Approaches to Assessing Hydration Status," IEEE Reviews in Biomedical Engineering, 2018, pp. 233-248, vol. 11.

Majumder, et al., "Noncontact Wearable Wireless ECG Systems for Long-Term Monitoring," IEEE Reviews in Biomedical Engineering, 2018, pp. 306-321, vol. 11.

Hersch, et al., "Accuracy and Ease of Use of a Novel Electronic Urine Output Monitoring Device Compared with Standard Manual Urinometer in the Intensive Care Unit," Journal of Critical Care, 2009, pp. 629.e13-629.e17, vol. 24.

Deurenberg, et al., "Multi-Frequency Impedance for the Prediction of Extracellular Water and Total Body Water," British Journal of Nutrition, 1995, pp. 349-358, vol. 73.

Armstrong, "Assessing Hydration Status: The Elusive Gold Standard," Journal of the American College of Nutrition, 2007, pp. 575S-584S, vol. 26, No. 5.

"Acute Kidney Injury (AKI)," National Kidney Foundation, https://kidney.org/atoz/content/AcuteKidneyInjury, pp. 1-3.

Premanode, et al., "A Novel, Low Power Biosensor for Real Time Monitoring of Creatinine and Urea in Peritoneal Dialysis," NSTI-Nanotech, 2006, pp. 221-224, vol. 2.

Li, et al., "A Large-Scale Measurement of Dielectric Properties of Normal and Malignant Colorectal Tissues Obtained from Cancer Surgeries at Larmor Frequencies," Medical Physics Nov. 2016, pp. 5791-5597, vol. 43 No. 11.

Ezerskaia, et al., "Quantitative and Simultaneous Non-Invasive Measurement of Skin Hydration and Sebum Levels," Biomedical Optics Express, Jun. 2016, 10 pages, vol. 7, No. 6.

Jovanov, et al., U.S. Appl. No. 18/144,786, entitled, "Systems and Methods for Monitoring Hydration,", filed May 8, 2023.

Emil Jovanov, "Vital Sign Monitoring Using Capactitive Sensing," 40th Annual International Conference of the IEEE Engineering in Medicine and Biology Society, Jul. 2018, 4 pages.

Ramezani, "An Implementation of Embedded Software for Real Time Monitoring of Bioimpedance," The University of Alabama in Huntsville, Dec. 16, 2020, pp. 1-91.

Matthews, et al., "Enabling Complex Impedance Spectroscopy for Cardio-Respiratory Monitoring with Wearable Biosensors: A Case Study," Electochem, Aug. 2023, pp. 389-410, vol. 4.

\* cited by examiner

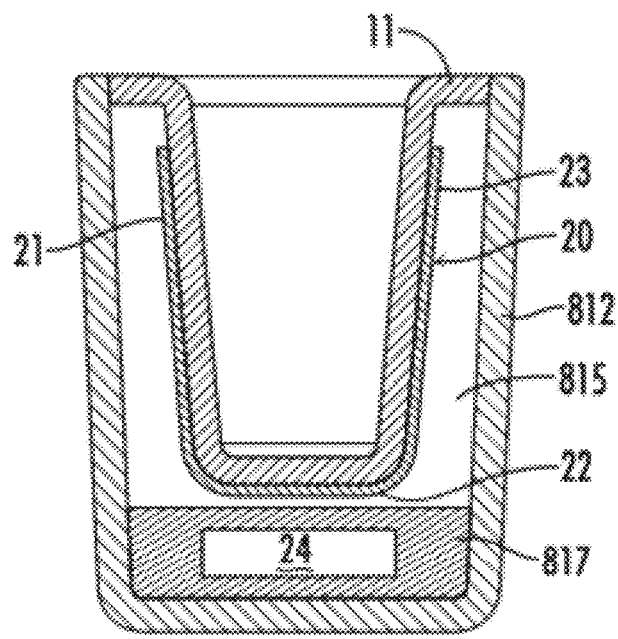
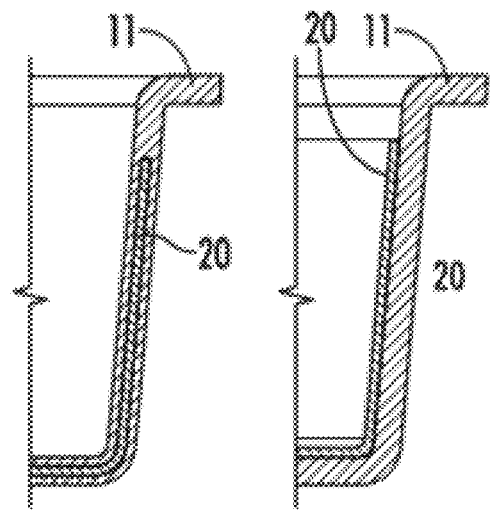
FIG. 8    FIG. 9    FIG. 10
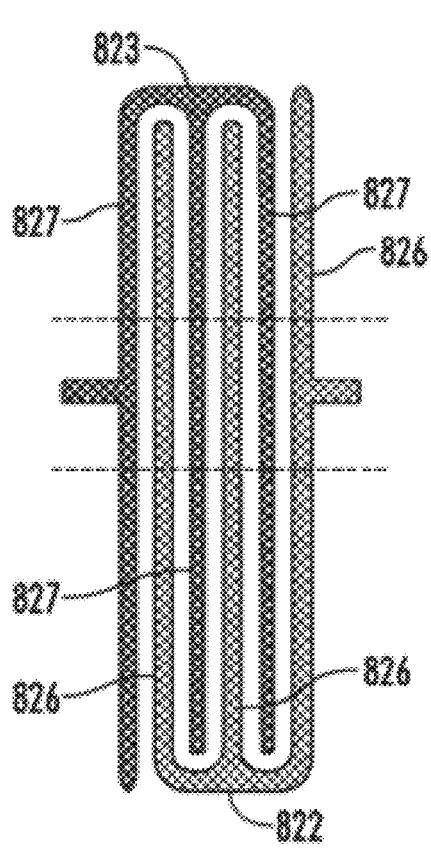
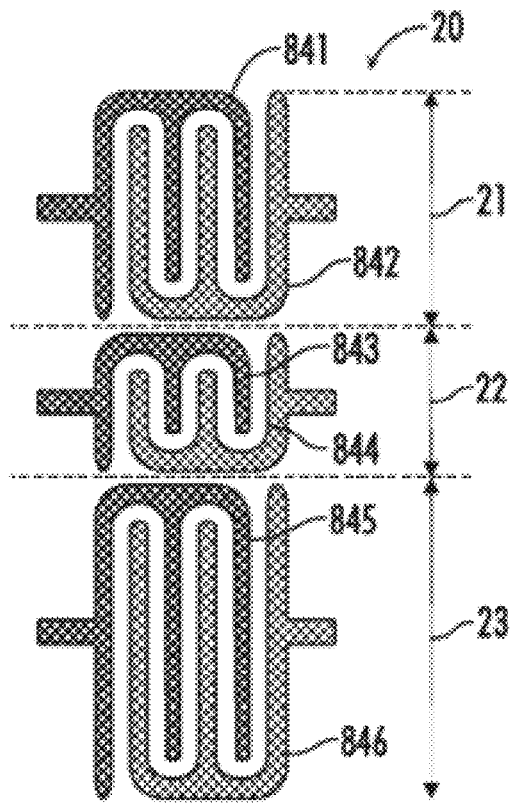
FIG. 11    FIG. 12

SYSTEMS AND METHODS FOR MONITORING PHYSIOLOGICAL PARAMETERS WITH CAPACITIVE SENSING

CROSS REFERENCE TO RELATED APPLICATIONS

This application is a continuation of U.S. patent application Ser. No. 16/174,163, entitled, "Systems and Methods for Monitoring Physiological Parameters with Capacitive Sensing," and filed on Oct. 29, 2018. U.S. application Ser. No. 16/174,163 claims the benefit of U.S. Provisional Application No. 62/578,209, entitled "A System and Method for Physiological Monitoring of Users Using Capacitive Sensing" filed on Oct. 27, 2017. U.S. application Ser. No. 16/174,163 is also a continuation-in-part of U.S. patent application Ser. No. 15/239,810, entitled "Liquid Container Systems and Methods for Monitoring User Hydration," and filed on Aug. 17, 2016, which application claims priority to U.S. Provisional Application No. 62/205,839, entitled "Systems and Methods for Monitoring Liquids in a Container" filed on Aug. 17, 2015, U.S. Provisional Application No. 62/241,494, entitled "Systems and Methods for Monitoring Liquids in a Container" filed on Oct. 14, 2015, and U.S. Provisional Application No. 62/330,692, entitled "Smart Bottle Systems and Methods" filed on May 2, 2016. All of the previously listed applications are incorporated herein by reference.

RELATED ART

Liquids are consumed and used in numerous human endeavors. The ideal parameters for the consumption of a liquid changes based on the context in which the liquid is being used or consumed. For example, it may be desired to maintain a particular level of hydration as a result of a medical condition, during exercise, or to optimize the consumption of particular liquids. It may also be desired to monitor the amount of liquid calories that are consumed or to limit the consumption of liquids having undesirable ingredients. Some patients, such as kidney or heart patients, require strict control and limiting of daily intake of liquids. Certain conditions may require a preferred liquid consumption profile throughout the day. Hydration needs may change as a result of user's activity or state. It would be beneficial to monitor hydration status directly using unobtrusive sensors on objects of everyday use. However, existing methods for monitoring hydration status require complex setups like special rooms, infrared optical spectroscopy, or whole body bioelectric impedance analysis.

In addition, precise monitoring of the rate of excretion of bodily fluids (e.g., total urine output and urine flow) may provide an early alert to impending kidney/organ failure. The current practice in a hospital setting includes the manual assessment of the amount of urine in a collection bag several times per day or the use of electronic devices for continuous monitoring. The automatic continuous volume-flow monitoring of this parameter may reduce human error, save expensive medical staff time, and provide an early alert to impending kidney/organ failure in an already complex care environment. However, the determination of impending kidney/organ failure based solely on the amount of collected urine may be inaccurate since there is no way to correlate the amount of collected urine to the amount of fluid consumed by the patient.

Further, the ubiquitous monitoring of a user and the implementation of health applications in smart homes requires low power and robust vital sign monitoring through unobtrusive means. Traditional methods for wearable monitoring include bioamplifiers (ECG), optical methods (pulse oximeters in smart watches), and piezoelectric/piezoresistive sensors. The bioamplifiers operate in conjunction with a signal conditioning circuit and may use capacitive coupling as a method of AC coupling and the elimination of a DC offset from the input signal. However, these methods may be complex to implement and/or require more power than is desired for extended use.

Biometric authentication can be complex to implement for objects of everyday use. The most popular form of biometric authentication is an image processing technique applied to features in a 2D image (e.g., face, fingerprint, iris, palm-print, etc.) to extract unique physiological features of the user. However, this form of biometric authentication may be impractical for some objects such as a pill bottle. It would be beneficial to have a "smart pill bottle" with sensors that could simply and easily detect unauthorized handling of the bottle, such as by a child, and generate an immediate warning to deter a child from opening the bottle in order to avoid unintentional child poisoning.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 8 is a cross-sectional view depicting an exemplary container system having a capacitive sensor positioned on an exterior surface of an inner container that is inserted into an outer container.

FIG. 9 is a cross-sectional view depicting an exemplary container system having a capacitive sensor embedded in an inner container that is inserted into an outer container.

FIG. 10 is a cross-sectional view depicting an exemplary container system having a capacitive sensor positioned on an interior surface of an inner container that is inserted into an outer container.

FIG. 11 depicts an exemplary capacitive sensor, such as is depicted by FIG. 8.

FIG. 12 depicts an exemplary capacitive sensor comprising a pair of side portions and a bottom portion that separately sense capacitance.

DETAILED DESCRIPTION

Figure 1A:
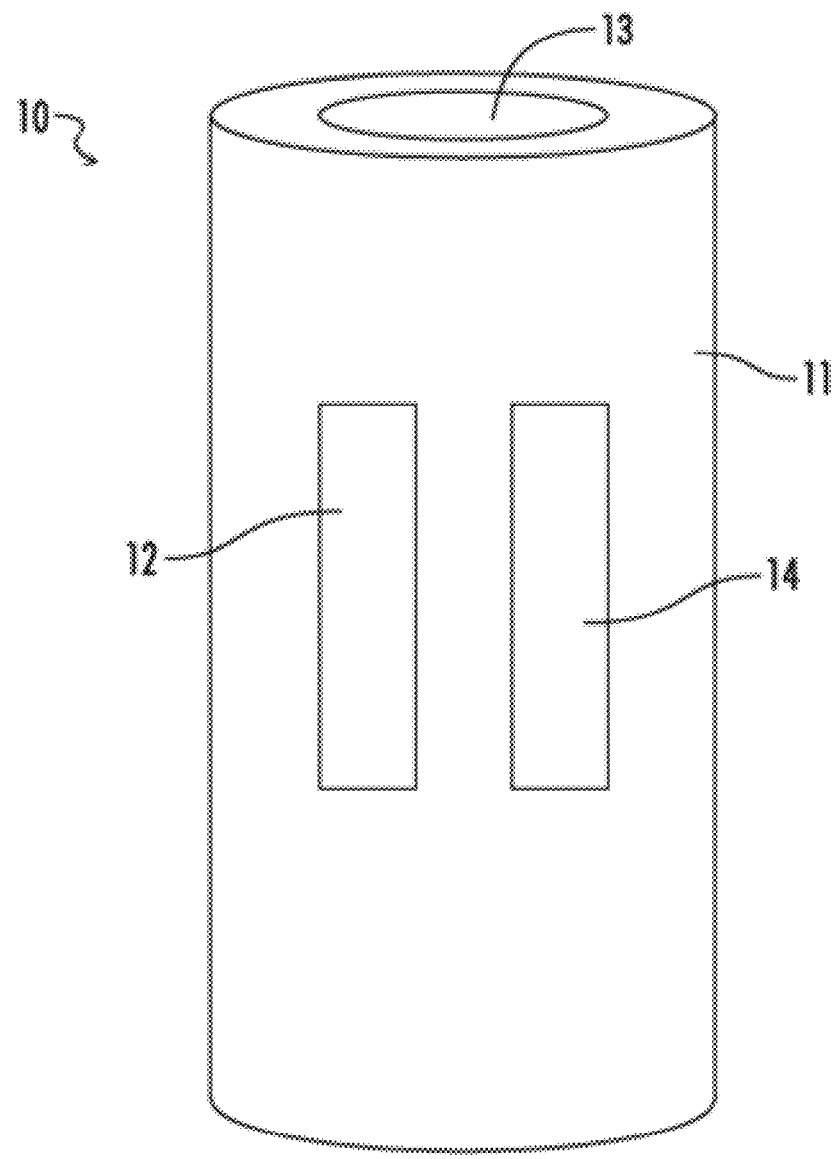
FIGS. 1A-1C depict a perspective view, top view, and cross-sectional view of an exemplary smart container.

The present disclosure generally pertains to smart containers for use in monitoring user hydration and/or other smart objects for use in monitoring physiological parameters of a user. In one exemplary embodiment, a smart beverage container has an interior volume that is capable of holding a volume of a liquid. The smart container also comprises at least one sensor for sensing an amount of the liquid within the container. The liquid is monitored over time to determine an amount of liquid consumed by a user, and feedback is provided to the user indicating whether the user's liquid consumption is within a desired range. Such feedback may include information for indicating when the user is to consume additional liquid in order to remain in compliance with a desired liquid consumption regimen, as well as reminders to take additional liquid or warn the user if too much liquid had been consumed. More generally, the smart container can be used to monitor the consumption or use of any liquid stored in the smart container. Alternatively, the smart container can monitor the level of a liquid being stored or captured by the smart container.

In one exemplary embodiment, the amount of liquid in the container is measured by at least one capacitive sensor fixedly located at one or more locations of the container. The capacitive sensor is configured to provide a capacitive signal representative of the volume of liquid in the container, or a section of the container. The smart container can also have at least one additional sensor fixedly located at one or more locations of the container. Such additional sensor is configured to capture additional sensor data. The smart container can include a processing module fixedly attached to the container. The processing module of the smart container can include a memory, a clock, control logic, and a communication interface. The control logic is configured to receive the capacitive signal, the additional sensor data, and a clock signal from the clock, and is configured to determine liquid information data (such as the level of the liquid, the volume of the liquid and the rate at which the level or volume is increasing or decreasing) based on one or more of the capacitive signals, the additional sensor data, and the clock signal. The control logic is also configured to store the liquid information data in the memory and provide at least a portion of the liquid information data to the communication interface. The communication interface is configured to communicate with an electronic device, such as a smartphone or a remote server via a wireless communication link (e.g., a router), and to transmit the liquid information data to the electronic device.

In one exemplary embodiment, the communication interface is also configured to receive one or more warnings or indications from the electronic device or a server. The control logic is configured to provide the one or more warnings or indications to the user interface, and the user interface is configured to display the one or more warnings or indications.

In one exemplary embodiment, the control logic is configured to generate one or more warnings or indications based on the liquid information data and to provide the one or more warnings or indications to the user interface. The user interface is configured to display the one or more warnings or indications. As an example, the control logic may be configured to track consumption of the liquid in a beverage container over time based on at least one parameter indicative of an amount of liquid in the beverage container. If the amount of liquid consumed during a time period is inconsistent with a target hydration profile (e.g., more or less than a desired amount to be consumed according to the targeted hydration profile) for the user, the control logic may be configured to initiate a warning, which is displayed by the user interface. Such warning may be in the form of a text message or some other format. As an example, the user interface may comprise one or more light sources (e.g., light emitting diodes) that are illuminated as a warning that too much or too little of liquid has been consumed. In other examples, other types of warnings, such as audio beeps or spoken message, may be provided.

In another embodiment, a smart object can include similar components to the smart container but can use a capacitive or optical sensor to measure a physiological parameter, such as heart rate or blood pressure, of a user. The capacitive sensor can be located on the exterior of the object and measure a capacitance associated with the user coming into contact with the capacitive sensor. The measured capacitance, or more specifically, the changes in capacitance, can then be used to determine the desired physiological parameters of the user. For example, a user's heartbeat can be detected by detecting corresponding changes in capacitance measured by a capacitive sensor that is being touched by the user. In an embodiment, the smart container may also have exterior capacitive sensors and operate similar to the smart object to provide physiological information on the user of the smart container.

Figure 1B:
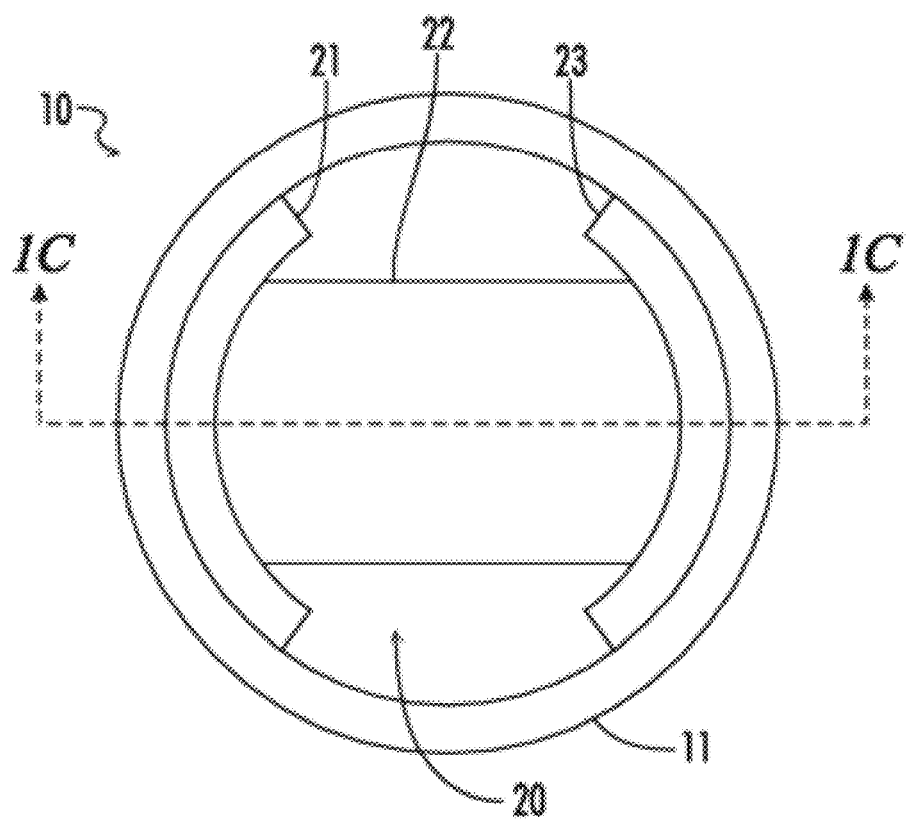
Figure 1C:
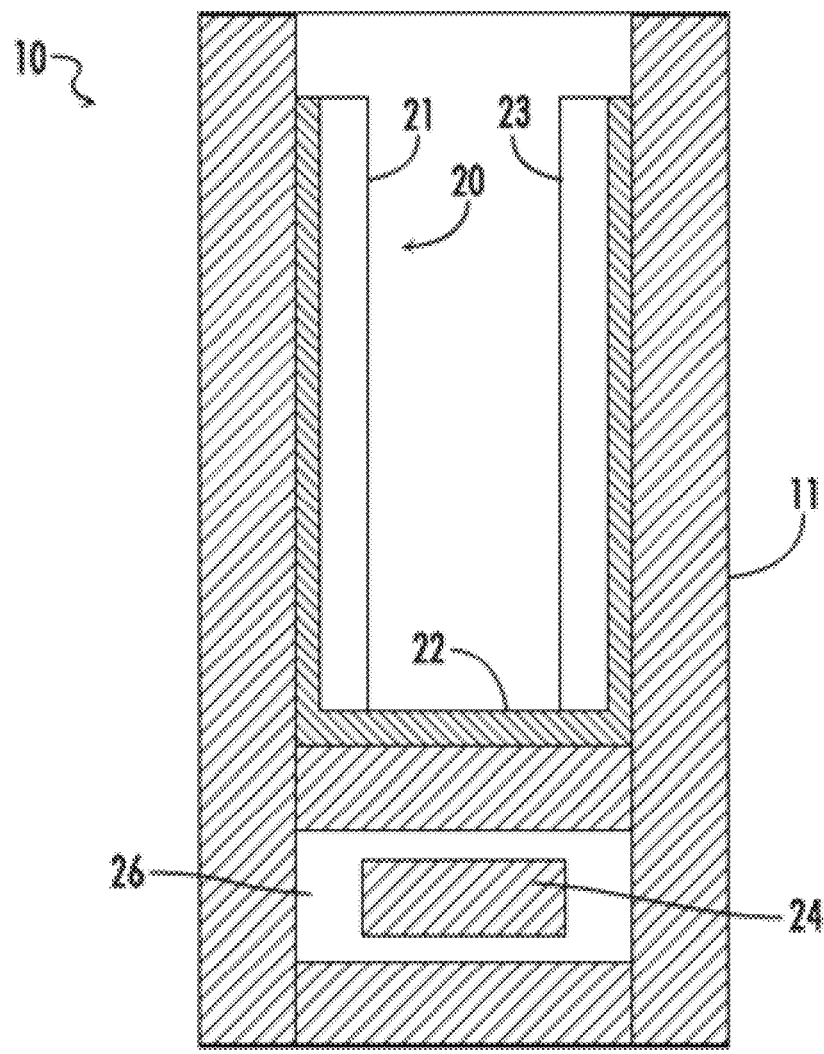

FIGS. 1A-1C depict a perspective view, top view, and cross-sectional view of an exemplary smart object 10 configured as a smart container. Referring to FIG. 1A, a perspective view of smart object 10 configured as a smart container is depicted. Smart object 10 includes at least one container 11 for holding a beverage. Container 11 may be any suitable container that may hold a consumable liquid, such as a cup, bottle, water bottle, sports bottle, baby bottle, intravenous (IV) therapy bag or any other known beverage or consumable liquid container. In the exemplary embodiment of FIG. 1A, container 11 includes a bottom, a cylindrical side, and an opening 13. Although container 11 is depicted in this manner, it will be understood that container 11 may be any suitable object that is able to contain a liquid and selectively provide a user with access to a liquid, e.g., through an opening. In other embodiments, the container 11 can be any type of container that may be used to collect, supply and/or store liquids not intended for human consumption (e.g., catheter bag, gas can, liquefied petroleum (LP) gas tank, oil drain container, colostomy bag, rain gauge, etc.).

Also depicted in FIG. 1A are user interface 12 and sensors 14. In the exemplary embodiment of FIG. 1A, user interface 12 and sensors 14 are depicted as attached to an external surface of container 11. It will be understood that user interface 12 and sensors 14 may be provided for the smart object 10 at any suitable location, including being integrally formed with container 11. User interface 12 may allow a user to interact with smart object 10, as described in more detail hereafter. User interface 12 may provide information about smart object 10, such as environmental information, information relating to a liquid in container 11, information relating to a user of smart object 10, any other suitable information, or any combination thereof.

FIG. 1B depicts a top view of smart object 10, including a capacitive sensor 20 located on an interior surface of container 11. In other embodiments, the capacitive sensor may be embedded within a wall of container 11 or located on an exterior surface of container 11. Although capacitive sensor 20 is depicted as located and physically attached to the interior surface of container 11, it will be understood that capacitive sensor 20 can be implemented with container 11 in any suitable manner that facilitates accurate capacitive sensing. For example, the capacitive sensor 20 may be integrally formed with container 11, or with a suitable dielectric material of container 11 may be located on an exterior surface of container 11.

As will be described in more detail below, it is possible for the container 11 to be inserted into and detachable from an outer container (not shown in FIG. 1B). When desired, the container 11 may be removed from the outer container to allow washing and sterilization of the container 11 without exposing the contents of the outer container to high temperatures that may be associated with a washing or sterilization process, or completely replaced as a disposable part with the limited period of use. As an example, a processing module for receiving and processing signals from the capacitive sensor 20 may be located on the outer container such that it is not subjected to the washing or sterilization process when the container 11 is removed from the outer container. In such embodiment, capacitive sensor 20 can be connected to the processing module through electrical contacts or wirelessly (as described below) to facilitate measurements.

In one embodiment, capacitive sensor 20 may include a left portion 21, a center portion 22, and a right portion 23. Left portion 21 and right portion 23 may extend along opposing sides of container 11. In this regard, the size and location of left portion 21, center portion 22, and right portion 23 or capacitive sensor 20 may be configured in a manner to provide optimum capacitive sensing for any particular shape of container 11. In one embodiment, a center portion 22 runs along a bottom surface of container 11. Capacitive sensor 20 provides a capacitive signal based on the volume of liquid that is inside of the container 11. Portions 21, 22, and 23 can be monitored separately; by monitoring all three segments as a single segment, a more robust monitoring independent of the container position can be achieved.

FIG. 1C corresponds to a cross-sectional view of smart object 10 along section line 1C of FIG. 1B. As is depicted in FIG. 1C, a left portion 21 of capacitive sensor 20 is located on an interior left-side surface of container 11, a right portion 23 of capacitive sensor 20 is located on an interior right-side surface of container 11, and a bottom portion 22 of capacitive sensor 20 is located along a bottom surface of container 11. In other embodiments, any of the portions 21-23 can be embedded in a wall of the container 11 or located on an exterior of the container 11. Each of the portions 21-23 may be one or more electrodes affixed to the container 11. Also depicted in FIG. 1C is a cavity 26. Located within cavity 26 is a processing module 24. As will be described in more detail herein, processing module 24 may receive inputs from sensors 14 and capacitive sensor 20, may interact with user interface 12, and may communicate with other devices such as other smart objects 10 or electronic devices (e.g., smartphones, tablets, smart watches, personal computers, etc.). Although processing module 24 is depicted as located within cavity 26, it will be understood that processing module 24 may be located at any suitable location of smart object 10. For example, processing module 24 may be located integrally with container 11 of smart object 10, on an exterior surface of container 11, on an interior surface of container 11, or in any other suitable location. Whether or not processing module 24 is located within cavity 26, it will also be understood that processing module 24 need not be located at a bottom or base of container 11, but may be located at any suitable location of container 11.

Figure 2:
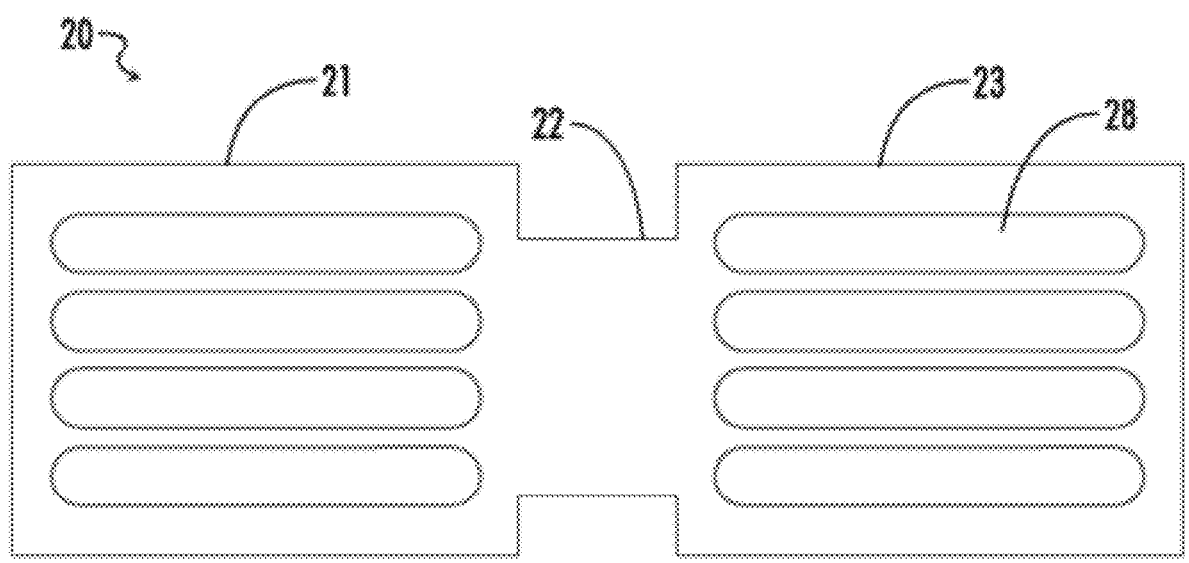
FIG. 2 depicts an exemplary embodiment of a capacitive sensor in accordance with some embodiments of the present disclosure.

FIG. 2 depicts an exemplary embodiment of capacitive sensor 20 in accordance with some embodiments of the present disclosure. Capacitive sensor 20 provides a signal indicative of a volume of liquid within smart container 11 based on capacitive sensing of the liquid. To accurately sense information about a liquid, capacitive sensor 20 may be designed to suitably fit to container 11. For example, each of left portion 21 and right portion 23 may have a height and width that encompass a large proportion of the height of container 11 as well as a significant portion of the width or radius of container 11. In some embodiments, a pattern 28 may be applied to capacitive sensor 20 in a manner that reduces the overall size of capacitive sensor 20 without limiting the capacity for capacitive sensing.

There are a variety of techniques that can be used to capacitively sense the amount of liquid in the container 11. In one embodiment, the left and right portions 21 and 23 are used to sense a capacitance between the portions 21 and 23. Such capacitance should generally change as the amount of liquid between the portions 21 and 23 changes. Thus, the processing module 24 can be configured to estimate the amount of liquid in the container 11 based on the capacitances measured by the portions 21 and 23. Note that tilting of the container 11 can have an effect on such capacitances. In this regard, a different capacitance measurement may occur when the container 11 is tilted relative to an embodiment when the container 11 is not tilted even though the amount of liquid in the container 11 is the same. When the container 11 is tilted toward portion 21, the capacitance of portion 21 will be higher due to the higher level of liquid that is pulled by gravity into the vicinity of portion 21 and higher dielectric constant of the liquid; at the same time, the portion 23 on the opposite side will have reduced level of liquid and smaller capacitance. Therefore, combined capacitance of 21 and 23 provides stable measurement independent of the tilt of the container 11.

Based on the capacitance measurement of the portion 22, the processing module 24 is configured to adjust the capacitance measurements of the portions 21 and 23 in order to provide more accurate estimates of the amount of liquid in the container 11. As an example, the processing module 24 may automatically calibrate the capacitance measurements of the portions 21 and 23 based on a capacitance measurement of the portion 22. In this regard, during such a calibration process, capacitance measurements may be taken for each portion 21-23 while the container 11 is empty in order to determine a minimum capacitance value for the portions 21-23. Then, when a liquid is poured into the container 11 such that the bottom of the container 11 and thus the bottom portion 22 are covered with liquid while the container 11 is upright, the processing module 24 can determine relative dielectric constant caused by the presence of liquid in the vicinity of sensors 21-23. Further, the processing module 24 may be provisioned with information indicative of the respective sizes of portions 21-23. Based on the capacitance measurement by the bottom portion 22, the processing module 24 may calculate the maximum capacitances that should be measured by each of the side portions 21 and 23. As an example, when the bottom portion 22 is completely covered with liquid, the processing module 24 may use the capacitance measurement from the bottom portion 22 to calculate a value indicative of the amount of capacitance that is measured per unit of length or area of the bottom portion 22 (e.g., picoFarad per millimeter (mm) or picoFarad per $mm^2$). Using such value and the respective sizes of the side portions 21 and 23, the processing module 24 may calculate the maximum capacitance measurement to be expected from each of the portions 21 and 23 when the container 11 is full of liquid assuming that the capacitance sensed by the portions 21 and 23 will be proportional to the capacitance sensed by the bottom portion 22 based on the size differences between the portion 22 and the portions 21 and 23.

For example, if all of the portions 21-23 are of the same width, then the maximum capacitance sensed by the portion 21 should be equal to C (y/x), where C is the capacitance measured by the portion 22, y is the length of the portion 21, and x is the length of the portion 22. Knowing the maximum capacitance that should be measured by a portion 21 or 23 when the container 11 is full of liquid, the processing module 24 can calibrate the capacitance measurements by the portion 21 or 23. As an example, if the inner width of the container 11 is uniform from top to bottom, it may be assumed that the capacitance of a portion 21-23 varies linearly from its minimum value to its maximum value as the amount of liquid in the container 11 varies from a minimum (e.g., container is empty) to a maximum (e.g., container is full), and the processing module 24 is configured to convert a capacitance measurement into a volume of liquid estimate based on the minimum and maximum capacitances determined during calibration. In other embodiments, other relationships between capacitance and liquid volume may be used depending on the shape of the container 11 and other factors.

Figure 3:
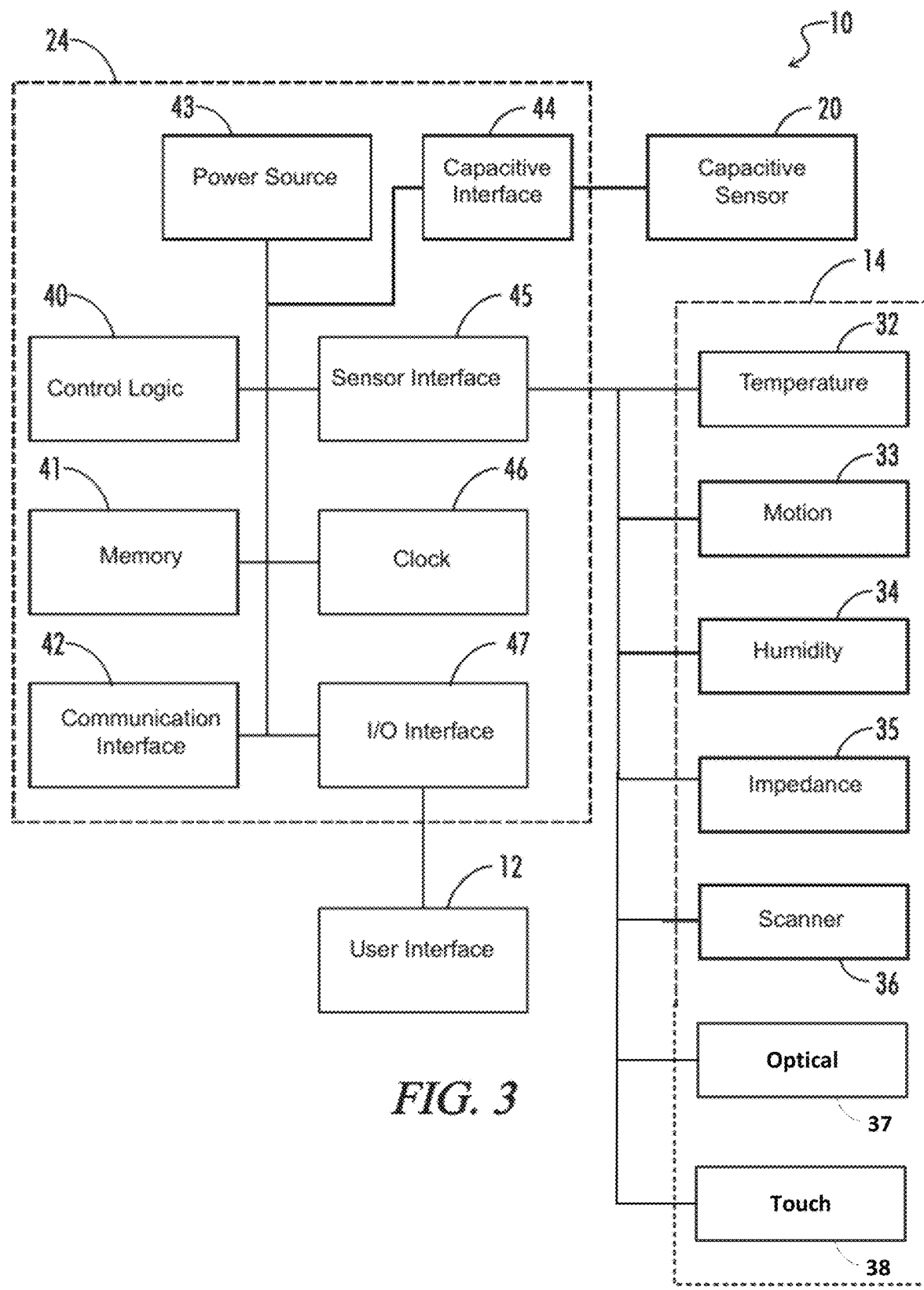
FIG. 3 depicts a block diagram of an exemplary processing module, capacitive sensor, additional sensors, and user interface of a smart container.

FIG. 3 is a block diagram of an exemplary processing module 24, capacitive sensor 20, additional sensors 14, and user interface 12 of smart object 10. Processing module 24 may monitor capacitive sensor 20 and sensors 14 and may also facilitate communication with the user of smart object 10 through user interface 12. Capacitive sensor 20 may include any suitable arrangement of electrodes that permit capacitive sensing of the volume of container 11 that includes the liquid, although in an exemplary embodiment, capacitive sensor 20 may be a patterned capacitive sensor as depicted in FIG. 2.

FIG. 3 depicts a number of exemplary additional sensors 14 including a temperature sensor 32, motion sensor 33, humidity sensor 34, complex impedance sensor 35, scanner 36, optical sensor 37 (e.g., a photoplethysmographic (PPG) sensor), touch sensor 38 and/or combinations thereof.

Although particular sensors are depicted in FIG. 3, processing module 24 may receive sensor information from any suitable sensor 14. Suitable sensors may include sensors that are able to determine information about a liquid within container 11, sensors that are able to determine information relating to the environment in which the smart object 10 is being used, and sensors that are able to determine information about a user of smart object 10. Thus, while particular sensors are described for use in certain applications, it will be understood that any suitable sensors may be used for any suitable applications.

In one embodiment, a temperature sensor 32 may measure the temperature of a liquid within smart object 10, an exterior temperature (e.g., ambient air temperature), or both. A temperature of the liquid may be used for numerous applications. In one exemplary application, the temperature may be used to determine whether a liquid is suitable for drinking, for example, if a liquid is too hot to be consumed. In another embodiment, the type of liquid may be known such that it is known that certain temperatures or humidity levels are likely to result in spoilage of the liquid over time. For example, dairy products exposed to high temperatures for an extended period may be likely to spoil. If the container 11 is a baby bottle, the temperature sensor 32 can be used to determine whether the liquid in the container 11 is at a temperature that may injure an infant that drinks from the container 11 and the humidity sensor 34 may be used with temperature sensor 32 to determine if the contents of the container 11 may have spoiled, which may also injure an infant that drinks from the container 11. In other embodiments, temperature information may be used to optimize consumption of the liquid. For example, it may be desirable to consume certain liquids within a particular temperature range for the liquid. Based on information from temperature sensor 32, processing module 24 may determine whether the liquid is within the desired temperature range. In other embodiments, temperature sensor 32 may be used to determine when the type of liquid within smart object 10 has changed. For example, a change in the temperature that is sensed by temperature sensor 32 over a short time period may indicate that the type or volume of liquid inside smart object 10 has changed. This information can be used to indicate optimum temperature of the liquid for the user (e.g., temperature of the baby food with predefined tolerance of temperature). When the processing module 24 determines that the liquid is unsuitable for consumption (e.g., the temperature has been above a threshold for a sufficient amount of time to indicate that spoilage is likely or the temperature is otherwise outside of a desired range for consumption), the processing module 24 may be configured to initiate a warning, such as a textual or graphical warning message to be viewed by the user.

In one embodiment, the processing module 24 receives an input indicating the type of liquid that is in the container 11. Further, memory 41 stores data indicative of a desired temperature range associated with the liquid type. If the measured temperature is outside of the desired range, then the processing module 24 may provide a warning via the user interface 12 or otherwise. Note that the data may be temporal in nature. For example, the data may indicate that a warning is to be generated if the temperature is within a specified range for at least a specified amount of time. In such case, the processing module 24 determines how long, based on clock 46, the temperature is within the indicated range (e.g., above a temperature threshold), and generates a warning if the cumulative time is above a predefined time threshold.

A temperature sensor 32 may also measure temperature information relating to the environment in which smart object 10 is used. An environmental temperature measurement may be used to optimize the consumption of a liquid within smart object 10. In one embodiment, processing module 24 may provide indications to user interface 12 for a user to increase or decrease the rate at which they are consuming a liquid based on a sensed environmental temperature. As an example, when ambient air temperature is above a predefined threshold, the processing module 24 may increase the amount of liquid that is to be consumed over a given time period in an attempt to ensure that the user remains sufficiently hydrated in elevated temperature conditions.

In some embodiments, sensors 14 of smart object 10 may include one or more motion sensors 33. Motion sensors 33 may include any suitable motion sensor such as accelerometers, gyroscopes, magnetometers, proximity sensors, any other suitable sensor, or any combination thereof. Motion sensors 33 may provide information that is useful in determining the optimum consumption of liquid within smart object 10. In one embodiment, information from motion sensors 33 may be used to determine when a user is consuming liquid from smart object 10. Such information may be used for numerous purposes, such as determining the rate of which a user is consuming a liquid. For example, information about when a user is consuming a liquid as determined from motion sensors 33 may be used on combination with information about the volume of liquid in smart object 10 (e.g., from capacitive sensor 20) and clock 46 to determine the rate at which a user is consuming the liquid. In another embodiment, information from motion sensors 33 may be used to determine an appropriate time to consume a liquid within smart object 10. For example, when smart object 10 is experiencing a large amount of motion, it may not be desirable to consume a liquid within smart object 10. Such information may also be combined with information from other sensors (e.g., temperature sensor 32) to determine when it is appropriate to consume a liquid (e.g., for consumption of hot liquids). Pattern of motion in time (e.g., orientation of the container) may be used to characterize the use of the container, or identify the user, as described below.

In one embodiment, motion sensors 33 may be used to provide a wake up signal for the electronics of smart object 10. When a motion sensor 33 (e.g., a gyroscope or accelerometer sensing motion, or a proximity sensor sensing presence) senses that the smart object 10 is being used, a signal may be provided to processing module 24. Prior to the signal being provided, the components of smart object 10 may be in a sleep mode or low sampling rate to limit power consumption. In response to the motion sensors 33 identifying the use of smart object 10, the components of smart object 10 may wake up and operate normally or increase the sampling rate.

Sensors 14 may also include one or more humidity sensors 34. In one embodiment, humidity sensor 34 may measure the humidity of the environment in which smart object 10 is being used. Depending on the type of liquid that is being consumed, it may be desirable to change the rate at which the liquid is consumed, for example to increase the consumption rate if the humidity is high. In some embodiments, it may be desirable to discard a liquid if it is located in a high humidity environment over an extended period of time (e.g., due to spoilage). In some embodiments, a value for liquid volume data may be adjusted based on the humidity and/or temperature. An initial liquid volume value may be determined based on the measurement from the capacitive sensor. That initial liquid volume data may be adjusted based on known characteristics of the liquid in response to temperature or humidity.

Sensors 14 may also include impedance sensor 35. Although an impedance sensor 35 may be implemented in any suitable manner, in one embodiment an impedance sensor 35 may include a plurality of electrodes that provide a waveform signal at a certain frequency or combination of frequencies and that is transmitted through the liquid of smart object 10. Based on the changes in the amplitude and phase of the waveform signal, characteristics of the liquid within smart object 10 may be determined. In this manner, impedance sensor 35 operating in conjunction with processing module 24 may be able to identify and distinguish between liquids based on a known profile of the liquid or may be able to identify a nutritional content of liquids (e.g., sugar, fat, carbohydrate, calories, and salt content). Such information may be used for monitoring applications as are described hereafter.

As an example, information indicating the capacitance and impedance ranges for a plurality of liquids may be stored in the memory 41. The processing module 24 may be configured to compare such information to the measured capacitance and impedance of the liquid in order to identify the type of liquid that is currently in the object 10. Based on such liquid type, the processing module 24 can determine nutritional information, such as caloric intake or the intake of certain substances (e.g., sugars or carbohydrates), of the consumer liquid. The feedback provided to the user may include such nutritional information as may be desired. In addition, the liquid type information may be used by the processing module 24 to determine the desired range of consumption. As an example, the processing module 24 might target a higher consumption amount for water relative to sports energy drinks.

In another embodiment, the impedance sensor 35 and corresponding electrodes or contacts may be located on the exterior of smart object 10 and measure a complex impedance (including real and imaginary components) associated with a user holding or touching the smart object 10. The impedance sensor 35 can operate like a hydration sensor and determine the total body water (TBW) or total body water percentage (TBW %) of the user from the measured complex impedance. The determined TBW or TBW % can then be used to determine a dehydration or lack of hydration level associated with the user. The impedance sensor 35 can emit signals (e.g., a sine waves) of different frequencies at a first electrode. The signals flow through the hand of the user and are then detected at a second electrode. The impedance sensor 35 can include an amplifier to amplify the detected signals at the second electrode, or an integrated network analyzer for bioelectrical impedance analysis (e.g., Analog Devices AD5933). In an embodiment, the complex impedance can be measured at 1 KHz, 5 KHz, 50 KHz and 100 KHz. The measured complex impedances can then be used to assess the relative change of hydration level of the user based on a formula that is personalized to the user. In an embodiment, the impedance sensor 35 can incorporate 2 (or more) first electrodes and 2 (or more) second electrodes.

Sensors 14 may also include a scanner 36. Scanner 36 may be any suitable device that may determine a type of liquid based on identifying information such as a liquid label. In one embodiment, scanner 36 may be a barcode or QR code scanner. In this manner, information relating to a liquid that is placed inside smart object 10 may be ascertained. Scanner 36 may provide the bar code or QR code information to processing module 24, which may have corresponding nutritional information in a memory or may acquire such information by communicating with an external computing device or server. This information may be used along with information from capacitive sensor 20 or other of sensors 14 for purposes such as caloric or nutritional monitoring.

The optical sensor 37 can be used to measure physiological parameters such as heart rate, blood oxygen saturation (SpO2), and/or any other corresponding physiological parameter. In an embodiment, the optical sensor 37 can be integrated into the exterior of the object 10. With the integration of the optical sensor 37 into the exterior of the object 10, each time the object 10 is handled or touched by a user (e.g., to consume a liquid), the optical sensor 37 can be used to measure the user's heart rate and/or blood oxygen saturation. The optical sensor 37 can then provide data indicative of such measurement(s) to processing module 24 for subsequent monitoring of the measurements and/or other related parameters.

Figure 40:
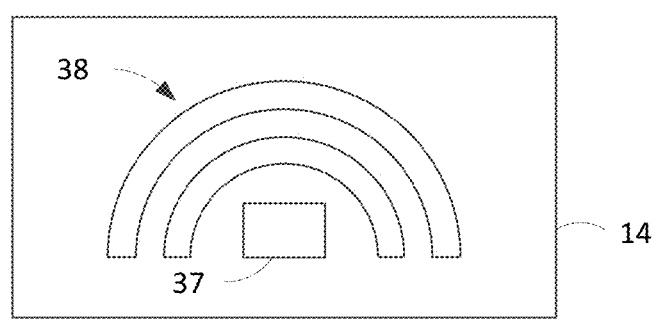
FIG. 40 depicts an embodiment of a sensor incorporating an optical sensor and a capacitive touch sensor.

Touch sensor 38 can be used to detect handling or touching of object 10 and/or other parameters (including physiological parameters of the user). The touch sensor 38 can be integrated into the exterior of the object 10 and can include a capacitive sensor. In an embodiment, as shown in FIG. 40, sensor 14 can incorporate both a touch sensor 38 and an optical sensor 37. The touch sensor 38 in FIG. 40 can be used to detect touching or contacting of the object 10 such that a determination can be made as to when the object 10 is being handled or used and to activate or "turn on" the optical sensor 37 only when the object 10 is being used, thereby significantly reducing power consumption of the optical sensor 37. In another embodiment, changes of capacitance detected by touch sensor 38 can be combined with measurements from optical sensor 37 to provide a more robust measurement of heart rate.

The sensor 14 shown in FIG. 40 can include a 2-layer printed circuit board (PCB) having dimensions of about 0.625 inches by about 0.920 inches. In an embodiment, the optical sensor 37 can be from the Maxim MAX310X family of heart rate and pulse oximeter sensors having dimensions of about 5.6 mm and 2.8 mm and can include two light emitting diodes (LEDs), a photodetector, optimized optics and low-noise analog signal processing. The sensor 14 can include a power management circuit (not shown) that can be positioned on the bottom of the PCB for use with both 1.8 V and 3.3. V power supplies. The processing module 24 can communicate with the optical sensor 37 via I2C. The processing module 24 can provide instructions to the optical sensor 37 directed to low power mode control, FIFO control, LED power usage and temperature measurement control. The optical sensor 37 can provide a raw PPG signal to the processing module 24 that can then digitize the PPG signal. The top layer of the PCB can include a capacitive sensor for touch sensor 38.

Smart object 10 also includes a user interface 12. User interface 12 may vary in complexity from a simple user interface to a complex user interface. As an example of a simple user interface, a user interface 12 may include a series of LEDs (e.g., red, yellow, and green LEDs or a single, multicolor, LED) and a plurality of buttons that can include one or more capacitive touch buttons. LEDs may be used to communicate various types of information, such as when it is acceptable to drink a liquid or when it is necessary to drink a liquid. A plurality of buttons may be used to input simple information such as selecting between types of liquids. In some embodiments, user interface 12 may be a complex user interface. Although a complex user interface may be implemented in any suitable manner, an example of a complex user interface may be a touch screen interface. A touch screen interface may allow complex interface information to be displayed to the user and may allow the user to input data (e.g., information relating to a liquid being consumed) or otherwise interact with a visual display in a complex manner. In other embodiments, user interface 12 may be implemented in any gradation between a simple user interface and a complex user interface. In some embodiments, user interface 12 may include one or more non-visual user interface types. For example, user interface 12 may include a speaker and microphone that operate in conjunction with speech recognition to allow the user to interact with the smart object 10 through voice commands or receive spoken recommendations and notifications.

In some embodiments, user interface 12 may include a biometric interface. A biometric interface may include any suitable components or device that assists in the identification of a particular user of smart object 10. In one embodiment, a fingerprint scanner may be used to identify a user. In other embodiments, a camera may be used to capture images that may be used for facial or iris recognition. Identifying a user (which also may be done through a voice recognition interface) may be useful to associate the user with liquid consumption for operation of a monitoring program.

Smart object 10 also includes a processing module 24. Although processing module 24 may include any suitable components, in one embodiment processing module 24 includes control logic 40, memory 41, communication interface 42, power source 43, capacitive interface 44, sensor interface 45, clock 46, and I/O interface 47. In the embodiment described herein, processing module 24 interfaces with capacitive sensor 20, sensors 14, and user interface 12 to determine liquid information data and provides that liquid information data to an electronic device 70 via communication interface 42. Thus, control logic 40 of processing module 24 performs calculations to determine the liquid information data from the received sensor and user interface information. However, it will be understood that in some embodiments control logic 40 of processing module 24 may perform additional monitoring applications based on the calculated liquid information (e.g., liquid monitoring or nutritional monitoring) or that control logic 40 of processing module 24 may perform fewer processing functions (e.g., transmitting the received sensor and user information to an electronic device 70 for the liquid information data to be determined elsewhere).

Although control logic 40 may be implemented in hardware, software, or any suitable combination thereof, in one embodiment control logic 40 may include one or more processors having processing capability necessary to perform the processing functions described herein, including but not limited to hardware logic, computer readable instructions running on one or more processors, or any suitable combination thereof. In an exemplary embodiment, control logic 40 may have at least one processor for running software to perform the operations described herein, including software accessed in machine readable form on a tangible non-transitory computer readable storage medium, as well as software that describes the configuration of hardware such as hardware description language (HDL) software used for designing chips. In some embodiments, the processor may include a general- or special-purpose microprocessor, finite state machine, controller, computer, central-processing unit (CPU), field-programmable gate array (FPGA), application specific integrated circuit (ASIC), or digital signal processor.

Control logic 40 is in communication with each of the components of processing module 24 and controls the operation of smart object 10 through the components of processing module 24. Through interfaces of processing module 24, control logic 40 is able to control sensors and read sensor data, communicate with a user via user interface 12, and communicate with other electronic devices via communication interface 42. Through operational circuitry of processing module 24 (e.g., memory 41, power source 43, and clock 46) control logic 40 is able to control the operation of components of processing module 24 and read and access stored information.

Processing module 24 includes memory 41, which may be a tangible storage medium. Examples of tangible (or non-transitory) storage medium include disks, thumb drives, and other forms of memory. Tangible computer readable storage medium include volatile and non-volatile, removable and non-removable media, such as computer readable instructions, data structures, program modules or other data. Examples of such media include RAM, ROM, EPROM, EEPROM, flash memory, disks or optical storage, magnetic storage, or any other non-transitory medium that stores information that is accessed by a processor or computing device. In exemplary embodiments (not depicted), one or more computer readable storage media may be integrated with control logic 40, may be one or more other components of processing module 24, may be located on another device, may be located at a remote location, or any combination thereof.

In one embodiment, memory 41 may store information including operational data, user data, sensor data, and liquid information data. Operational data may include any suitable data for operating smart object 10 and any components thereof. Operational data may include instructions that run on the processor of control logic 40 for operating smart object 10. Operational data may also include information relating to the operation of the components of smart object 10, such as communication protocols or information for communication interface 42, control information for power source 43, scaling and control information for capacitive sensor 44 and sensor interface 45, control information for clock 46, and information relating to the available input and output options for user interface 12 (via I/O interface 47). User data may include any suitable information relating to a user, such as identifying information (e.g., name, age, gender, weight, and height), stored user records (e.g., a history of liquid information, liquid monitoring information, or nutritional monitoring information), sensor data (e.g., raw sensor data captured from capacitive sensor 20 or sensors 14), and liquid information data (e.g., calculated information about a liquid within smart object 10).

Processing module 24 also includes a communication interface 42. Communication interface 42 may be a wired interface, wireless interface, or any combination thereof. A wired interface of communication interface 42 may include a receptacle to interface with a wired connection and communication circuitry for sending and receiving data over a suitable wired connection (e.g., Ethernet, USB, FireWire, lightning, etc.). A wireless interface of communication interface 42 may include a wireless transceiver and related circuitry for transmitting and receiving data over any suitable wireless interface (e.g., Wi-Fi, Bluetooth, cellular, NFC, etc.). In some embodiments, communication interface 42 may also include processing circuitry for communicating high level data and commands with control logic 40, or in some embodiments, such processing circuitry may be integral to control logic 40.

Processing module 24 also includes a power source 43. In one embodiment, power source 43 may include a battery such as a lithium-ion battery, lithium-polymer battery, nickel-cadmium battery, or nickel-metal-hydride battery. Power source 43 may include a charging interface such as a physical connector to attach to a charger or inductive charging circuitry. Power source 43 may also include control circuitry that allows the charging and output power of the power supply 43 to be controlled (e.g., by control logic 40).

Processing module 24 may also include capacitive sensor interface 44. Capacitive sensor interface 44 may interface with control logic 40, such that control logic 40 may control operational parameters of capacitive sensor 20 (e.g., potential) and receive sensed capacitance values from capacitive sensor 20. Capacitive interface 44 may communicate these sensed capacitance values to control logic 40 as raw values in analog or digital form, or as a data signal that communicates the capacitance value.

Processing module 24 also includes sensor interface 45. Although a single sensor interface 45 is depicted, in some embodiments a separate sensor interface 45 may be included for each of the sensors 14. Sensor interface 45 is able to communicate with control logic 40 in order to control the operation of sensors 14 and provide sensor data (e.g., temperature sensor data, motion sensor data, humidity sensor data, impedance sensor data, scanner sensor data, etc.) to control logic 40. Sensor interface 45 may provide the sensor data to control logic 40 in raw form as an analog or digital signal or via a data signal that includes the sensor data.

Processing module 24 also includes a clock 46. Clock 46 may be any suitable device that provides a clock signal for processing module 24. In some embodiments, clock 46 may provide a plurality of clock outputs or may have a plurality of modes to enable different clock rates. Clock 46 provides a clocking signal for control logic 40 and may also be used to provide other timing references for components of smart object 10.

Processing module 24 also includes an I/O interface 47. I/O interface 47 may allow control logic 40 to control the operation and display of user interface 12 and receive user input via user interface 12. I/O interface 47 may include any suitable circuitry based on the type of user interface 12. In one embodiment of user interface 12 including LEDs and buttons, I/O interface 47 may include circuitry for driving the LEDs and for providing electrical signals in response to interaction with the buttons. In one embodiment of a touch screen, I/O interface 47 may include processing and driver circuitry for controlling a display of the touch screen and receiving touch inputs from the touch screen. In one embodiment of an audio and voice interface 12, I/O interface 47 may include circuitry for providing and receiving electrical signals representative of voice or other audio information, and may include circuitry for providing electrical or data signals representing voice or audio information to control logic 40.

Figure 4:
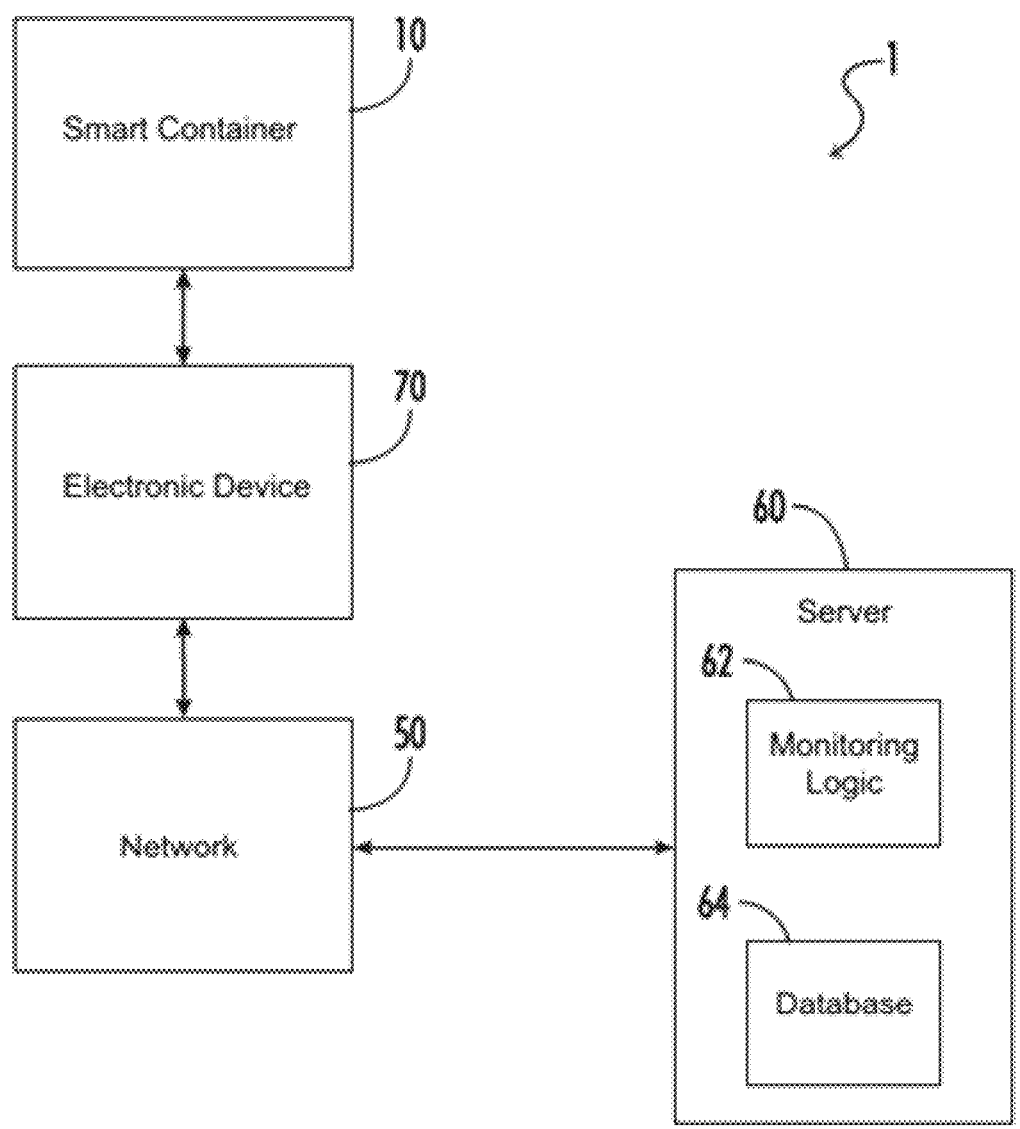
FIG. 4 depicts an exemplary monitoring system including a smart container, electronic device, and server.

FIG. 4 depicts an exemplary monitoring system 1 including a smart object 10, electronic device 70, and server 60. As described herein, smart object 10 monitors capacitive sensor 20 and one or more of sensors 14 to acquire information about a liquid, about an environment where the smart object 10 is being used, and about a user of the smart object 10. In some embodiments the data representing this information may be processed to generate liquid information data, as is described herein. In some embodiments, some or all of the data from the capacitive sensor 20, sensors 14, and user interface 12 may be transmitted elsewhere for processing, such as to electronic device 70 or server 60. Smart object 10 is in communication with the electronic device 70 via its communication interface 42, and in this manner is able to communicate with electronic device 70. In an embodiment, the electronic device 70 can determine the proximity of the smart object 10 to the electronic device 70 based on the strength of the signal received by the electronic device 70 from the smart object 10. In another embodiment, the smart object 10 may communicate directly with server 60 via network 50 without having to use electronic device 70.

Although electronic device 70 may be any suitable device for interacting with smart object 10 and server 60, in one embodiment, electronic device 70 may be a consumer electronic device such as a smartphone, smart watch, tablet, laptop computer, or personal computer. Electronic device 70 has a first communication interface (e.g., Wi-Fi, Bluetooth, NFC, etc.) for communicating with smart object 10. Electronic device 70 may also include one or more software programs (e.g., applications) for interacting with smart object 10 and server 60, as well as one or more processors for executing the software of the electronic device 70. In one embodiment, a software program of electronic device 70 may include a monitoring program that includes functionality for monitoring information about liquid consumption for a user that can be determined based on information acquired by smart object 10 (e.g., liquid information data). Electronic device 70 may also include software that provides data to perform some or all of the user interface functions for smart object 10. The display and user interface of the electronic device 70 (e.g., touch screen, microphone, keyboard, mouse, camera, etc.) may provide rich user interface functionality for providing information to processing module 24 of smart object 10, including such information as user information or information about a liquid that is contained in smart object 10.

In one embodiment, electronic device 70 may run a hydration and liquid monitoring program. The hydration and liquid monitoring program may provide an interface for providing information regarding a liquid that is being consumed, such as by displaying visual depictions regarding the consumption of liquids, comparisons to target consumption or consumption rates, information about liquids consumed (e.g., nutritional or other information), or any other suitable information as described herein. In another embodiment, the electronic device 70 may execute a liquid collection program that provides an interface for providing information about a liquid that is being collected by the container 11.

In one embodiment, electronic device 70 may include a camera or barcode scanner for acquiring information from a product or label, such as a label on the container of a drink that is poured into the smart object 10. A user may also enter a search query manually, for example through voice commands, a touch screen, or a keyboard. The barcode, QR code, or manual query may be transmitted to server 60 via network 50. Server 60 may include monitoring logic 62 and database 64. The monitoring logic 62 may be implemented in software, hardware, firmware or any combination thereof. As an example, the monitoring logic 62 may comprise one or more processors for executing software to perform its functions, as described herein.

Monitoring logic 62 may be configured to access the database 64 based on the information received from electronic device 70 and transmit responsive information about the liquid to electronic device 70 via network 50. This information may include container volume, calibration constants, nutritional information (e.g., calories, fat, carbohydrates, sugar, sodium, vitamin content, caffeine content, etc.), properties of the liquid (e.g., viscosity, temperatures for consumption, time and temperature characteristics for spoilage, etc.), any other suitable information, or any combination thereof. Personal information about the user that determines personal hydration or nutrition advice can be retrieved from the server 60 or other source and used by the monitoring logic 62 to provide reminders and notifications to the user. Electronic device 70 may use this information for processing of the monitoring program and may also provide some or all of this information to smart object 10 for processing that is performed thereon. Note that the monitoring logic 62 may be implemented at locations other than the server. As an example, the monitoring logic 62 may reside on the container 11 or the electronic device 70, such as a smartphone.

Figure 27:
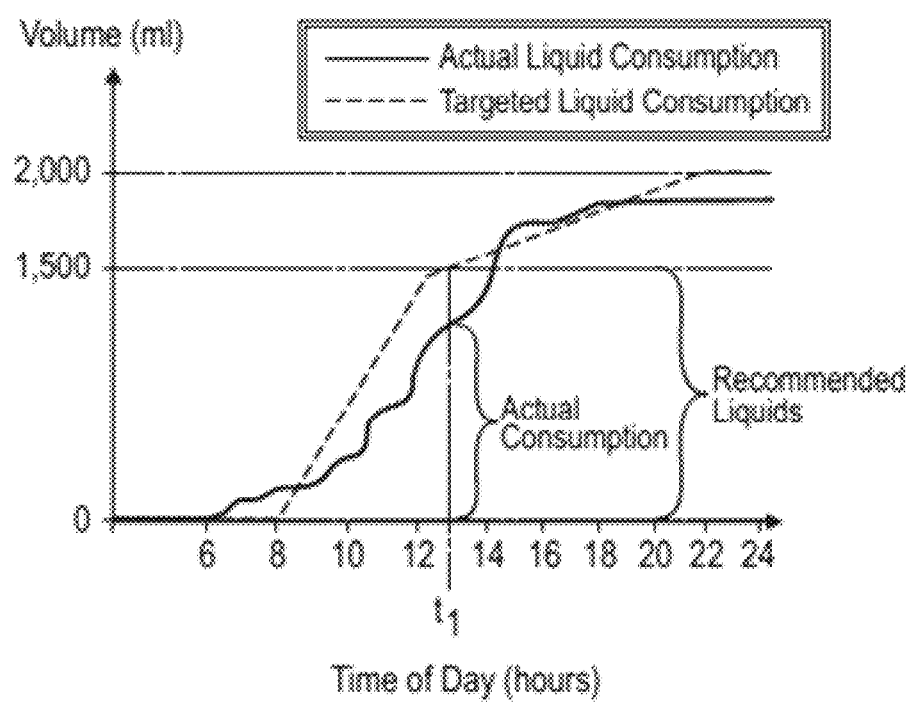
FIG. 27 depicts an exemplary display of liquid information data.

The monitoring application of electronic device 70 may also display liquid information data, liquid monitoring data, and nutritional monitoring data to the user. In one embodiment, liquid information data that is displayed to a user by the monitoring application of electronic device 70 may include the volume of liquid consumed within a time period, the volume of liquid within the container, the rate at which a liquid is being consumed, a comparison of the volume or rate of liquid that is consumed with a target hydration profile during the day or threshold, warnings related to excessive temperatures, warnings related to potential spoilage, any other suitable information, or any combination thereof. An exemplary display of liquid information data is shown by FIG. 27, which illustrates a graph of actual liquid consumption relative to a target hydration profile for a given day. Such profile indicates how much total liquid consumption is desired at various times in the day. In some embodiments, the profile may be defined in terms of rate of consumption (which may vary throughout the day, e.g., increase when ambient air temperature is or predicted to be greater) or other parameters instead of total amount of consumption. Actual consumption is compared to the targeted consumption indicated by the user's target hydration profile and feedback is provided indicating whether the user's consumption is consistent with (e.g., within a certain range) of target hydration profile.

In FIG. 27, the graph shows that at time $t_1$, the actual consumption is below the targeted consumption. If the difference is greater than a predefined threshold, the system may generate a warning indicating that the user should consume more liquid. Such warning may indicate the absolute value of the difference in the targeted liquid consumption and the actual liquid consumption. Note that the display of liquid information data may include cumulative displays for all liquids and displays for individual liquids. The liquid monitoring application on an electronic device 70 may also include liquid monitoring data related to specific health or fitness applications. Liquid consumption can be organized to monitor the group of subjects. The monitoring application can provide current state and the most critical users in relation to recommended hydration regiment.

Liquid monitoring data may be based solely on liquid consumption and the type of liquids being consumed, or in some embodiments may also be based on other health or physical information relating to a user. One example of liquid monitoring data that may be analyzed and displayed by a monitoring program of electronic device 70 may be monitoring data for sports and fitness applications. The monitoring program of electronic device 70 may become aware that a user is engaging in a sports or fitness activity, for example based on a user input, input from motion sensor 33 of smart object 10, inputs from motion sensors of the electronic device 70, or information provided by another device. Based on this information, and in some embodiments information related to the type of liquid being consumed, the monitoring program running on electronic device 70 may determine an optimum amount of liquid to be consumed by the user. This information may be displayed by the monitoring program and in some embodiments may also be provided to smart object 10 to provide indications to the user via user interface 12. For example, indications may provide an indication to consume more liquid, stop consuming a liquid, increase or decrease a consumption rate, change a type of liquid being consumed, and other similar information as described herein.

In one embodiment, the monitoring program may receive data from a hydration sensor (not shown) that provides a measurement of the user's hydration. In this regard, a hydration sensor may be coupled to a device, such as a sensor on the smart object 10 that communicates through sensor interface 45 or a watch worn by the user, and be in contact with the user's skin in order to provide a hydration measurement indicative of the user's hydration level (e.g., indicating whether the user is dehydrated or overhydrated and/or an extent to which the user is hydrated). The hydration sensor may communicate the hydration measurement to the electronic device 70 via a wireless or wired connection, and the monitoring program may use the data from the hydration sensor as a factor in monitoring the user's hydration. As an example, the monitoring program may determine when to indicate to the user that he or she should consume liquid based on the hydration measurement.

In another embodiment, the monitoring program of electronic device 70 may optimize liquid consumption for a health application. For example, users with certain kidney or heart problems may be limited in the amount and types of liquids that they can consume daily. The monitoring program of electronic device 70 may utilize information relating to the amount of liquid being consumed, consumption rate throughout the day, and type of liquid to optimize the amount and types of liquid being consumed. In one embodiment, the monitoring program may tailor a liquid consumption regimen for a user based on known health conditions. This liquid consumption regimen may provide a user with information relating to the types of liquids that should be consumed, when they should be consumed, and at what rate they should be consumed. This information may be displayed at electronic device 70 and may be transmitted to smart object 10 to be displayed at a user interface 12.

Note that the liquid consumption regimen may be based on several factors. As an example, the monitoring program may have access to a table of consumption rates for users afflicted with a certain disease or medical condition. Such rates may be personalized with user age and/or weights. Information indicative of the user's age and weight as well as the user's level of physical activity and other environmental factors (e.g., ambient temperature and humidity from electronic device 70) may be input to the system or otherwise determined (e.g., retrieved from a medical server), and the monitoring program may use such information to look up or otherwise determined the desired consumption rate from the table or formula.

The monitoring program of electronic device 70 may also include an application for monitoring a dosage for medication or prescriptions. In one embodiment, the liquid that is contained in the smart container may be a liquid medication or prescription. In some embodiments, smart object 10 may be a custom container for providing delivery of a medication or prescription (e.g., a nebulizer or inhaler). The monitoring program may monitor the volume of the medication or prescription being consumed and the time at which it is consumed. Based on this information, the monitoring program can provide warnings to stop usage, take a dose of the medication or prescription, or modify the dosage. This information may be displayed at electronic device 70 and may be transmitted to smart object 10 for display at user interface 12.

A monitoring program of electronic device 70 may also include an application for medical fluid monitoring. In some embodiments, the smart object 10 may be custom designed for the holding of medical fluids such as urine or blood (e.g., a catheter bag or specimen collector). Based on the volume, fill rate, or other measured characteristics of the medical fluid, the monitoring program may provide medical information to a patient or medical professional. For example, warnings may be provided if a medical fluid (e.g., blood or urine) has filled its container or is filling at too fast or slow of a rate (e.g., a decrease of urine generation might provide early warning about possible kidney failure). Warnings may also be provided based on the measured characteristics of the medical fluid, using the complex impedance of the liquid inside of the bag. The monitoring program can then consider the hydration rate calculated from another smart object 10 (e.g., smart water bottle or intravenous infusion) to calculate expected rate of filling of a medical fluid into the smart object 10 and to generate warnings in the case of a significant difference. As an example, acute kidney injury (AKI) and/or early kidney failure may be detected from a trend of diminishing output (rate of filling) for a known hydration input.

Figure 45:
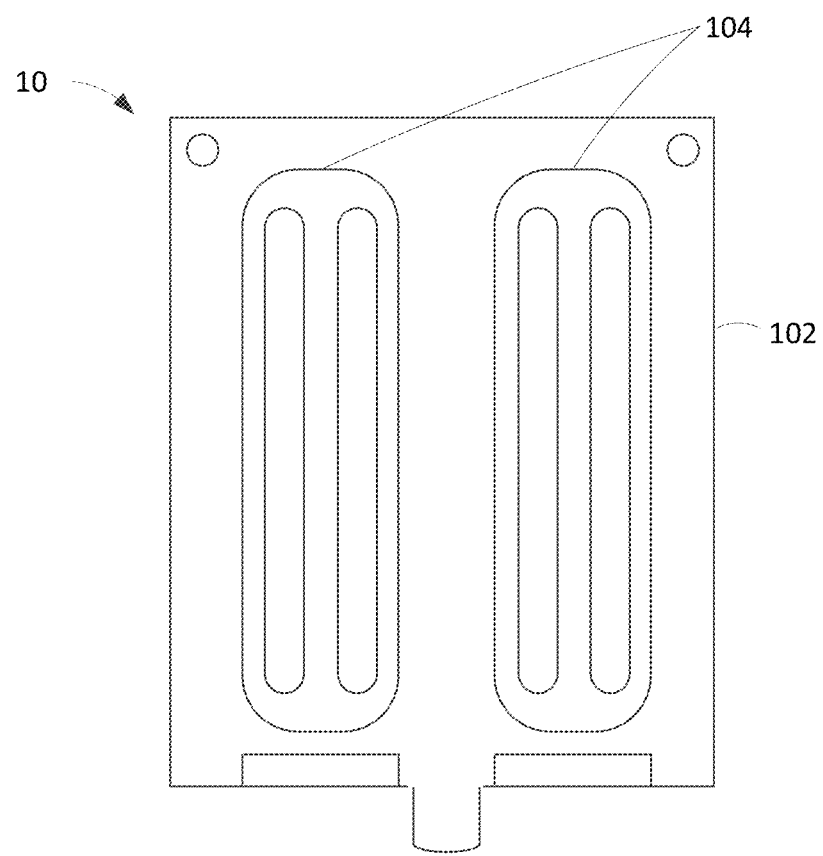
FIG. 45 depicts an embodiment of a smart object configured as a catheter bag.

In an embodiment, the precise monitoring of body fluids associated with a user can facilitate automatic collection of data and real-time analysis of trends for the user. As shown in FIG. 45, the smart object 10 can be a catheter bag 102 designed for the holding of medical fluids such as urine or blood. The catheter bag 102 can include sensors 104 in contact with body fluids stored in the catheter bag 102. The sensors 104 may be used to check the density and chemical composition of fluids in the catheter bag 102.

Based on the volume, fill rate, or other measured characteristics of the medical fluid in the catheter bag 102, the monitoring program of electronic device 70 or server 60 may provide medical information to a patient or a medical professional. For example, warnings may be provided to the patient or medical professional if a medical fluid (e.g., blood or urine) has filled the catheter bag 102 or is filling the catheter bag 102 at too fast or slow of a rate that may be indicative of a medical condition. For example, a decrease of urine generation in a patient might provide an early warning about possible kidney failure, especially if the fluid consumption of the patient is known from another smart container or intravenous infusion. The monitoring program may also provide warnings based on the measured characteristics of the medical fluid in the catheter bag 102, using the complex impedance of the liquid inside of the bag as determined from measurements from the sensors 104.

A monitoring application of electronic device 70 may also monitor nutritional data. Based on information about the amount of liquid consumed, consumption rate, and types of liquid consumed, a monitoring application of electronic device 70 may determine nutritional information such as calories, fat, carbohydrates, sugar, sodium, alcohol, caffeine, or any other suitable nutritional information. This nutritional monitoring program may be used for health monitoring programs, may provide warnings or prompts regarding consumption, and may be combined with other nutritional monitoring programs such as programs for monitoring of food consumption. Information for a nutritional monitoring application may be displayed at electronic device 70 and may also be transmitted to smart object 10 to be displayed at user interface 12.

Any of the liquid monitoring data and nutritional monitoring data that is provided by smart object 10 or electronic device 70 may be provided by electronic device 70 to remote server 60 via network 50. Network 50 may be any suitable network for communicating data between locations, such as the Internet, cellular networks, telephone networks, any other suitable network, or any combination thereof. Remote server 60 may be one or more servers having processors and memory, or in some embodiment, may have distributed processing over a plurality of servers 60 including a plurality of servers 60 at different locations. Server 60 may include monitoring logic 62 and a database 64 or other type of memory. Server 60 may receive information and data such as liquid information, liquid monitoring data, and nutritional monitoring data from electronic device 70 over time and store that data in database 64. Monitoring logic 62 may analyze the data over time to determine consumption patterns and provide analysis for systems to optimize liquid consumption patterns. In one embodiment, monitoring logic 62 may access stored data from database 64 to identify liquid consumption excesses or deficiencies. Examples of liquid excesses may include excessive consumption of liquids high in fat, sugar, alcohol, or caffeine, or improper consumption for a particular medical condition. Similarly, deficiencies may include lack of water during periods of exercise, failure to take medications, and a general failure to consume a sufficient volume of liquids. Based on this analysis, monitoring logic 62 may adjust routines, settings, warnings, and other parameters for the monitoring application of electronic device 70 while transmitting modified parameters to electronic device 70 via network 50.

Figure 5:
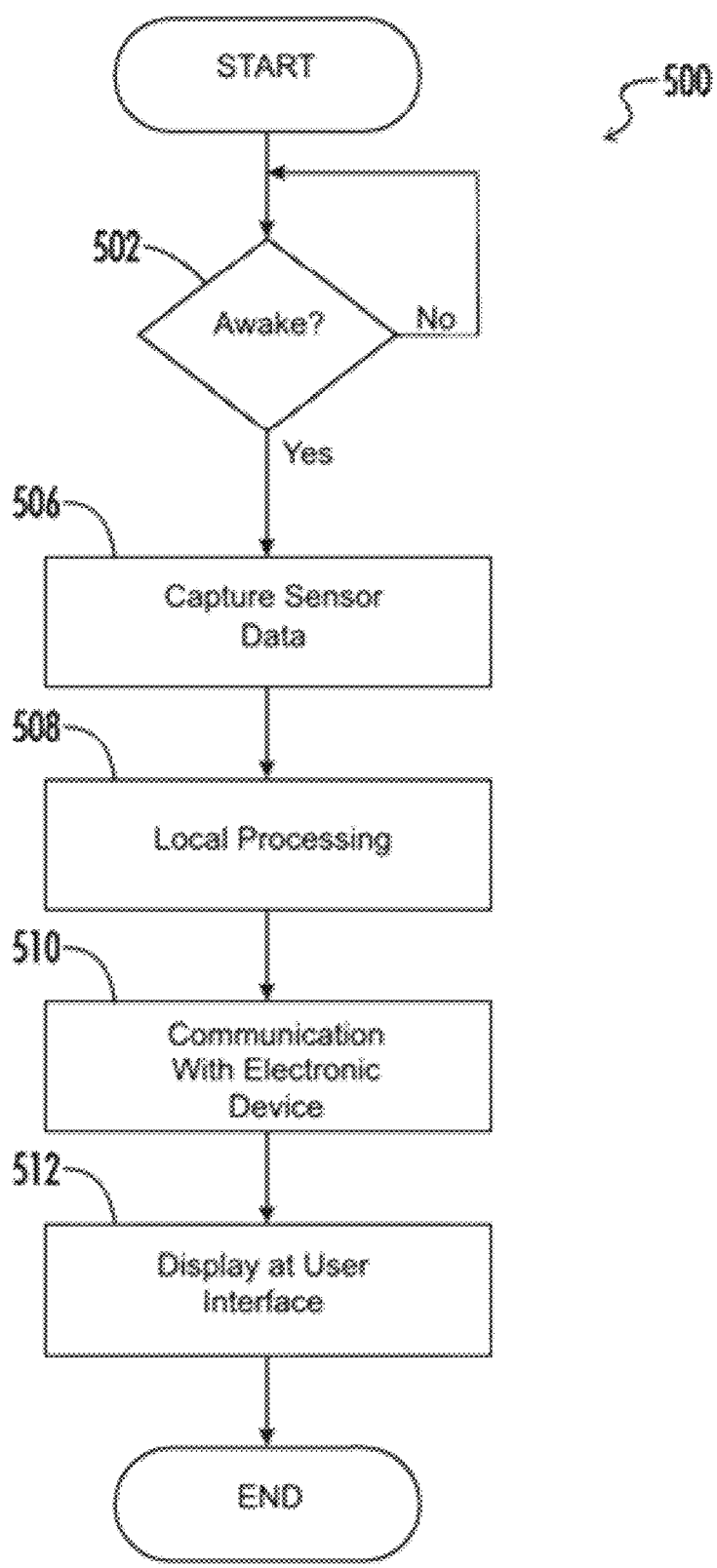
FIG. 5 depicts exemplary steps for analyzing a liquid within a smart container.
Figure 6:
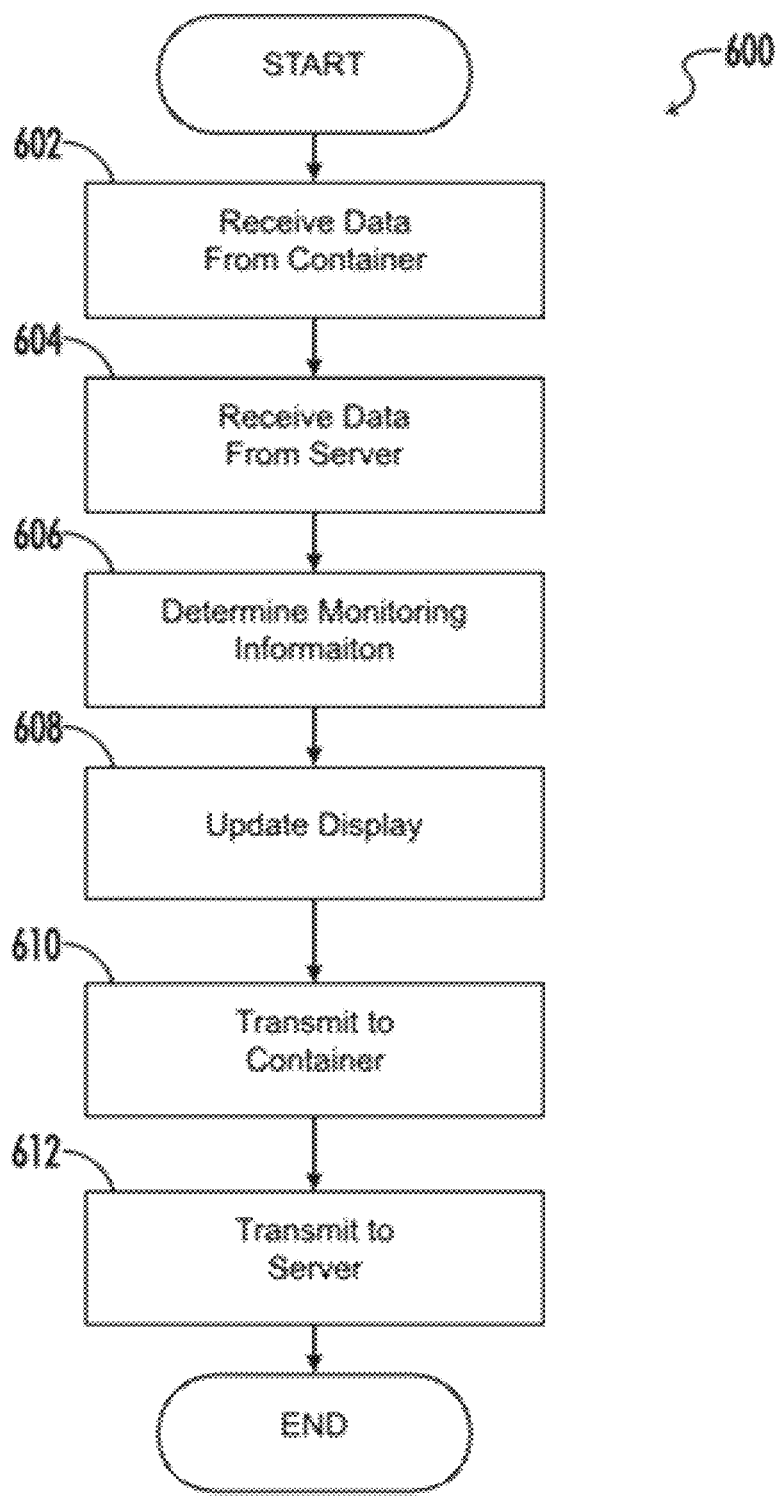
FIG. 6 depicts exemplary steps for processing information about a liquid at an electronic device.
Figure 7:
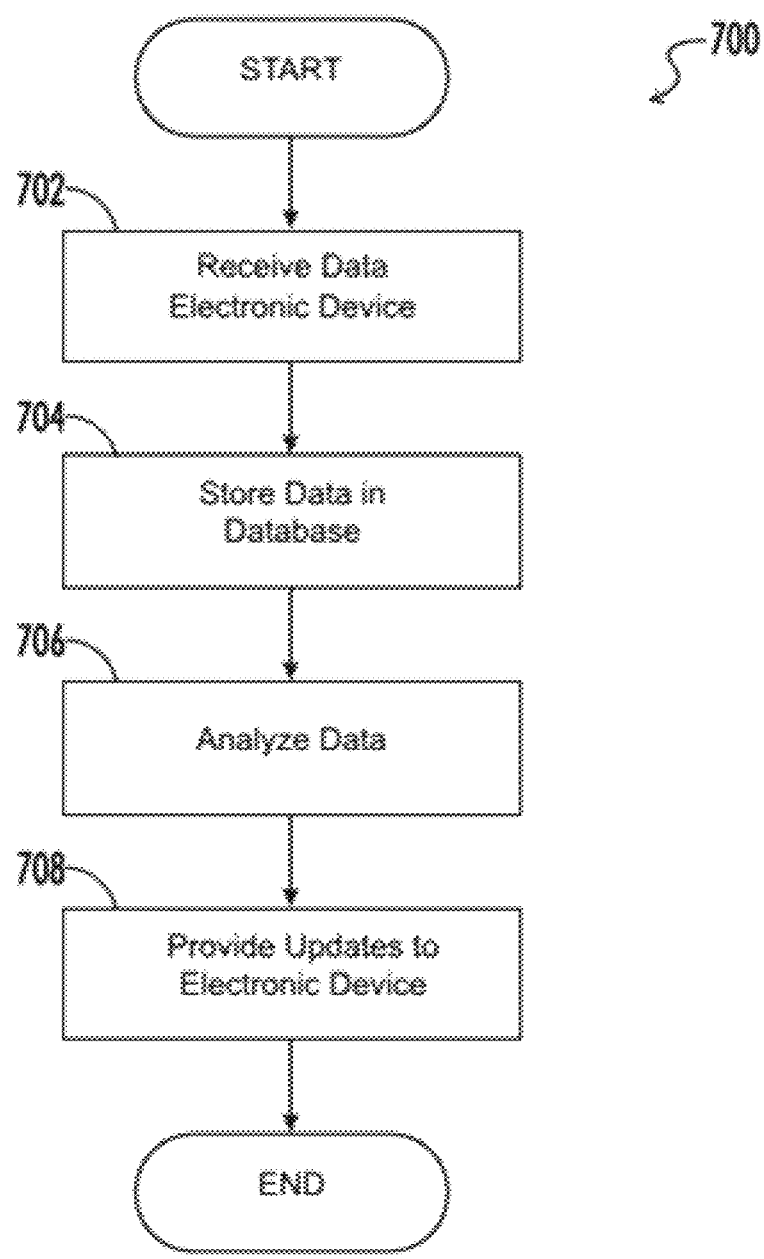
FIG. 7 depicts exemplary steps for performing liquid monitoring at a server.

FIGS. 5-7 depict methods for determining information about a liquid in a smart container according to some embodiments of the present disclosure. While, for purposes of simplicity of explanation, the methods are shown and described as a series of steps, it is to be understood and appreciated that such illustrations or corresponding descriptions are not limited by the order of the steps, as some steps may occur in different order and/or concurrently with other steps from what is depicted and described herein. Any non-sequential, or branched, flow illustrated via a flowchart should be understood to indicate that various other branches, flow paths, and orders of the steps, can be implemented which achieve the same or a similar result. Moreover, not all illustrated steps may be required to implement the methods described hereinafter.

FIG. 5 depicts steps 500 for capturing and analyzing a liquid within a smart object 10. Processing may begin with smart object 10 in a sleep mode. In the sleep mode, numerous components of smart object 10 may be fully or partially disabled, thus conserving power in the sleep mode. For example, any of capacitive sensor 20, sensors 14, user interface 12, and their associated interfaces (capacitive interface 44, sensor interface 45, I/O interface 47) that are not used for waking up the smart object 10 may be disabled. Communication interface 42 may be fully or partially disabled depending on whether it is possible to receive a wake up signal from electronic device 70. Power source 43 may operate in a reduced power mode, clock 46 may provide a clock signal having a reduced clock rate, and control logic 40 may be partially shut down to provide a limited set of functionality. In one embodiment, a wake up signal may be provided by a sensor such as capacitive sensor 20 or motion sensor 33. Capacitive sensor 20 may sense a change in the amount of liquid in smart object 10. Based on this sensed change, control logic 40 may cause the other components of smart object 10 to wake up in order to monitor the liquid as described herein. Motion sensor 33 may sense movement of smart object 10, which may similarly cause the components of smart object 10 to wake up. In one embodiment, capacitive sensor 20 (if located on the exterior of the smart object 10) can detect touching of the smart object 10 and trigger control logic 40. In another embodiment, a wakeup signal may be provided by user interface 12 or electronic device 70 through communication interface 42. In this case, the wakeup signal may be user-initiated in order to turn on smart object 10. In one embodiment, a wakeup signal may be provided periodically based on an elapsed time determined by control logic 40 based on a clock signal from clock 46. In this manner, the components of smart object 10 may wake up periodically. Alternatively, the wake-up signal can be provided at a predefined interval in order to provide for continuous monitoring of the liquid in the smart object 10. If the smart object 10 is not awake, processing may continue at step 502 until it is awake. Once smart object 10 is awake, processing may continue to step 506.

At step 506, processing module 24 may capture sensor data from capacitive sensor 20 and one or more additional sensors 14. Sensor data from capacitive sensor 20 may be provided to control logic 40 via capacitive interface 44 and stored in memory 41. Sensor data for one or more additional sensor data 14 may be provided to control logic 40 via sensor interface 45, and then stored in memory 41. Processing may then continue to step 508.

At step 508, control logic 40 may access the user information and sensor data stored in memory or on the server and perform local processing according to one or more local processing routines. As described herein, a range of local processing routines may be available, including minimal processing such that raw user info and sensor data is provided to electronic device 70, intermediate-level processing such that data such as liquid information data is determined by control logic 40, and complex processing such that one or more monitoring functions are performed by control logic 40. Once the local processing has completed, the resulting data may be stored in memory 41 and processing may continue to step 510.

At step 510, control logic 40 may initiate communications with electronic device 70 via communication interface 42. Control logic 40 may transmit stored data such as liquid information data to electronic device 70. Control logic 40 may also communicate with electronic device 70 to receive information from electronic device 70, such as user information, operational parameters, user input, and updates to local processing routines to be run on control logic 40. Processing may then continue to step 512.

At step 512, control logic 40 may control the display of user interface 12 via I/O interface 47. This may include information that conveys liquid information data, liquid monitoring data, nutritional monitoring data, any other suitable data, or any combination thereof. In some embodiments, a portion of the data to be display at user interface 12 may have been provided via electronic device 70 or server 60.

FIG. 6 depicts steps 600 for processing within a liquid monitoring system by electronic device 70. Processing may start at step 602, at which electronic device 70 may receive data from smart object 10. As described herein, the received data may include raw data relating to sensor outputs, liquid information data, monitoring data, or any combination thereof. A monitoring application of electronic device 70 may store the data and continue to step 604.

At step 604, electronic device 70 may receive data from server 60. Data received from server 60 may include any suitable data such as monitoring data, updates to parameters of the monitoring application of electronic device 70, or any combination thereof. The data received from server 60 may be stored in memory of electronic device 70 and processing may continue to step 606.

At step 606, a monitoring application of electronic device 70 may determine monitoring information such as liquid monitoring information and nutritional monitoring information as described herein. This information may be stored in memory of electronic device 70, and processing may continue to step 608.

At step 608, a monitoring application of electronic device 70 may update the display of electronic device 70. As described herein, the monitoring application may provide information to the user regarding liquid information data, liquid monitoring data, and nutritional monitoring data. The user may interact with this display in response to the display data or based on additional user inputs. The display of electronic device 70 may be updated and information relating to user interaction with the display may be stored in memory. Processing may then continue to step 610.

At step 610, electronic device 70 may transmit data to smart object 10. A monitoring application of electronic device 70 may transmit data to be displayed at a user interface 12 of smart object 10, warnings or indications to be displayed at user interface 12 of smart object 10, parameter updates for performing calculations at smart object 10, software updates for smart object 10, any other suitable information, or any combination thereof. Once the data has been transmitted to smart object 10, processing may continue to step 612.

At step 612, electronic device 70 may transmit data such as liquid information data, liquid monitoring data, nutritional monitoring data, warnings, indications, any other suitable data, or any combination thereof to server 60.

FIG. 7 depicts steps 700 for performing liquid monitoring at server 60. Processing may start at step 702 at which data is received from electronic device 70 via network 50. Processing may then continue to step 704.

At step 704, server 60 may store the received data in database 64. In this manner, server 60 may accumulate a large amount of data regarding a user's liquid consumption and health over time. For example, physiological sensors on the container may collect physiological measures, such as heart rate, blood oxygen saturation, or galvanic skin resistance. That information can be stored on the server along with the liquid consumption data. Once the data is stored in the database 64, processing may continue to step 706.

At step 706, monitoring logic 62 of server 60 may analyze the data that is stored in database 64. In this manner, as described herein, monitoring logic 62 of server 60 may discern long-term patterns regarding a user's liquid consumption or health status. Based on these long-term patterns, monitoring logic 62 may identify additional warnings or indications or may update liquid consumption routines for the user. Once monitoring logic 62 has analyzed the data stored in database 64, processing may continue to step 708.

At step 708, server 60 may communicate with electronic device 70 via server 50 in order to provide updates to electronic device 70. As described herein, those updates may include updates to monitoring protocols, warnings, indications, any other suitable updates, or any combination thereof. Once the updates have been provided to electronic device 70, processing may end.

In various embodiments described above, the amount of liquid in the container 11 is estimated based on capacitance measurements. In other embodiments, other types of measurements for estimating the amount of liquid in the container 11 are possible. In addition, in the embodiments described herein, various functions are described as being performed at the container 11, the server 60, or the electronic device 70. It should be noted that any function performed at any of such components may be performed at any of the other components or at some other location. As an example, the monitoring of data from the capacitive sensor 20 or other sensors may be performed at the container 11, the server 60, the electronic device 70, or other location.

FIG. 8 shows an exemplary embodiment of a container system 800 in which the container 11 is inserted into and removable from an outer container 812 where a cavity 815 is between the container 11 and outer container 812. The outer container 812 has an insert 817 that is positioned at the bottom of container 11 and that includes electronics, such as circuitry for processing module 24, for processing signals from the capacitive sensor 20. When the container 11 is inserted into the outer container 812, the processing module 24 may be electrically connected to the portions 21-23 via one or more electrical contacts (not shown in FIG. 8) so that the processing module 24 may communicate with each section/portion 21-23. In other embodiments, the portions 21-23 may wirelessly communicate with the processing module 24. As described above, having separate containers 11 and 812 permits the container 11 to be replaced or removed from the outer container 812 for washing and sterilization without exposing the components of the container 812, such as processing module 24, to the high temperatures or cleaning substances that may be associated with the washing and sterilization. As shown by FIGS. 9 and 10, it is possible for the portions 21-23 to be embedded in the container 11 or positioned on an inner or outer surface of the container 11.

In addition, as described above, it is possible for the portions 21-23 to be integrated into a uniform structure that spans from one side of the container 11 to the other or for each portion 21-23 to be electrically separated from the other portions. FIG. 11 depicts an exemplary capacitive sensor 20 that forms a uniform structure spanning from one side of the container 11 to an opposite side of the container 11.

Referring to FIG. 11, the sensor 20 comprises a pair of electrodes 822 and 823. Although the electrodes 822 and 823 are shown as flat in FIG. 11 for simplicity of illustration, the electrodes 822 and 823 are actually bent in FIG. 8 so that they conform to the shape of the container 11 as they extend from one side to the other.

As shown by FIG. 11, the electrode 822 has a plurality of fingers 826 that are interleaved with a plurality of fingers 827 of the electrode 823. In one embodiment, the separation distance between the fingers (i.e., the distance from a finger 827 to an adjacent finger 826) is equal to approximately the thickness of the wall of the container 11 on which the sensor 20 is positioned. Even though the liquid is not between the electrodes 822 and 823, the liquid in the container 11 is close enough to the sensor 20 to affect the capacitance that is measured. Note that, in the embodiment shown by FIG. 1, the liquid in the container 11 is between the side portion 21, which is forming one electrode, and the side portion 23, which is forming another electrode. In general, a substance will have a greater effect on the capacitance measured between two electrodes if the substance is between the electrodes. However, depending on the size of the container 11, the distance between the portions 21 and 23 can be relatively large for capacitance measurements. The embodiment shown by FIG. 11 has the advantage of permitting a shorter distance between electrodes 822 and 823 relative to the embodiment shown by FIG. 1. This may enable the sensor 20 to have greater sensitivity to changes in the volume of liquid in the container 11 even though the liquid is not directly between the electrodes 822 and 823.

FIG. 12 shows an exemplary embodiment of the capacitive sensor 20 when each portion 21-23 forms a separate set of electrodes that are arranged similar to the electrodes 822 and 823 of FIG. 11. Specifically, the portion 21 comprises a pair of electrodes 841 and 842 having interleaved fingers, the portion 22 comprises a pair of electrodes 843 and 844 having interleaved fingers, and the portion 23 comprises a pair of electrodes 845 and 846 having interleaved fingers. Thus, each portion 21-23 provides a separate signal indicative of the capacitance measured by the respective portion. The capacitance value from each portion may be used to calculate a total capacitance value indicative of the amount of liquid in the container 11 regardless of the orientation of the container. In this regard, if the container 11 is tilted, it is expected that one of the side portions 21 or 23 would detect a higher capacitance than the other depending on the direction of tilt, but the overall capacitance detected by portion 21 and 23 should be about the same for different angles of tilt of the container 11.

Note that, in some embodiments, the container system 800 may be designed such that the container 11 is not removable from the outer container 812. In such embodiments, the cavity 815 may be evacuated. In an embodiment in which the container 11 is removable from the outer container 812, the conditions in the cavity 815, such as humidity, may vary over time. When the capacitive sensor 20 is in the cavity 815, such as when the portions 21-23 are located on the exterior surface of the container 11, as shown by FIG. 8, the humidity in the cavity 815 may affect the capacitance measured by the sensor 20. In one embodiment, a humidity sensor 34 is positioned in the cavity 815 or otherwise in order to sense the humidity in the cavity 815. In one exemplary embodiment, the humidity sensor as shown in FIG. 11 can be implemented in the processing module 24 to assess the change of capacitance caused by humidity in the cavity 815. The processing module 24 is configured to adjust the capacitance measurement by the sensor 20 in order to account for the humidity in the cavity 815 in order to provide more accurate liquid volume estimates. In addition, adjusting the capacitance measurements based on humidity measurements may be particularly desirable when the capacitance measurements are used to detect the type of liquid in the container 11. In this regard, variations in capacitance measurements resulting from humidity variations may result in erroneous liquid type or volume determinations. By adjusting the capacitance measurements to account for humidity variations, more accurate liquid type decisions can be made.

Figure 13A:
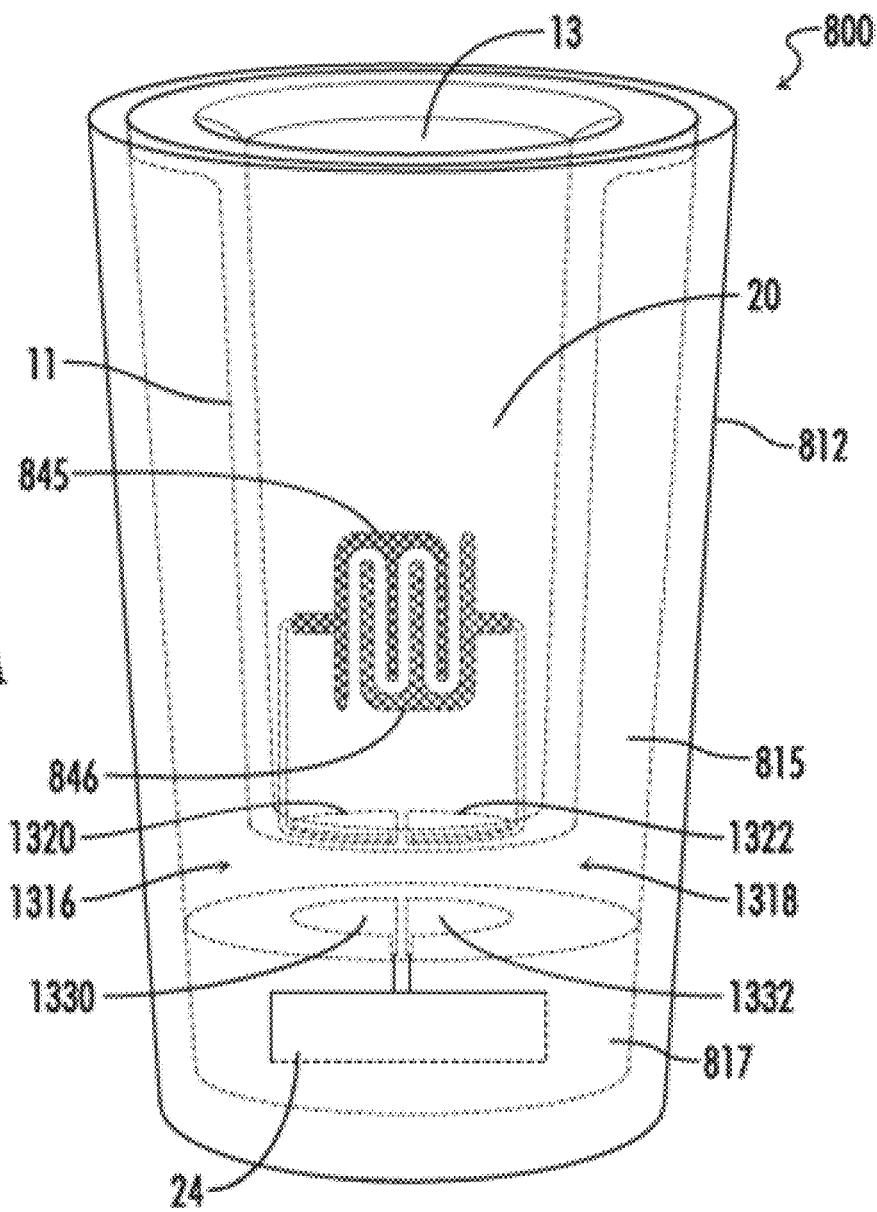
FIG. 13A is a side view depicting an exemplary container system having a capacitive sensor with capacitive, non-contact, interface with a processing module.

FIG. 13A shows an exemplary embodiment of a smart container system 800 in which a capacitive sensor 20 is wirelessly coupled through the capacitance of interface plates of the inner container 11 and interface plates of the processing module 24. In the embodiment shown by FIG.

13A, the capacitive sensor 20 is embedded within the inner container 11, but other configurations of the capacitive sensor 20 are possible.

Referring now to FIGS. 3 and 13A in combination, the capacitive sensor 20 is coupled to a first interface capacitor 1316 that forms a wireless connection between the electrode 845 and the processing module 24, and the capacitive sensor 20 is also coupled to a second interface capacitor 1318 that forms a wireless connection between the electrode 846 and the processing module 24. The interface capacitor 1316 has a flat electrode 1320 embedded in the bottom of the container 11 and a flat electrode 1330 that is positioned on the insert 817 separated from the electrode 1320. In addition, the interface capacitor 1318 has a flat electrode 1322 embedded in the bottom of the container 11 and a flat electrode 1332 that is positioned on the insert 817 separated from the electrode 1322. Thus, the circuit shown by FIG. 13A has three capacitors in series. Specifically, the circuit has one sensing capacitor (i.e., the capacitive sensor 20, which is formed by electrodes 845 and 846 and is used to sense an amount of liquid, as will be described in more detail hereafter). The circuit also has two interface capacitors 1316 and 1318 that are in series with the capacitive sensor 20.

In general, the separation distance of the electrodes 1320 and 1330 and the media (e.g., air, vacuum, or some interface material) between the electrodes 1320 and 1330 are both constant when the inner container 11 is inserted in the outer container 812. Similarly, the separation distance of the electrodes 1322 and 1332 and the media (e.g., air or vacuum) between the electrodes 1322 and 1332 are both constant when the inner container 11 is inserted in the outer container 812. Thus, the capacitances of the interface capacitors 1316 and 1318 should be substantially similar. Any change to the overall capacitance of the circuit thus should be attributable to the capacitance of the capacitive sensor 20. Using this property, the processing module 24 is configured to determine the capacitance of the sensor 20, which is then used to estimate the amount of liquid in the container 11.

In this regard, when the container 11 is inserted into the outer container 812, capacitive coupling occurs between the electrodes 1320 and 1330 and between the electrodes 1322 and 1332, thereby electrically coupling the capacitive sensor 20 to the processing module 24. The processing module 24 is configured to measure the overall capacitance of the circuit and to then determine the capacitance of the sensor 20 using this measured capacitance. Specifically, the overall capacitance of the circuit ($C_{eq}$) can be characterized by the following formula:

$$C_{eq} = 1/(1/C_i + 1/C_s + 1/C_i) = (C_i * C_s)/(C_i + 2C_s)$$

where $C_i$ is the capacitance of a single one of the interface capacitors 1316 and 1318 (assuming that both interface capacitors 1316 and 1318 are of the same size and have the same capacitance) and $C_s$ is the capacitance of the sensor 20 formed by electrodes 845 and 846. Thus, by measuring $C_{eq}$, the processing module 24 can calculate $C_s$, which may be used to determine the volume of liquid in the container 11. Also, if $C_i \gg C_s$ then $C_{eq} = C_s$.

Figure 13B:
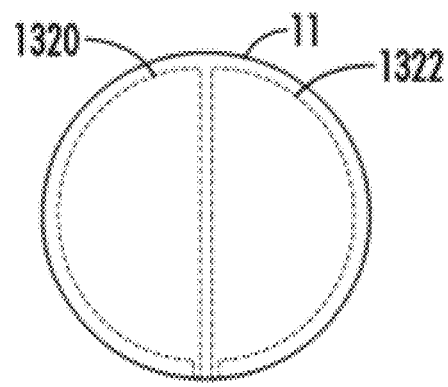
FIG. 13B is a bottom view depicting a bottom of the inner container of FIG. 13A.

Note that electrodes 1320, 1322, 1330, and 1332 with larger areas will generally provide higher capacitances for the interface capacitors 1316 and 1318 and thus more accurate sensing of the capacitance of sensor 20. Similarly, a material with a high dielectric constant placed between inner container 11 and the insert 817 may also significantly increases the interface capacitance $C_i$, thereby making $C_i \gg C_s$. FIG. 13B shows each electrode 1320 and 1322 having a semi-circular shape that conforms to the circular shape of the bottom of the inner container 11 in an attempt to maximize the area of the electrodes 1320 and 1322. That is, the electrodes 1320 and 1322 are arranged to substantially span the entire width of the bottom of the inner container 11 with a small separation between the electrodes 1320 and 1322. If desired, the electrodes 1330 and 1332 on the insert 817 may have the same size and shape as the electrodes 1320 and 1322, respectively, on the container 11. In other embodiments, other shapes of the electrodes 1320, 1322, 1330, and 1332 and/or the bottom of the inner container 11 are possible.

In an effort to more accurately monitor volume of liquid in the container 11, capacitance measurements from at least one of the electrodes 1330 or 1332 on the insert 817 may be used to determine a humidity offset indicative of the environment surrounding the smart container system 800, and the offset may be used to adjust capacitance measurements of sensor 20. More specifically, since the electrodes 1330 and 1332 are exposed to cavity 815 containing air, capacitance measurements from the interface capacitors 1316 and 1318 can be used to measure humidity as a function of capacitance. In one embodiment, the electrodes 1320 and 1330 are connected to a capacitance-to-digital converter (not shown) via electrical contacts. Capacitance measurements from the interface capacitor 1316 can be used to determine an offset due to humidity, and the offset is used to adjust capacitance measurements made by the processing module 24. Note that, in this particular embodiment, container 11 is not removable, because the electrode 1320 is directly connected to the converter. For embodiments in which container 11 is removable, the container system 800 described above in FIG. 13A may be used.

Figure 14:
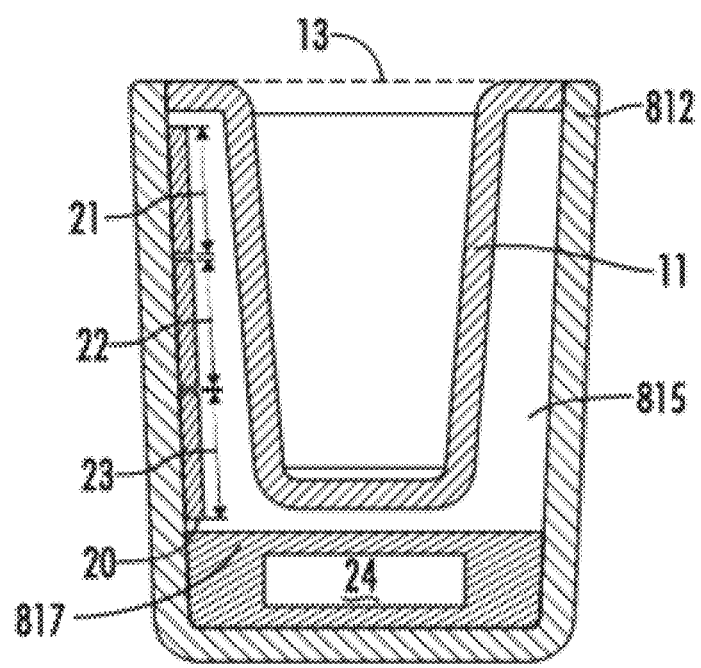
FIG. 14 is a cross-sectional view depicting an exemplary container system having a capacitive sensor on an interior surface of the outer container for the detection of the handling of the container system.
Figure 15:
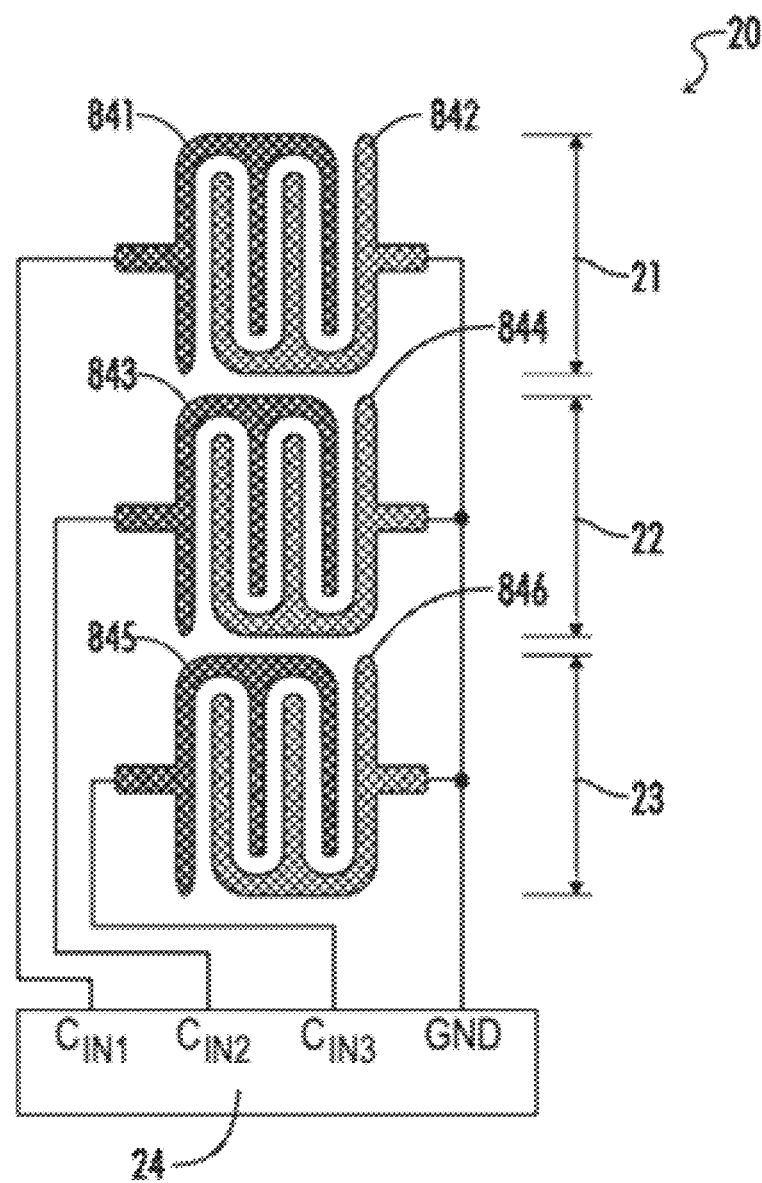
FIG. 15 depicts an exemplary arrangement for coupling a capacitive sensor connected to a processing module, such as is depicted by FIG. 14.

FIG. 14 shows an exemplary embodiment of a smart container system 800 in which the capacitive sensor 20 of FIG. 12 is used to detect handling thereof. Referring now to FIGS. 3 and 14 in combination, portions 21-23 of the capacitive sensor 20 are positioned along the inner surface of the outer container 812 and, as depicted by FIG. 15, connect to the processing module 24 via electrical connections (e.g., wires). The processing module 24 receives capacitance measurements from each portion 21-23 via the sensor interface 45, and control logic 40 detects handling of the smart container system 800 based on changes in capacitance measurements for one or more of the portions 21-23.

As an example, when a user grips the outer container 812 near its base, capacitance of portion 23 changes by at least a threshold amount, and control logic 40 determines, based on this change in capacitance of portion 23, that the user is handling the smart container 800. Likewise, when a user grips the outer container 812 near opening 13, capacitance of portion 21 changes by at least the threshold amount, and control logic 40 determines, based on this change in capacitance of portion 21, that the user is handling the smart container 800. Also, depending on where a user grips the outer container 812, capacitance may change by at least the threshold amount for two or more portions 21-23 of the capacitive sensor 20.

Capacitance measurements from portions 21-23 of the capacitive sensor 20 shown in FIG. 14 may also be used by control logic 40 to determine whether the user is a child or adult. More specifically, since the size of a child's hand is, in most cases, small relative to an adult's hand, a child's hand gripping the outer container 812 should cover less surface area than an adult's hand gripping same. Thus, if the user gripping the outer container 812 is a child, the number of portions 21-23 whose capacitance changes by at least the threshold amount will likely be less than it would be if the user were an adult.

In one embodiment, control logic 40 of the processing module 24 determines, based on the number of portions 21-23 whose capacitance changes by at least the threshold amount, that a child is handling a smart container 800 containing medication and generates an alarm. Specifically, the alarm may be an audible or visual alarm emitted or displayed by user interface 12 of the smart container 800. In another embodiment, the alarm may be a notification in the form of an email or SMS text-message sent to an electronic device (e.g., smartphone, tablet, smart watch, etc.) associated with the owner of the smart container 800, one or more predefined recipients (e.g., child's guardians), or both. In another embodiment, additional segments can be used with the same principle to improve the robustness of the detection.

In yet another embodiment, the smart container system 800 includes a first capacitive sensor 20 embedded in the container 11, and a second capacitive sensor 20 located on the interior surface of the outer container. In one embodiment, the second capacitive sensor 20 may be used to isolate the first capacitive sensor 20 from electrical noise. More specifically, the second capacitive sensor 20 is connected to the processing module 24 as shown in FIG. 15, and control logic 40 changes electrical contacts Cin1, Cin2, and Cin3 from inputs to outputs. Further, control logic 40 makes electrodes 841, 843, and 845 a virtual electrical ground by writing a value of zero to Cin1, Cin2, and Cin3 via the capacitive interface 44. When this occurs, the first capacitive sensor 20 can more accurately measure volume of liquid in container 11, because the second capacitive sensor 20 shields the first capacitive sensor 20 from electrical noise.

Figure 16:
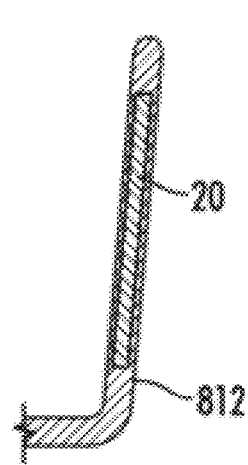
FIG. 16 is a cross-sectional view depicting an exemplary container system having a capacitive sensor embedded in the outer container.
Figure 17:
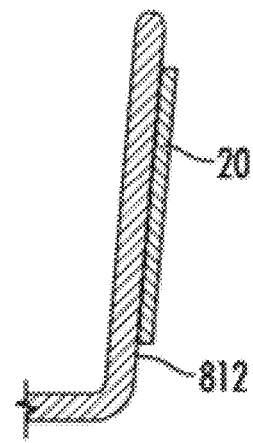
FIG. 17 is a cross-sectional view depicting an exemplary container system having a capacitive sensor on an exterior surface of the outer container.

FIGS. 16 and 17 show that it is possible for portions 21-23 of FIG. 14 to be embedded in the outer container 812 or positioned on an exterior surface of the outer container 812. Note also that, although FIG. 14 depicts the capacitive sensor 20 as only being on one side of the outer container 812, other embodiments may include a capacitive sensor 20 on both sides of the outer container 812. Further, in another embodiment, portions 21-23 of the capacitive sensor 20 may wrap around the entire circumference of the outer container 812.

Referring now to FIGS. 3, 4 and 14 in combination, the capacitive sensor 20 of FIG. 14 may also be used to measure heart rate of a user handling the smart container system 800. For each cardiac cycle (i.e., heartbeat), a pressure wave (change in blood volume), or pulse, propagates through the user's vascular system. When the pressure wave propagates through blood vessels in the user's hand, the dielectric constant of skin on the user's hand changes, which affects the capacitance measurements of at least one of the portions 21-23.

In one exemplary embodiment, the processing module 24 receives capacitance measurements from each of the portions 21-23 via the capacitive interface 44, and control logic 40 determines heart rate from changes in capacitance that occur each time the user's heart beats. In another embodiment, portions 21-23 of the capacitive sensor 20 are connected to a capacitance-to-digital converter (not shown) via electrical connections, and the converter is in communication with the processing module 24 via a serial communication (e.g., I2C, UART, SPI, etc.) link. Also, control logic 40 may store data indicative of the user's heart rate in memory 41, and upload data to electronic device 70 or server 60 at a later time. Still further, control logic 41 may notify the user of his/her heart rate by displaying data on the user interface 12.

Figure 18A:
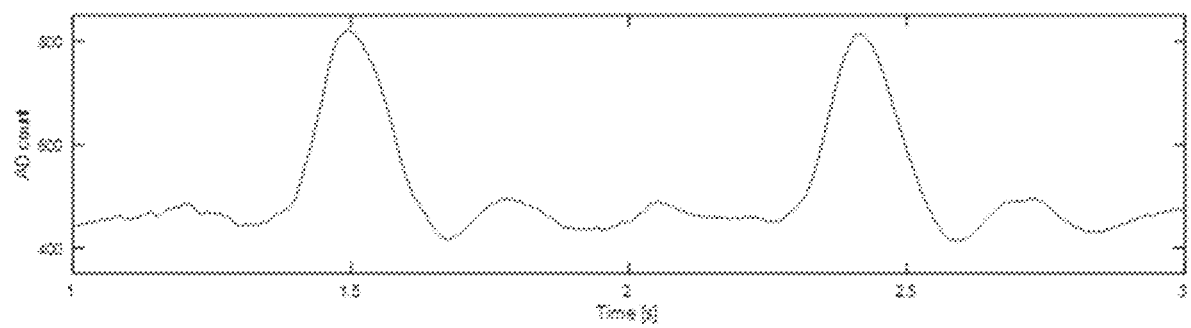
FIGS. 18A and 18B are graphical representations of a user's heartbeat detected using capacitive measurements and PPG measurements.
Figure 18B:
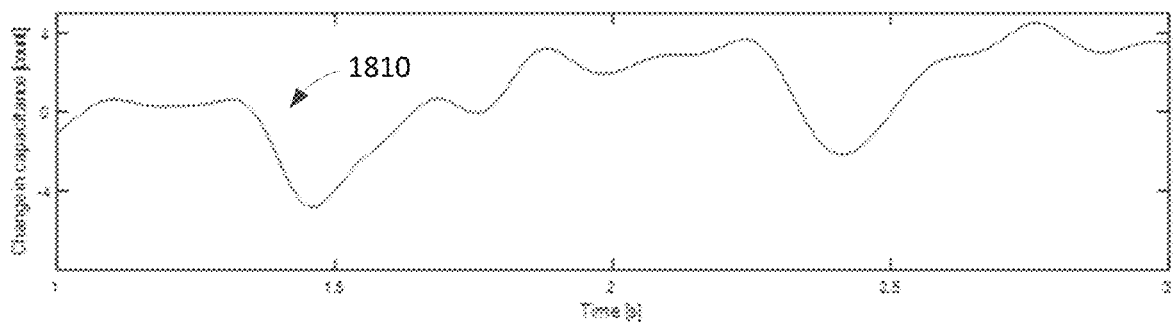

FIG. 18B depicts measured change of capacitance in time as a function of the user's heartbeat. Referring now to FIGS. 3 and 18B in combination, the graph shows a continuous-time signal 1810 that represents a sequence of two distinct heartbeats around 1.5 s and 2.4 s as seen from PPG in FIG. 18A. When the pressure wave, or pulse, propagates through blood vessels in the user's hand, the amplitude of the signal 1810 decreases sharply to a valley (or negative peak) value (i.e., capacitance) due to change in capacitance measurements of the body tissue for one or more of the portions 21-23. Then, once the pressure wave subsides, the amplitude of the signal 1810 increases and returns to a steady-state value. This process occurs two times in the signal 1810, and the distance between adjacent valley (or negative peak) values represents the time lapse between heartbeats that can be used to determine heart rate. Here, the distance between adjacent valleys is 0.95 seconds, so the user's heart rate is 63.16 beats per minute.

In addition to heart rate, the change in capacitance that occurs for each heartbeat may be used by control logic 40 to assess condition of blood vessels in the user's hand. Specifically, if the blood vessels contain a substantial amount of calcium deposits, the change or pattern of change (e.g., slope of change) in capacitance may be different compared to blood vessels without calcium deposits. Further, capacitance measurements that occur after the pressure wave (that is, pulse) has left blood vessels in the user's hand may be used by control logic 40 to assess condition of capillaries and overall health of the user's vascular system.

Figure 28:
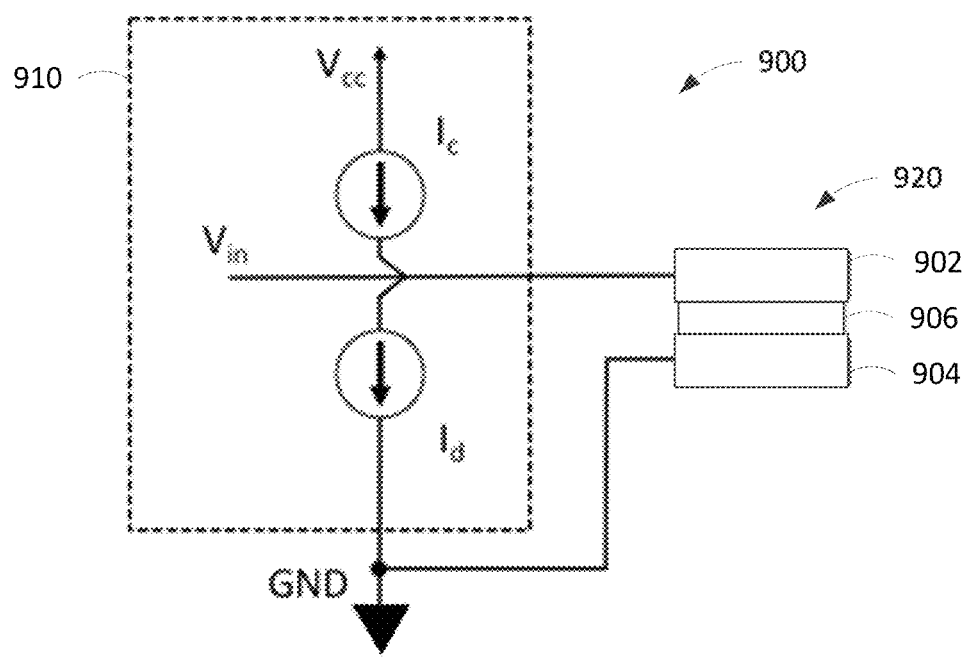
FIG. 28 depicts an embodiment of a capacitance measurement system.

In other embodiments, capacitive sensors 20 can be used to measure other physiological parameters (e.g., blood pressure or respiration rate) in addition to heart rate. One reason for using capacitive sensors 20 to measure physiological parameters is that capacitance sensing consumes significantly less power than optical sensors typically used for the monitoring of vital signs. FIG. 28 shows an embodiment of a capacitance measurement system that can be used with an embedded microcontroller. The capacitance measurement system 900 can include a controller 910 connected to a sensor 920 having pair of electrodes 902, 904 with dielectric material 906 between the electrodes 902, 904. The controller 910 can convert the measured capacitance from the sensor 920 to a digital signal on one or more pins of the controller 910. In one embodiment, the controller 910 can be a Cortex-M4 microcontroller MK20DX256VLH7 that can measure capacitance on 12 pins. However, other microcontrollers with other configurations can be used in other embodiments.

Figure 29:
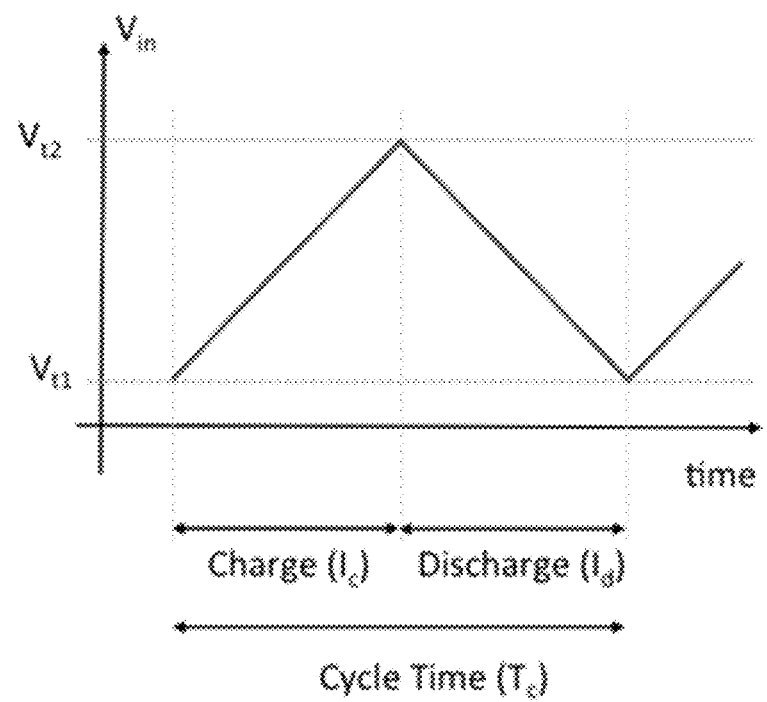
FIG. 29 is a graph of the change of voltage used during capacitance measurement with the capacitance measurement system of FIG. 28.

The controller 910 can include a sensor interface that has constant current sources, symbolically represented as $I_c$ (charging current) and $I_d$ (discharging current). In operation, the use of constant current sources causes a linear increase of the voltage on the sensor 920 (capacitor) during charging and a linear decrease of the voltage on the sensor 920 (capacitor) during discharging, as shown in FIG. 29. Voltage on the capacitive sensor 920 is monitored by the controller 910. Charging (from $V_{t1}$) by current source $I_c$ stops when the input voltage ($V_{in}$) reaches threshold $V_{t2}$. When $V_{t2}$ is reached, discharging by current source $I_d$ is activated. When the input voltage ($V_{in}$) reaches threshold $V_{t1}$, the process starts again. The total time of the charging/discharging cycle is represented as $T_c$ which can correspond to frequency based on the equation $F_c = 1/T_c$.

Voltage on the sensor 920 (capacitor) at relative time t from the beginning of the cycle is shown by:

$$V_c = 1/C \int_0^t I(t)dt$$

for a constant current (i.e., $I_c = I_d = I$). The voltage change during charging can be:

$$V_{t2} - V_{t1} = IT_c/2C$$

and $T_c$ is a function of I and C (capacitance associated with the sensor 920). In one embodiment, the capacitance cycle time and cycle frequency can be controlled by changing the charging/discharge current.

Figure 30:
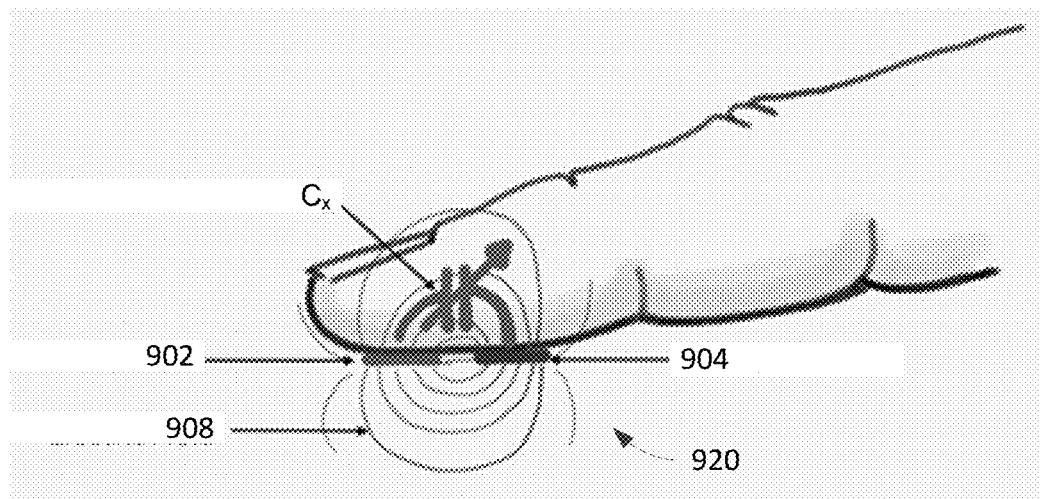
FIGS. 30-33 depict different embodiments of a capacitive sensor from the capacitive measurement system of FIG. 28.

The capacitive sensor 920 can be used to detect physiological parameters of a user by sensing changes in the dielectric constant of the tissues of the user. Physiological processes (e.g., heart pumping, breathing, change of tonus of blood vessels and blood pressure, sweating, and/or a change of balance of hormones) create a change in the dielectric constant or relative permittivity (εr) in the tissues of the user. As shown in FIG. 30, two sensor electrodes 902 and 904 of capacitive sensor 920 can generate an electric field 908 that passes through the tissue (e.g., finger) of the user. Changes in relative dielectric constant of the tissue can change the capacitance between the two electrodes 902, 904. Since the measured capacitance between electrodes 902, 904 represents the sum of the capacitance of the electrodes 902, 904 without contact with the tissue and the equivalent capacitance of the tissue ($C_x$) in proximity of the electrodes 902, 904, physiological changes associated with the user can modify the total capacitance between the electrodes 902, 904 measured by the controller 910. In an embodiment, the equivalent tissue capacitance $C_x$ can be frequency dependent. The controller 910 can change the charging and/or discharging current to adjust cycle frequency $F_c$, as described above. By changing the cycle frequency, as well as the sensor configuration, the changes of capacitance caused by physiological changes (e.g., pulsatile blood flow) can be amplified for easier detection and processing.

In another embodiment, capacitive sensor 910 can be used for in-vivo analysis of body tissues as a replacement for bioelectrical impedance analysis due to the sensor's small size, galvanic isolation, and adjustable frequency. The ability to have an adjustable scanning frequency in the sensor can permit application and condition specific monitoring of tissue properties, such as detection of malignant tissues.

Figure 31:
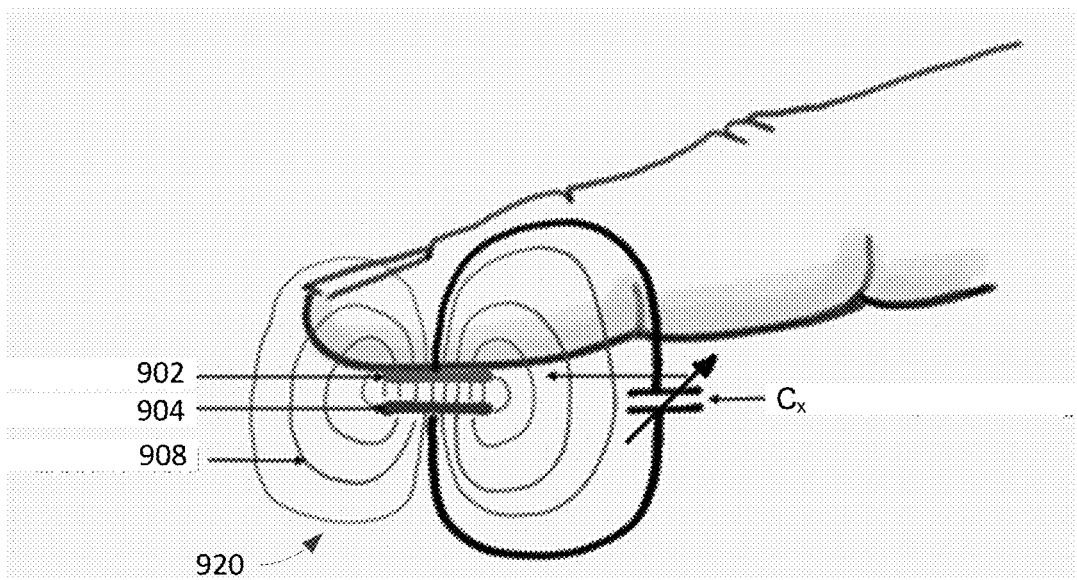
Figure 32:
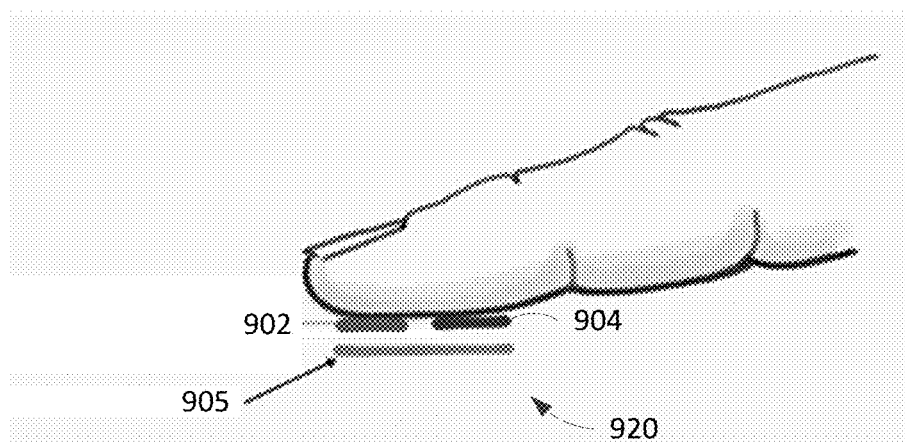
Figure 33:
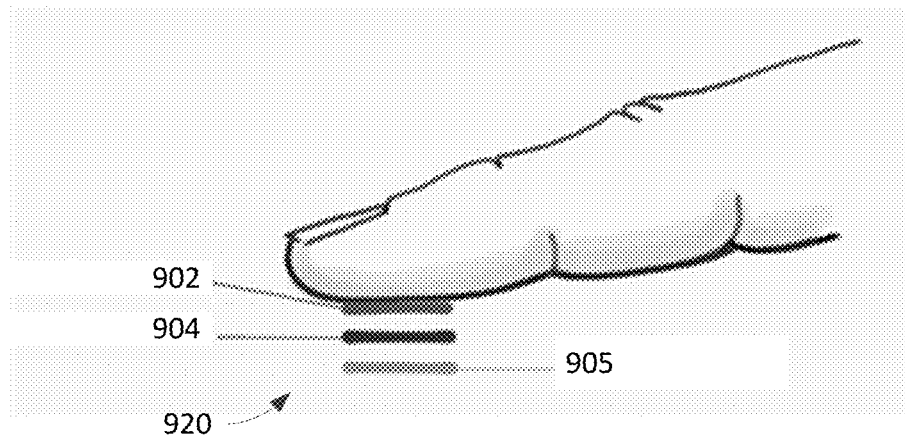

In a further embodiment as shown in FIG. 31, the electrodes 902, 904 can be positioned in a "stacked" or vertical arrangement in place of the "side-by-side" or horizontal arrangement of electrodes 902, 904 shown in FIG. 30. In another embodiment, the electrodes 902, 904 can be configured to conform to the body tissue of the user (e.g., have a curved portion to accommodate a curved portion of the body tissue. The electric field 908 shown in FIG. 31 is also influenced by the dielectric constant of the tissue of the user. The equivalent measured capacitance from sensor 920 can reflect physiological changes of the tissue of the user and be used to measure physiological parameters of the user. In further embodiments as shown in FIGS. 32 and 33, the sensors 920 shown in FIGS. 30 and 31 can be shielded with a shield 905 positioned opposite the tissue (e.g., finger) of the user (or under the electrodes 902, 904 as shown in FIGS. 32 and 33). The shield 905 can reduce noise and improve the quality of the signal provided by the sensor 905. In one embodiment, the sensor shield 905 can be implemented as a solid conductive plate of one or more conductive materials (e.g., copper), a conductive mesh of one or more conductive materials, or other shielding patterns formed from conductive materials.

Figure 34:
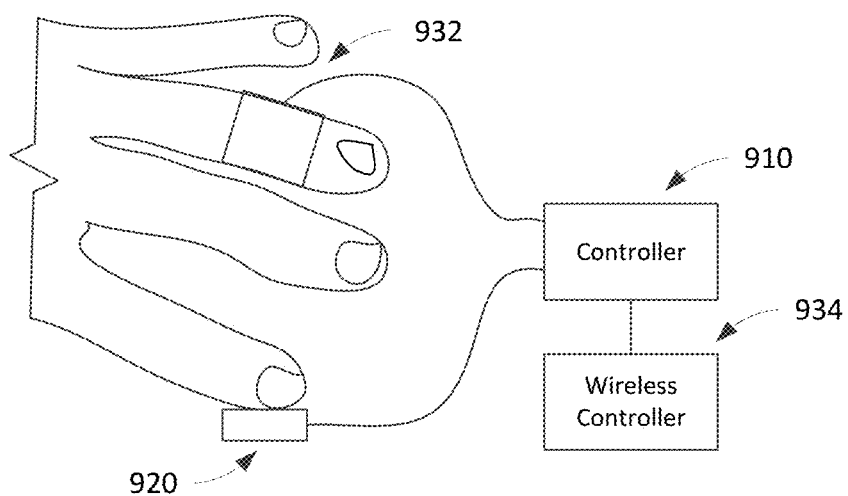
FIG. 34 depicts an experimental validation arrangement for the capacitance measurement system of FIG. 28 using a PPG sensor and providing exemplary results as presented in FIGS. 18A and 18B.
Figure 35A:
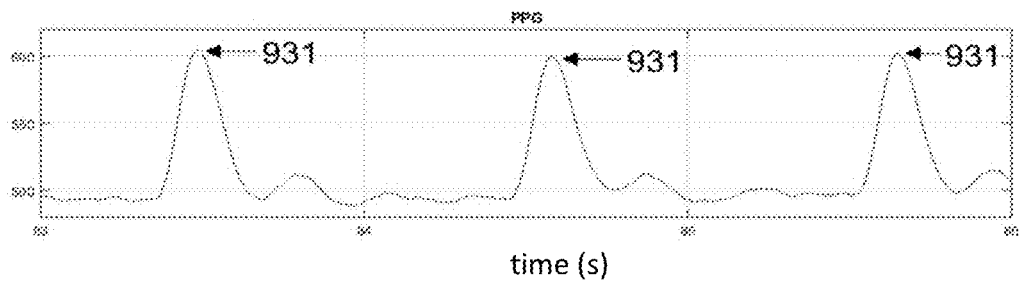
FIGS. 35A-35C are graphs of the PPG, raw capacitance and processed outputs from the capacitive sensor and the PPG sensor from the experimental arrangement of FIG. 34.
Figure 35B:
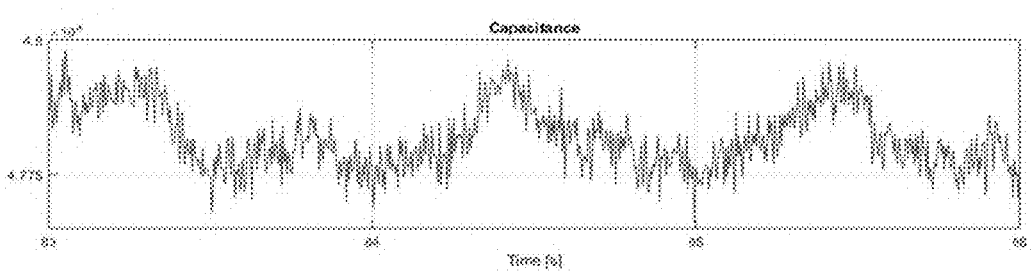
Figure 35C:
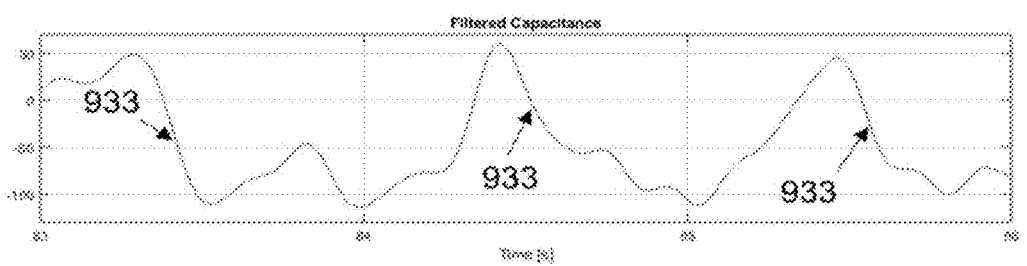

FIG. 34 shows an exemplary experimental arrangement to confirm the operation of the capacitive sensor 920 for detecting physiological parameters of a user. Reference heart activity is recorded using a photoplethysmographic sensor (PPG) 932 positioned on the ring finger. The capacitive sensor 920 is in contact with the index finger and galvanically isolated from the user. The controller 910 uses a capacitance to digital conversion to measure the capacitance from the capacitive sensor 920. The controller 910 can be coupled to a wireless controller 934 to transmit the raw (see FIG. 35B) and processed (see FIG. 35C) capacitance signals to a workstation (not shown) for archiving and visualization. FIG. 35A shows a graph of the outputs from the PPG sensor 932 and FIG. 35C shows the filtered dynamic component of the signal from capacitive sensor 920 for a period corresponding to 3 heartbeats. As seen in FIGS. 35A and 35C, for each detected heart beat (corresponding to peaks 931) from the PPG sensor 932, there is a change in capacitance (corresponding to the negative slopes and valleys 933) from the capacitive sensor 920. Therefore, based on FIG. 35C, decreases in capacitance larger than the dynamically determined threshold from the capacitive sensor 920 can correspond to heartbeats of a user and can be used to detect physiological parameters of the user without the need for a PPG sensor 932.

Figure 36:
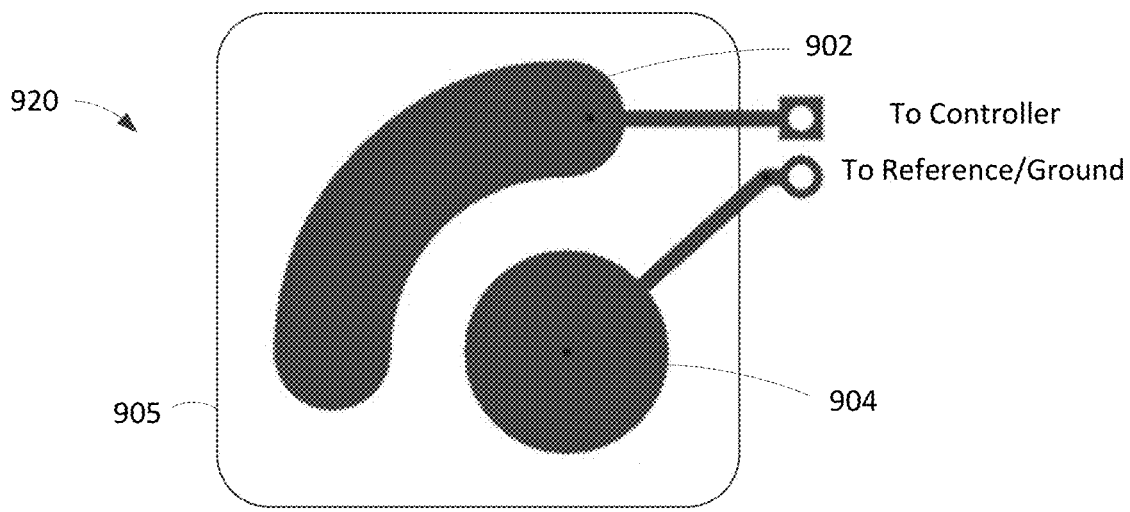
FIGS. 36 and 37 show different embodiments of the capacitive sensor of FIG. 32.
Figure 37:
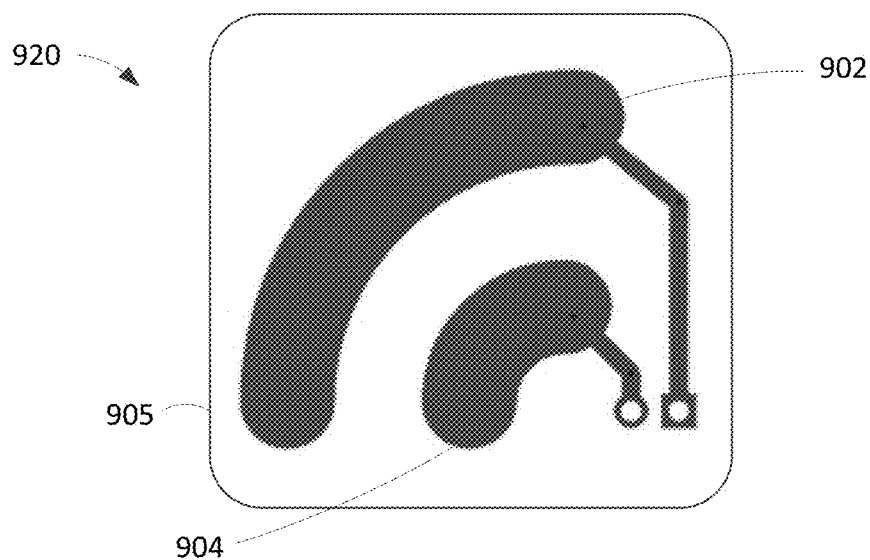

FIGS. 36 and 37 show two different embodiments of the capacitive sensor from FIG. 32. As shown in FIG. 36, the capacitive sensor 920 can include a first electrode 902 having an arcuate shape and a second electrode 904 having a circular shape. The first electrode 902 and the second electrode 904 can be positioned on shield 905 and the first electrode 902 can at least partially surround the second electrode 904. The first electrode 902 can be connected to the controller 910 to provide a signal corresponding to a capacitance measurement to the controller 910. The second electrode 904 can be connected to ground or other reference node. In one embodiment, the second electrode 904 can be connected to a ground terminal of the controller 910. The capacitive sensor 920 shown in FIG. 37 can have a similar arrangement to the arrangement shown in FIG. 36 except that the second electrode 904 can have an arcuate shape instead of a circular shape. In other embodiments, the first electrode 902 and the second electrode 904 of the capacitive sensor 920 can have any suitable shape (e.g., solid circle, ellipse, rounded rectangle, etc.) and/or can be arranged in any suitable pattern on the shield 905. In a further embodiment, the size and/or arrangement of the capacitive sensor 920 can be based on the location of the tissue of the user being used to monitor physiological parameters. For example, the monitoring of physiological parameters of a user on a finger of the user requires the capacitive sensor 920 to have a size that correspond to the tip of the finger or finger of the user.

Figure 38:
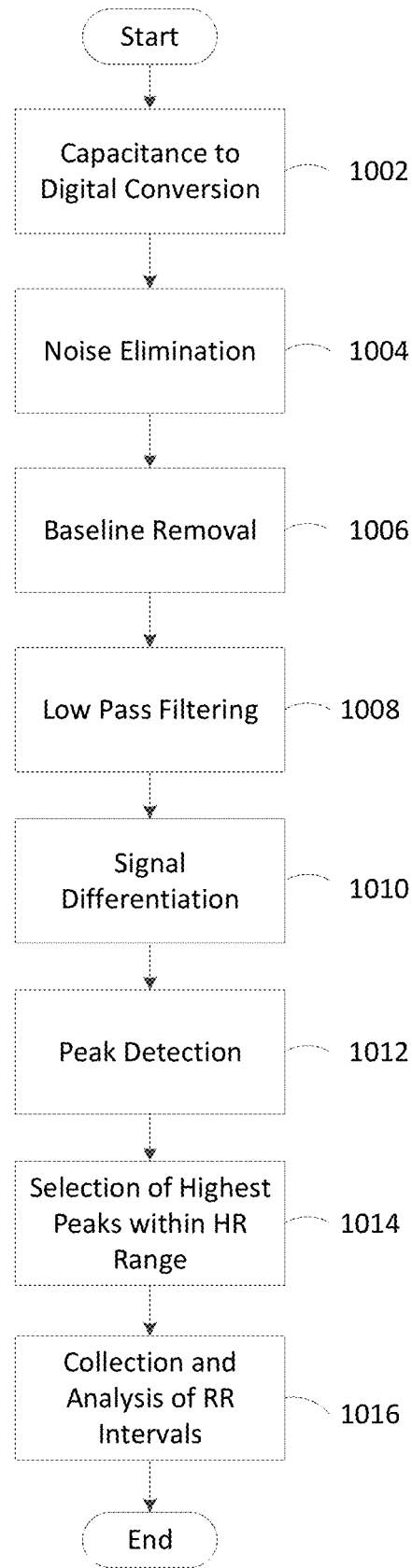
FIG. 38 is a flow diagram for an embodiment of a process for determining physiological parameters of a user with a capacitive sensor.
Figure 42A:
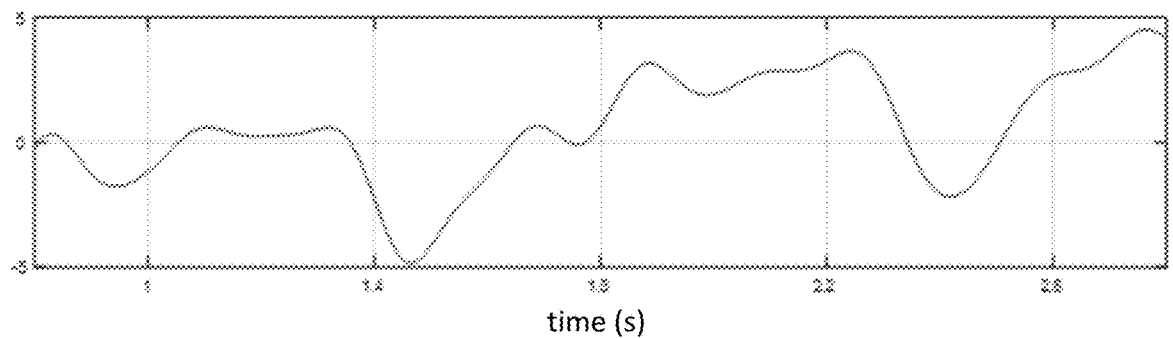
FIGS. 42A-42C are graphs of exemplary signals from different steps of the process of FIG. 38.

FIG. 38 shows an embodiment of a process for determining physiological parameters with signals from a capacitive sensor. The process begins with the measured capacitance signal from the capacitive sensor 920 being provided to the controller 910 and converted to a digital signal corresponding to a numerical value that can be processed by one or more algorithms on the controller (step 1002). Noise in the digital signal can be removed (step 1004) by using a low pass filter and/or downsampling (e.g., reducing the sampling rate) of the digital signal. The baseline of the digital signal can then be removed (step 1006) by subtracting the value of the first sample in the processing window. In other embodiments, the baseline may be removed by subtracting a mean value of all samples in the processing window, eliminating the linear trend of data in the processing window or by using other suitable baseline elimination techniques. The digital signal can then be filtered with a low pass filter (step 1008) as shown in FIG. 42A. In one embodiment, the filter can be a low pass FIR filter with a cut-off frequency in the range of the second harmonic of the maximum heart activity (approximately 5-8 Hz). In another embodiment, wavelet filtering can be used to eliminate or remove noise and/or the baseline and filter the signal.

Figure 42B:
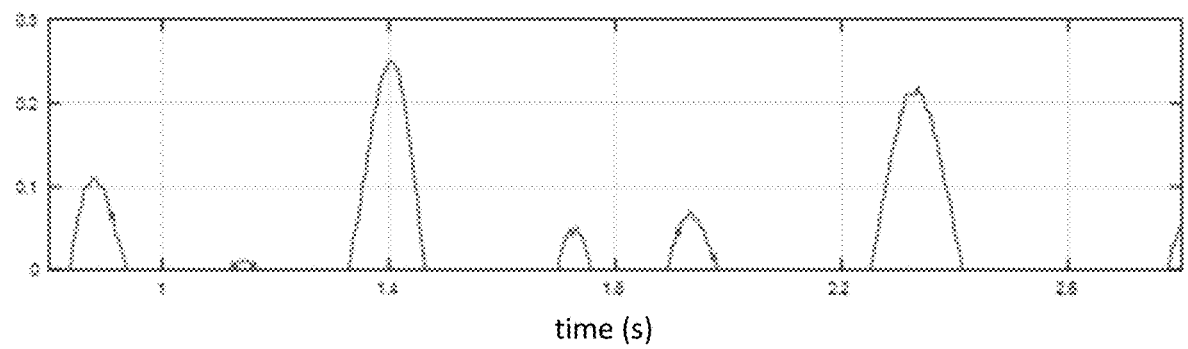
Figure 42C:
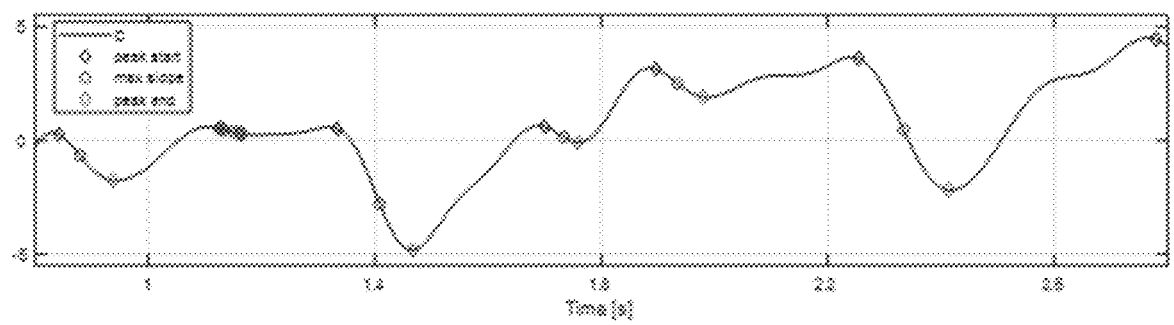

Signal differentiation is then performed on the digital signal (step 1010) to obtain a differential signal and select only negative slopes of the signal. The absolute value of the signal from signal differential and the selection of negative slopes is shown in FIG. 42B. Peaks in the differential signal are then detected (step 1012). In an embodiment, the differential signal can be searched for positive and negative peaks in the original signal as a series of positive or negative differentials in order to detect heart beats and eliminate any dependence on the baseline variation. Peak candidates are selected based on the height and width of the peaks in the original signal. Final peaks are selected according to their intensity and physiological expected range (or heart rate (HR) range) of the signals (step 1014). Peak candidates are shown in FIG. 42C with marked beginning, end, and maximum of each candidate peak. For the threshold of 0.15 of signal differentials (see FIG. 42B) only two peaks are selected in the window with maximum slope at $t_1$=1.4 s and $t_2$=2.3 s, that is correlated with corresponding peaks in a PPG signal at 1.5 and 2.4 s (see FIG. 18A). The time difference between the peaks is 2.3-1.4=0.9 s that is equivalent to 66.6 beats per minute (i.e., 60 s/0.9 s). Once the peaks have been selected, an analysis of the inter-beat (RR) interval can be performed (step 1016). With a sufficient number of RR intervals, an analysis of heart rate variability (HRV) can be performed. HRV analysis provides an assessment of the autonomous nervous system and can be correlated with the stress level of the user. In another embodiment, a Fast Fourier Transform (FFT) or wavelet spectral analysis can be used to assess average frequency of the heart activity in the processing window.

Figure 39:
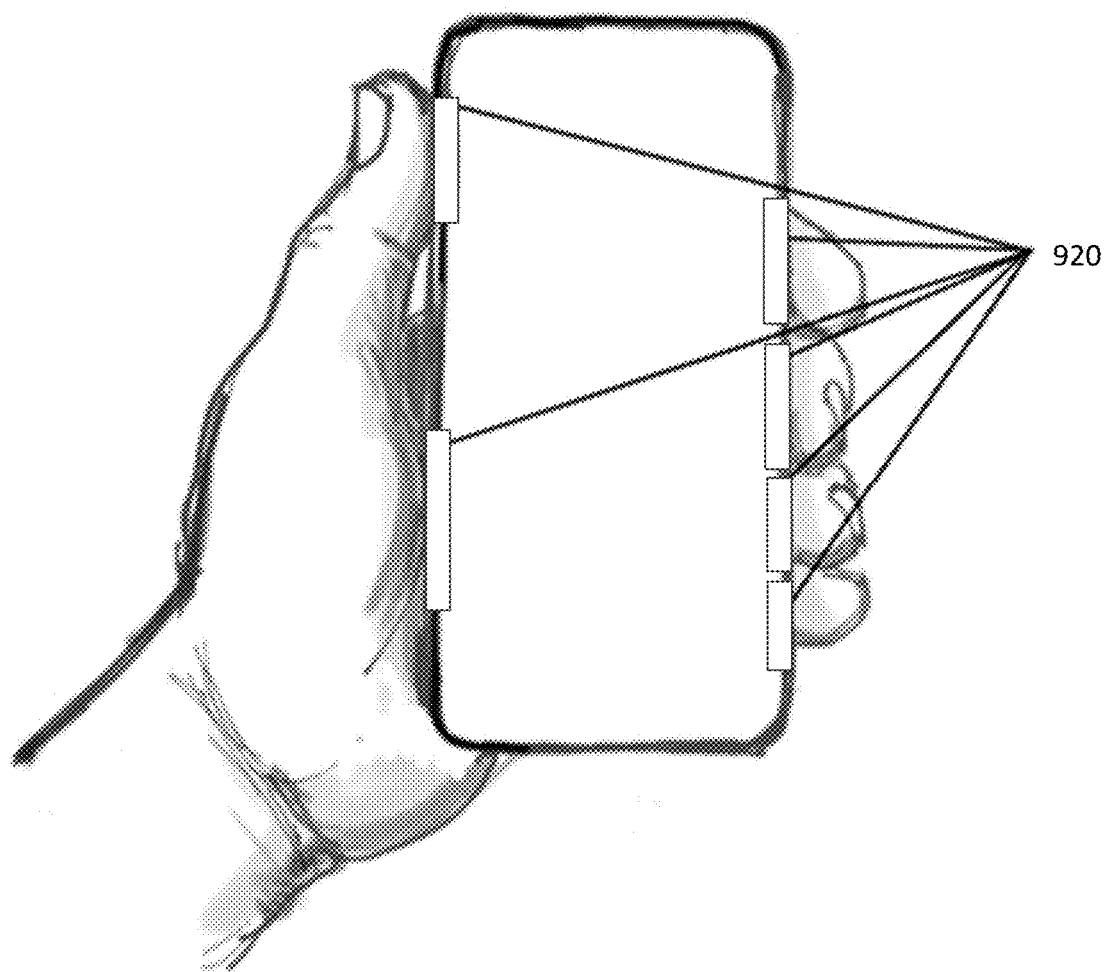
FIG. 39 depicts an embodiment of a device with multiple capacitive sensors.

In one embodiment, system performance can be improved by using multiple capacitive sensors 920 (e.g., capacitive sensors 920 under multiple fingers) to achieve more robust sensing and noise elimination. FIG. 39 shows an embodiment of a smartphone or smartphone case with multiple capacitive sensors. As shown in FIG. 39, the smartphone or smartphone case can have capacitive sensors 920 positioned to be in contact with the fingers and palm of the hand of a user holding the device in order to monitor the heart activity of the user.

In another embodiment, a slow variation of the change of the capacitance signal from the capacitive sensor 920 can be used to assess the respiration of the user. Further, the detected breathing rate from a user and changes in the user's RR intervals could be used to assess the function of the autonomous nervous system of the user by using changes in heart rate variability (HRV) and respiratory sinus arrhythmia (RSA) that represents change of RR intervals caused by breathing. In addition, changes in the HRV of the user can be used to assess the stress of the user.

Figure 43A:
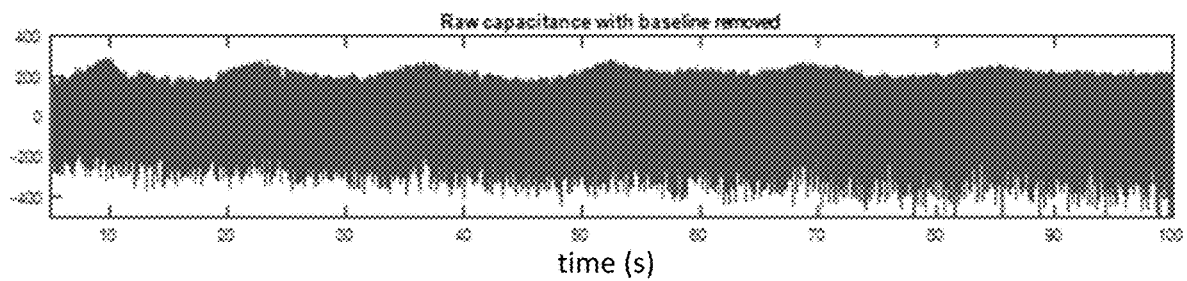
FIGS. 43A-43D are graphs of exemplary signals associated with the process of extracting a breathing signal from capacitance.
Figure 43B:
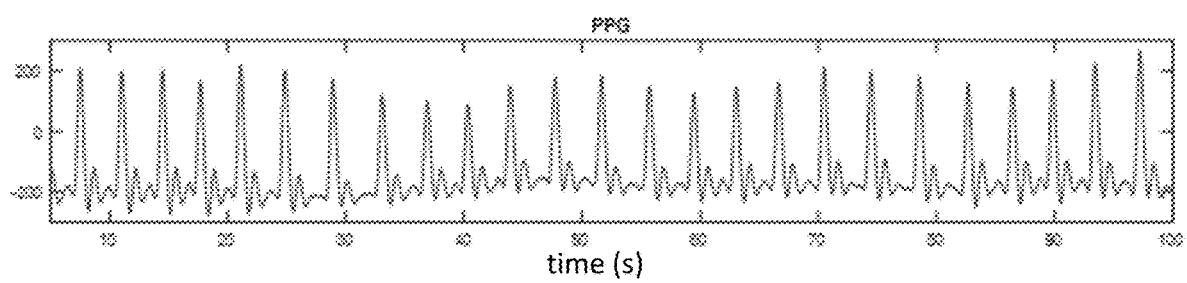
Figure 43C:
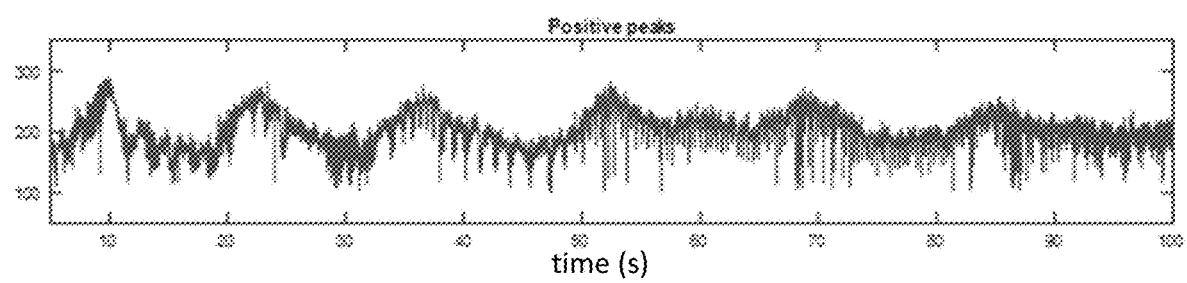
Figure 43D:
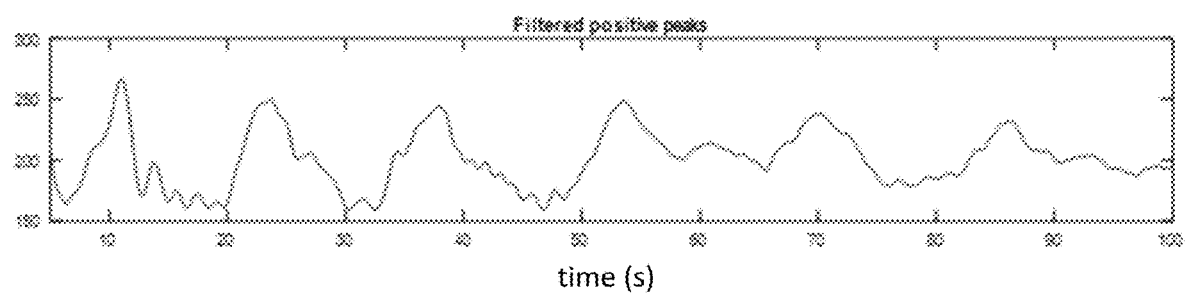
Figure 44:
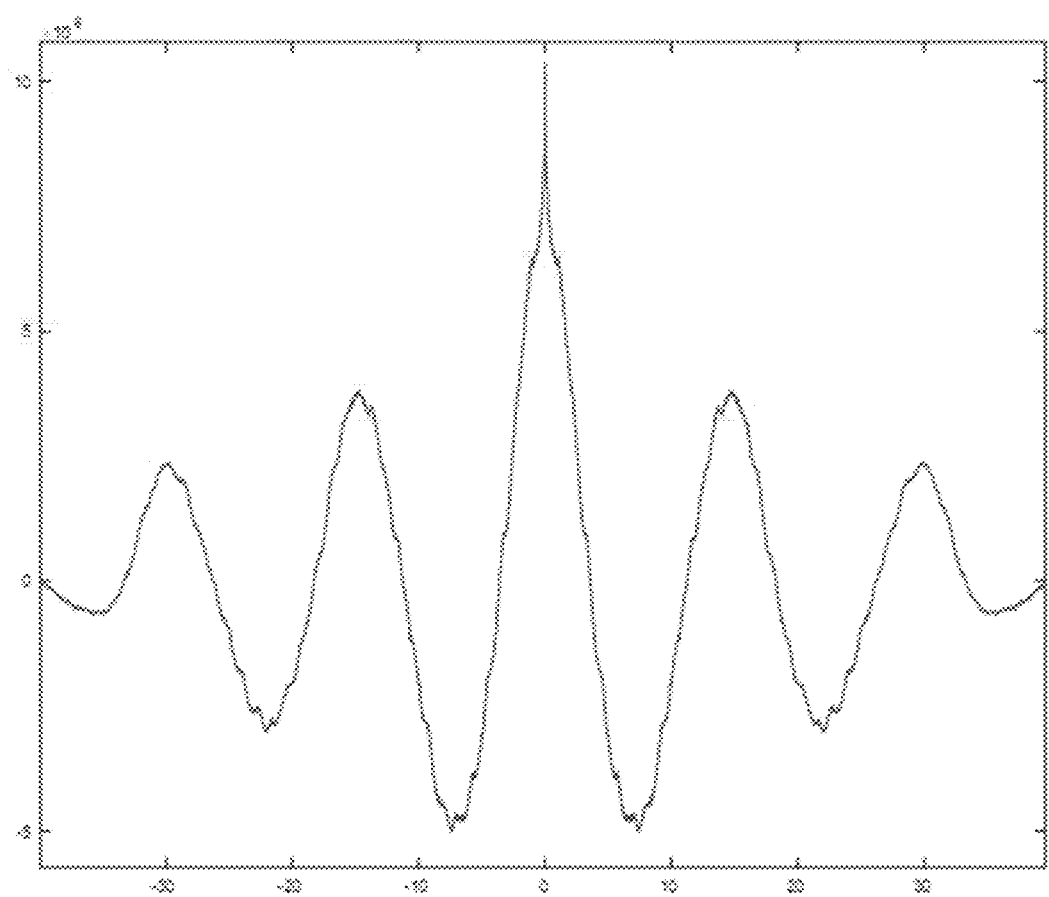
FIG. 44 is a graph of an autocorrelation of the 40 second window from the signal of FIG. 43C.

FIGS. 43A-43D represent signals associated with the process of extracting a breathing signal from capacitance measurements. Raw capacitance from the sensor with the baseline removed is shown in FIG. 43A. A corresponding PPG signal used as a reference signal is shown in FIG. 43B. The positive peaks of the raw capacitance from FIG. 43A are shown in FIG. 43C and the low pass filtered output of the signal from FIG. 43C is shown in FIG. 43D. During recording, the subject used very slow paced breathing at approximately 5 breaths per minute. Individual breaths can be identified as maximums or minimums of the filtered signal in FIG. 43D. Alternatively, breathing periods can be identified by positive or negative zero crossings of the detrended filtered signal in FIG. 43D. For example, a single breath can be identified from the maximums of the filtered signal at times 11.2 s and 23.7 s. The time difference between the maximums represents the breath duration, in this example 23.7 s−11.2 s=12.5 s, that is equivalent to 4.8 breaths per minute (i.e., 60 s/12.5 s). In another embodiment, spectral analysis or autocorrelation of the window of samples could be used to measure breathing period and determine breathing rate. FIG. 44 shows an autocorrelation of the 40 second window of the signal from FIG. 43C. Autocorrelation represents the similarity of the signal with the same signal with the time lag. Peaks of autocorrelation represent self-similarity of the delayed signal and can be used to find the fundamental frequency of the signal. For the signal in FIG. 43D, the first peak of autocorrelation is at time 14.3 s, which represents the fundamental period of the periodic signal, and in this example, the respiration period. Therefore, the average respiration rate in the given time window of 40 s was 4.2 breaths per minute (i.e., 60 s/14.3 s).

Figure 19:
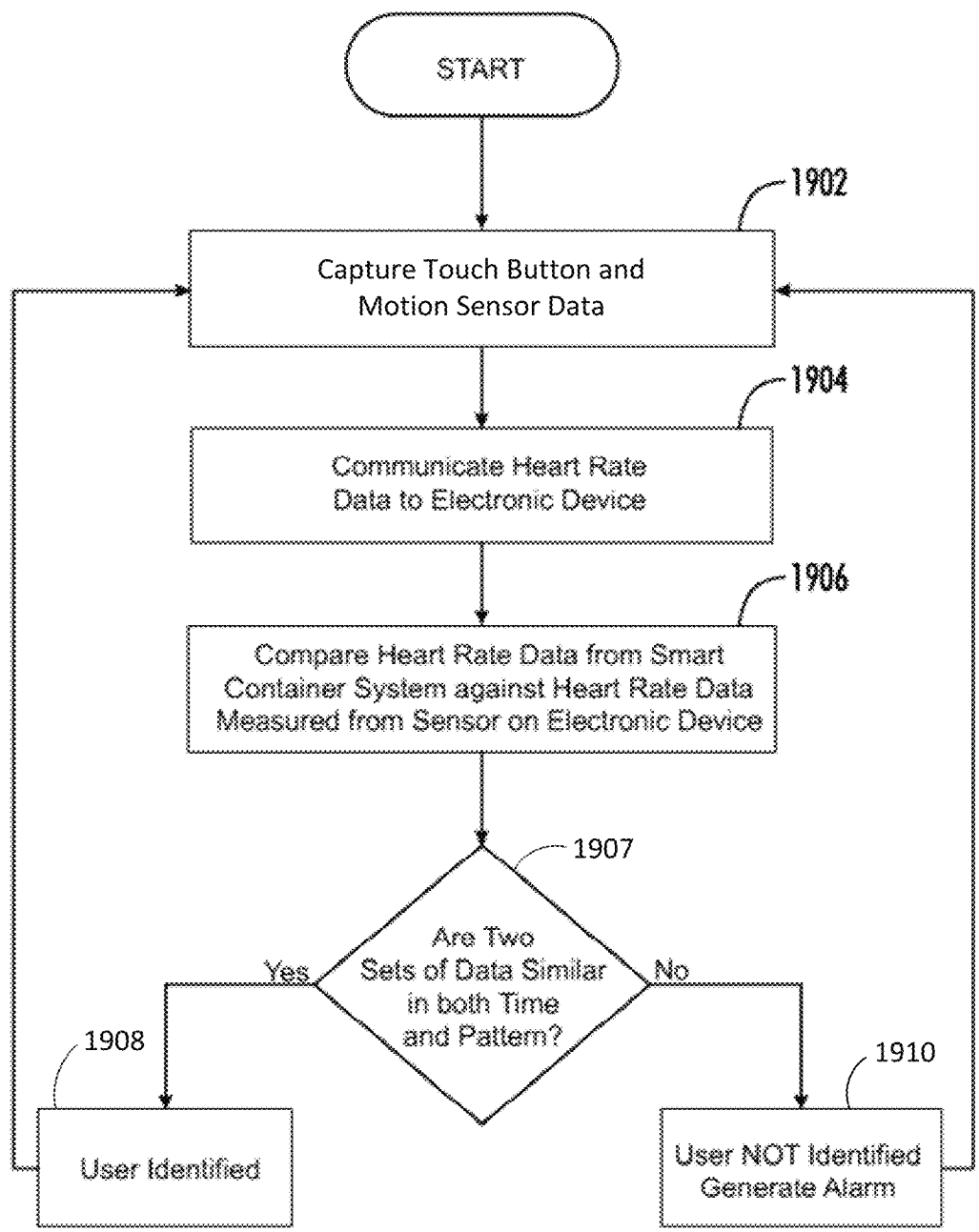
FIG. 19 depicts an exemplary method for verifying identity of a user handling a smart container system based on the user's heart rate.

FIG. 19 depicts a process for identifying a user of an object (e.g., the smart container system 800) based on data indicative of the user's heart rate. Referring now to FIGS. 3, 4, 19 and 41 in combination, at step 1902, control logic 40 receives data from a capacitive sensor (e.g., capacitive sensor 920 or capacitive sensor 20) and/or motion sensor 33 indicating handling of the smart container system 800 or object 10. Next, at step 1904, control logic 40 communicates data indicative of the user's heart rate from the capacitive sensor to electronic device 70 via the communication interface 42. In other embodiments, data indicative of a user's heart rate may be provided by an optical sensor 37 in addition to or in place of the capacitive sensor.

Figure 41:
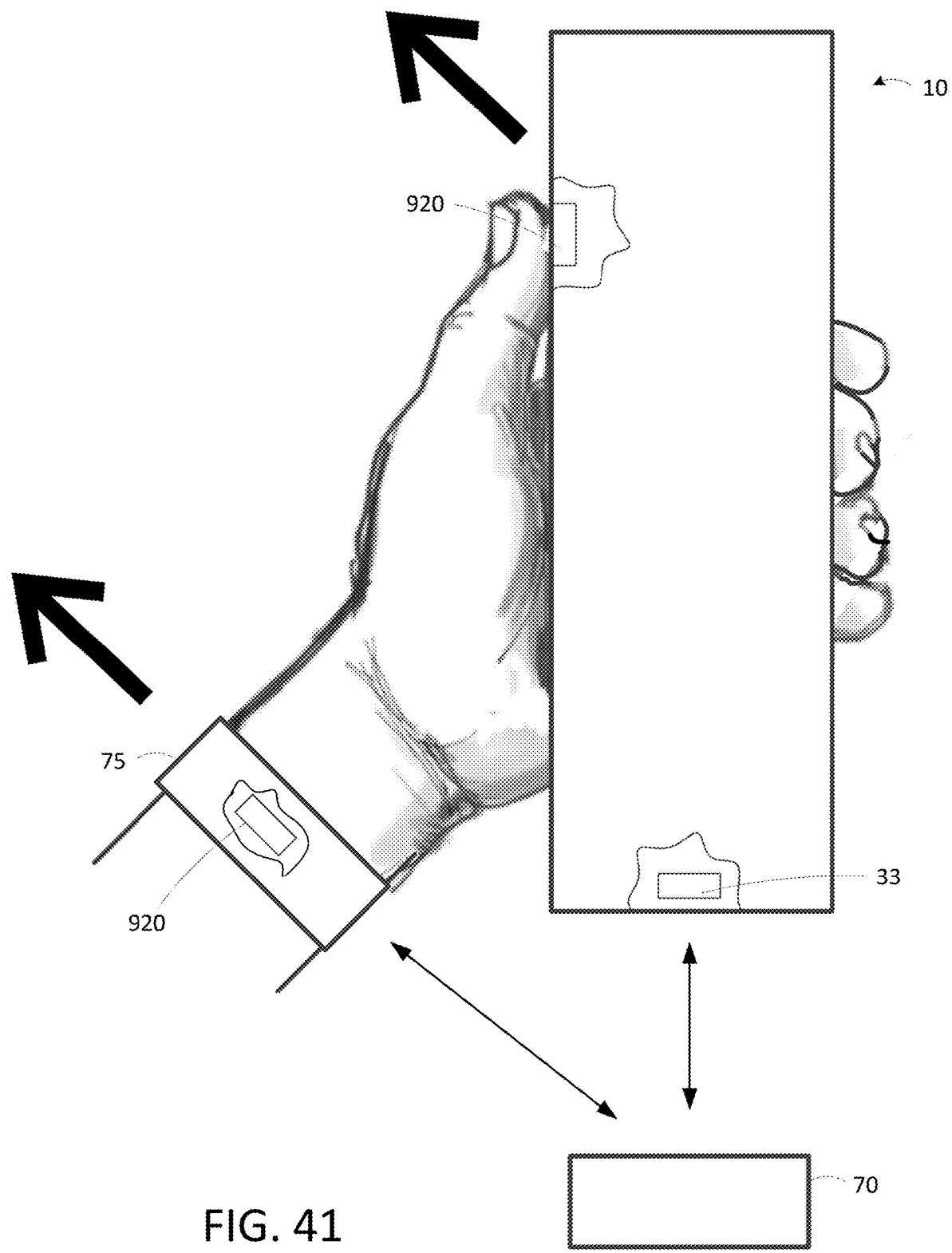
FIG. 41 depicts an embodiment of an arrangement associated with the methods for identifying a user in FIGS. 19 and 20.

Then, at step 1906, electronic device 70 compares data related to heart rate (that is, capacitance measurements) from the capacitive sensor or optical sensor 37 of the smart container system 800 or object 10 against similar data collected from a pulse oximeter (not shown) or capacitive sensor (e.g., capacitive sensor 920 or capacitive sensor 20) of a wearable device 75 (see FIG. 41) on the user. In one possible embodiment, the wearable device 75 could be a smart watch with an integrated pulse oximeter and/or capacitive sensor that can communicate with the electronic device 70 either directly (as shown in FIG. 41) or through the server 60. At step 1907, if the heart rate data from the capacitive sensor of the object 10 and the heart rate data from the capacitive sensor or pulse oximeter of the wearable device 75 closely match or exactly match one another in both pattern and time, then the process proceeds to step 1908. Otherwise, the process proceeds to step 1910.

At step 1908, the electronic device 70 identifies the user by confirming that the user of the smart container system 800 or object 10 matches the person associated with the wearable device 75. Next, return to step 1902 and wait until control logic 41 receives data from the motion sensor 33 indicating motion of the smart container system 800 or object 10 or if it is requested by an external program.

At step 1910, the electronic device 70 confirms that the user of the smart container system 800 or object 10 does not match the person associated with the wearable device 75, and generates an alarm or notification on display of same and/or user interface 12 of the smart container system 800 or object 10. The same notification can be sent to the server 60 and/or the electronic device 70. Next, return to step 1902 and wait until control logic 41 receives data from the capacitive sensor and/or motion sensor 33 indicating handling or motion of the smart container system 800 or object 10. In one embodiment, the wearable device 75 and the electronic device 70 can be a single device that is worn by the user.

Figure 20:
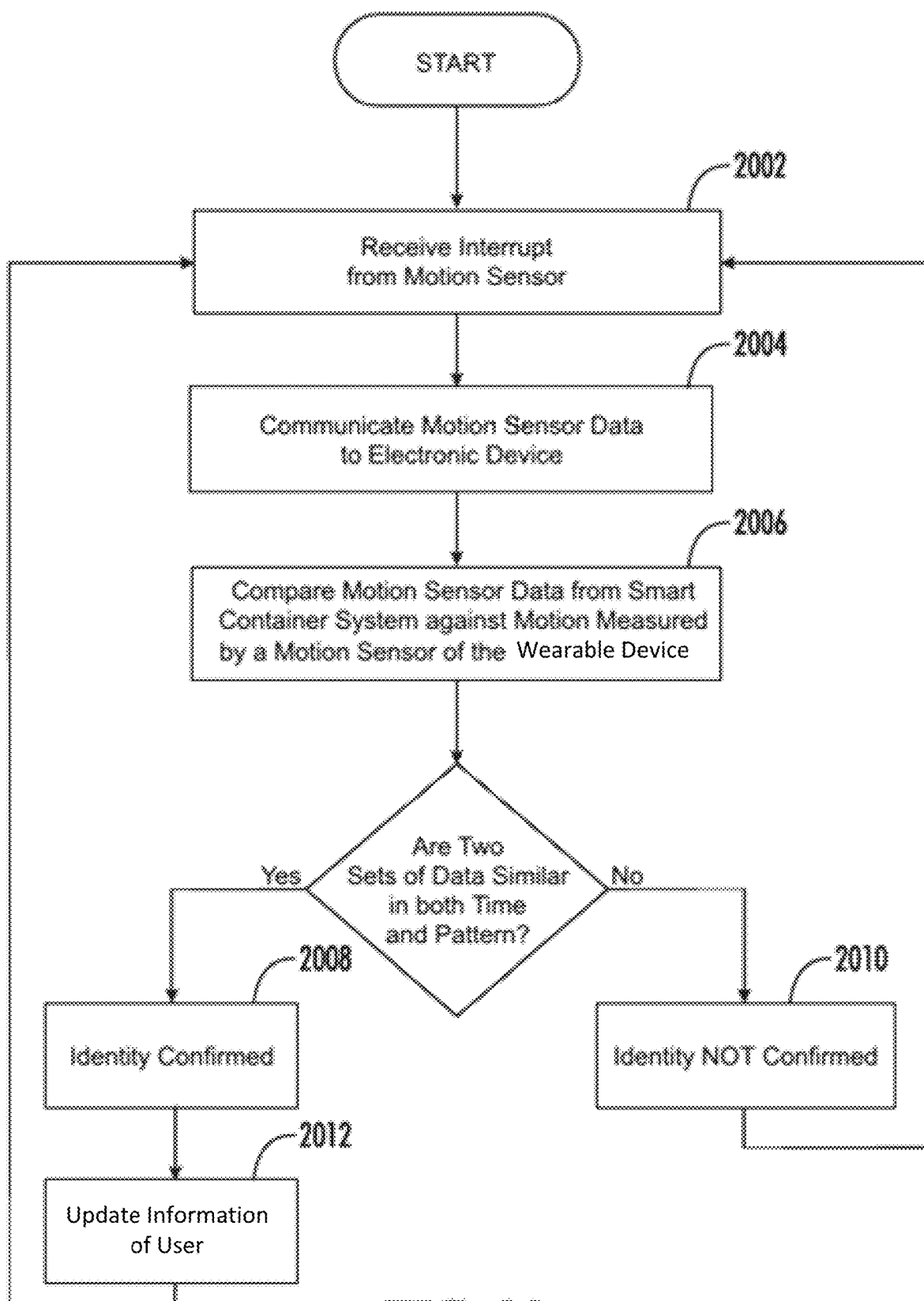
FIG. 20 depicts an exemplary method for verifying identity of a user consuming liquids from a smart container based on motion sensor data.

FIG. 20 depicts steps 2000 for identifying a user of an object (e.g., the smart container system or a smartphone) based on data from motion sensor 33. Referring now to FIGS. 3, 4, 20 and 41 in combination, at step 2002, the processing module 24 receives a signal from motion sensor 33 in response to a user handling the object 10 (e.g., consuming a liquid if the object 10 includes container 11). Note that, in some embodiments, the processing module 24 may, prior to receiving the signal, be in a sleep or low-power mode to conserve power. Note also that it is possible for an interrupt (or other event for awakening or otherwise controlling the processing module 24) to be received from other types of sensors, such as a capacitive sensor 20 (FIG. 14), indicating that a user is touching or otherwise manipulating the object.

At step 2004, the processing module 24 transmits motion data received from motion sensor 33 to electronic device 70 via the communication interface 42. Electronic device 70 may be a smart watch or other type of device associated with the owner of the object (e.g., smart container system).

At step 2006, electronic device 70 compares motion sensor data received from the object (e.g., smart container system) against similar motion data from a motion sensor (not shown) on the wearable device 75. As shown in FIG. 41, the wearable device 75 is a separate device from the electronic device 70, but in other embodiments, the wearable device 75 and the electronic device 70 can be a single device. If the motion sensor data from the object (e.g., smart container system) and the motion sensor data from the wearable device 75 closely match or exactly match one another in both pattern (e.g., acceleration and/or orientation angle) and time, then proceed to step 2008. Otherwise proceed to step 2010.

At step 2008, the electronic device 70 confirms that the user handling the object or consuming liquid from container 11 matches the person associated with the wearable device 75. Next, proceed to step 2012, and update information (e.g., the hydration profile) of the user.

At step 2010, electronic device 70 confirms the user handling the object or consuming liquid from container 11 does not match the owner of wearable device 75. The electronic device 70 can issue a warning (e.g., an audible noise or a displayed message) to the user to notify the user that another person is handling the object or attempting to use the smart container system. In another embodiment, the electronic device 70 may instruct the object (e.g., smart container system) to issue a warning to notify the unknown user handling the object that the unknown user's handling of the object is not authorized. Next, the process returns to step 2002 and waits until the processing module 24 receives another interrupt from motion sensor 33 in response to a user handling the object. In one embodiment, the electronic device 70 may transmit information about an unknown user to the server 60.

At step 2012, electronic device 70 requests, from the processing module 24, data associated with the user (e.g., liquid consumption data) and updates information associated with the user (e.g., a hydration profile of the user). For example, the electronic device 70 can provide liquid consumption data to a hydration monitoring program that adjusts user's daily target of liquid consumption based on the amount of liquid just consumed. Note that, in some embodiments, the hydration monitoring program may be located on another device, such as a smart phone. In this case, electronic device 70 communicates data directly to the other device via a wireless communication link (e.g., WiFi, 4G, LTE, Bluetooth, etc.). Alternatively, electronic device 70 may communicate liquid consumption data to server 60, and monitoring logic 62 may be used to communicate data to the other device (that is, user's smart phone). Next, return to step 2002 and wait until the processing module 24 receives another interrupt from motion sensor 33 or other sensor in response to a user handling the object (e.g., consuming liquid from container).

Figure 21:
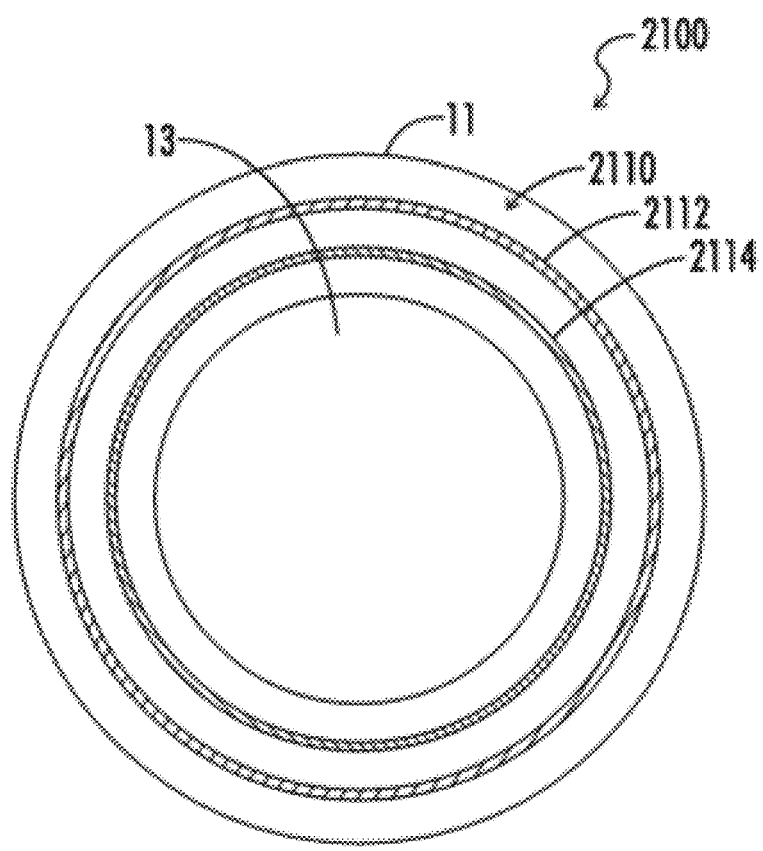
FIG. 21 depicts an exemplary embodiment of a smart container system having a capacitive sensor on a rim of a container to detect opening and closing of a lid.

FIG. 21 depicts another exemplary embodiment of a smart container system 2100. Specifically, FIG. 21 shows a top view of the smart container system 2100, including a capacitive sensor 2110 located on an exterior surface of the rim of container 11. Referring now to FIGS. 3 and 21 in combination, the capacitive sensor 2110 includes a pair of electrodes 2112 and 2114 that are electrically connected to the processing module 24 via the capacitive interface 44. The processing module 24 receives capacitance measurements from the capacitive sensor 2110, and control logic 40 detects opening or closing of a lid (not shown) for the smart container system 2100 based on changes in capacitance of the capacitive sensor 2110. As an example, when the lid is closed and completely covers the rim of container 11, capacitance of the capacitive sensor 2110 changes by at least a threshold amount, and control logic 40 determines, based on this change in capacitance, that the lid is closed. Likewise, when the lid is removed and no longer covers any portion of the rim of container 11, capacitance of the capacitive sensor 2110 changes back by at least the threshold amount, and control logic 40 determines, based on this change in capacitance, that the lid has been removed. Note that, in some embodiments, the interior face of the lid may include a dielectric material to increase the change in capacitance that occurs when the lid is closed and completely covers the rim of container 11.

Figure 22:
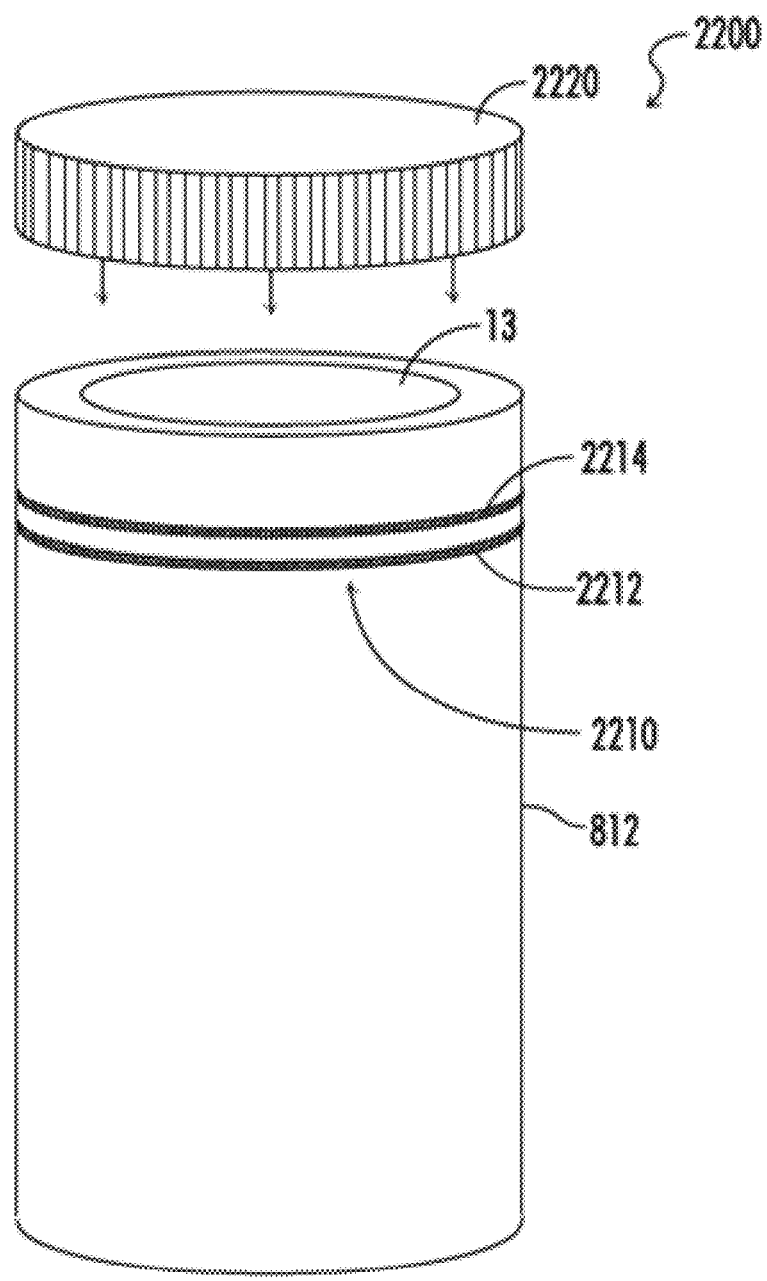
FIG. 22 depicts an exemplary embodiment of a smart container system having a capacitive sensor on the outer container to detect opening and closing of a lid.

FIG. 22 depicts yet another exemplary embodiment of a smart container system 2200 in which a capacitive sensor 2210 is used to detect opening and closing of a lid 2220 for the smart container system 2200. Specifically, FIG. 22 shows a perspective view of the outer container 812 with electrodes 2212 and 2214 of the capacitive sensor 2210 positioned on an exterior surface of the outer container 812 near the opening 13. Thus, when closed, the lid 2220 protrudes down far enough along the exterior surface of the outer container 812 to completely cover the capacitive sensor 2210 and create a change in capacitance by at least a threshold amount (e.g., a rubber seal in lid 2220 and in contact with capacitive sensor 2210 would increase capacitance approximately seven times). Likewise, when removed, the lid no longer covers any portion of the exterior surface of outer container 812, and capacitance of the sensor 2210 changes back by at least the threshold amount.

Figure 23:
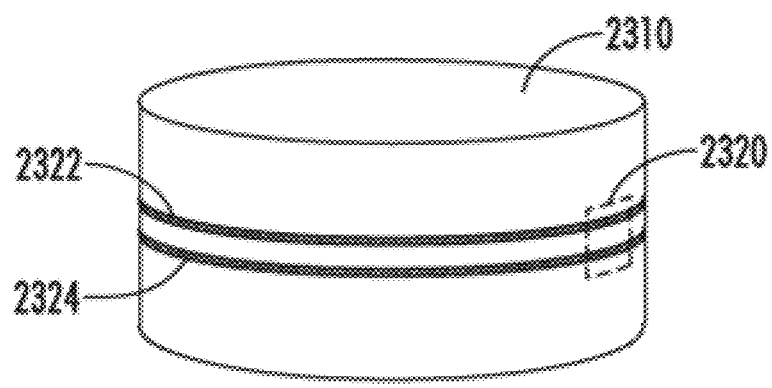
FIG. 23 depicts an exemplary embodiment of a smart container system having a capacitive sensor in the lid.

FIG. 23 depicts an embodiment of a lid 2310, which may be used with a smart container system, such as the one shown by FIG. 8 or FIG. 22. Such lid 2310 may be screwed or otherwise attached to the outer container 812. The lid 2310 includes a capacitive sensor 2320 to detect opening or closing of the lid 2310. Referring now to FIGS. 3 and 22 in combination, electrodes 2322 and 2324 of the capacitive sensor 2320 are positioned along either the inner or outer wall of the lid 2310, and communicate capacitance measurements to the processing module 24, which is located within the interior portion of the lid 2310. The processing module 24 receives capacitance measurements via the capacitive interface 44, and control logic 40 determines, based on changes in capacitance by at least a threshold amount, opening or closing of the lid 2310. As an example, when closed, the inner wall of the lid 2310 contacts a portion of the exterior surface of outer container 812 near opening 13, and creates a change in capacitance by at least the predetermined amount. Further, upon removal, the inner wall of the lid no longer contacts any portion of the exterior surface of outer container 812, and capacitance changes back by at least the predetermined amount. Note that, in some embodiments, the exterior surface of outer container 812 may include a dielectric material to increase the change in capacitance of capacitive sensor 2320 that occurs when the lid 2310 is closed.

Additionally, capacitance measurements of the capacitive sensor 2320 may change by at least a threshold amount when a user grips the lid 2310 to open or close same. Thus, control logic 40 can, based on changes in capacitance by at least the threshold amount, detect a user handling the lid 2310 and, from this, determine the user is likely about to consume all or a portion of the liquid in container 11.

Figure 24:
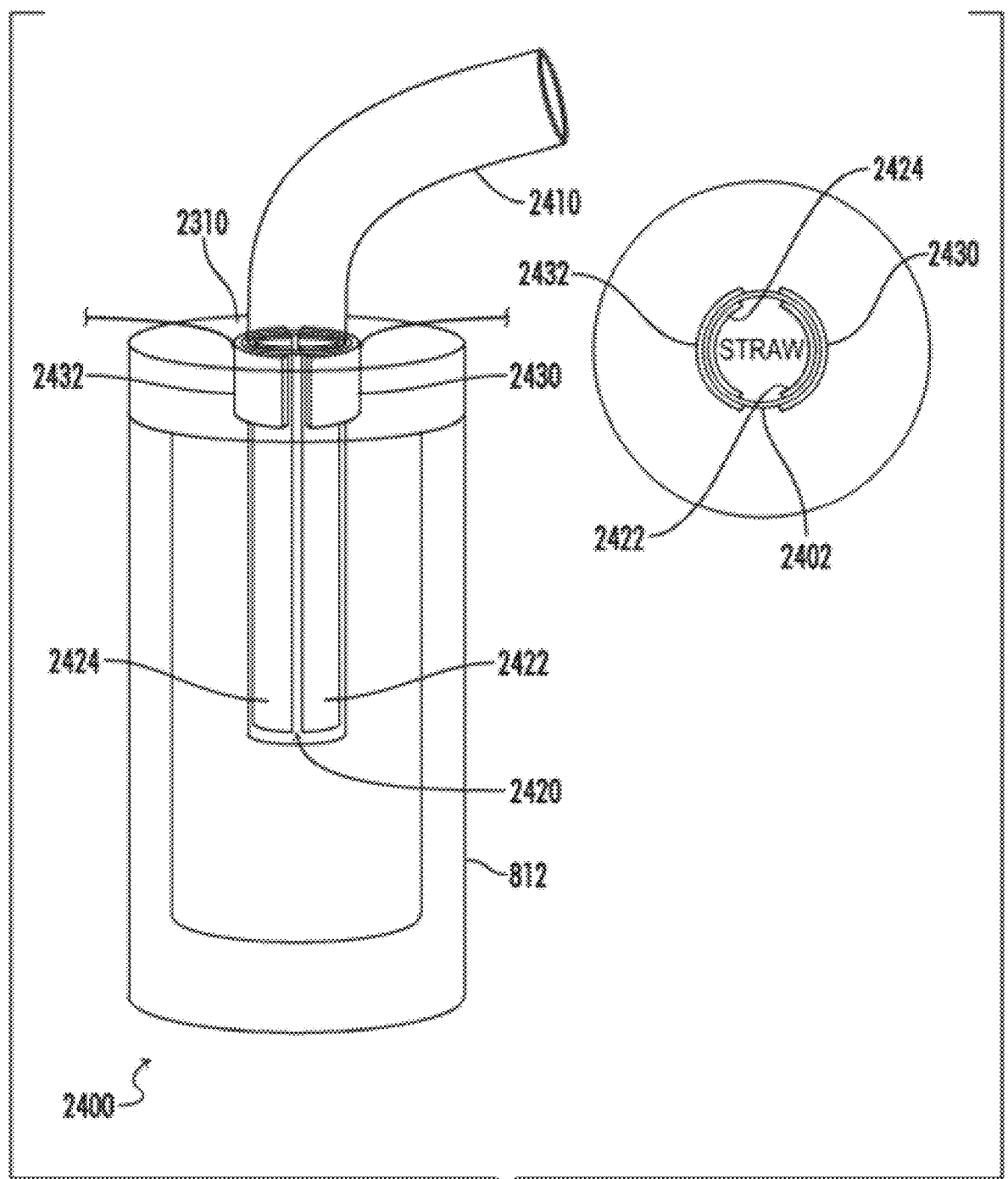
FIG. 24 depicts an exemplary embodiment of a smart container system having a straw that includes a capacitive sensor to measure volume of liquid.

FIG. 24 depicts an embodiment of a smart container system 2400 in which the lid 2310 of FIG. 23 includes an aperture 2402 for a straw 2410 to pass therethrough and extend down into the interior of container 11. Referring now to FIGS. 3 and 24 in combination, the straw 2410 includes a capacitive sensor 2420 having electrodes 2422, 2424 preferably embedded in or otherwise positioned on the straw 2410. The lid 2310 includes a pair of capacitive plates 2430, 2432 electrically connected to the processing module 24 via the capacitive interface 44. Each capacitive plate 2430, 2432 surrounds a portion of the aperture 2402, and allows for non-contact measurements of the capacitive sensor 2420. As an example, capacitance measurements of the capacitive sensor 2420 may be used by control logic 40 to determine volume of liquid in the container 41. Further, control logic 41 may be programmed to generate a notification when, based on changes in capacitance, the volume of liquid falls below a predetermined amount. The notification may be an audible or visual alarm emitted by or displayed on the user interface 12. Still further, since electronics are contained within the straw 2410 and the lid 2310, the user can remove the lid 2310 and clean the container 11 after each use. Further, since the capacitive sensor 2420 is embedded in or otherwise positioned on the straw, the user can wash it or remove and wash it after each use as well.

Figure 25:
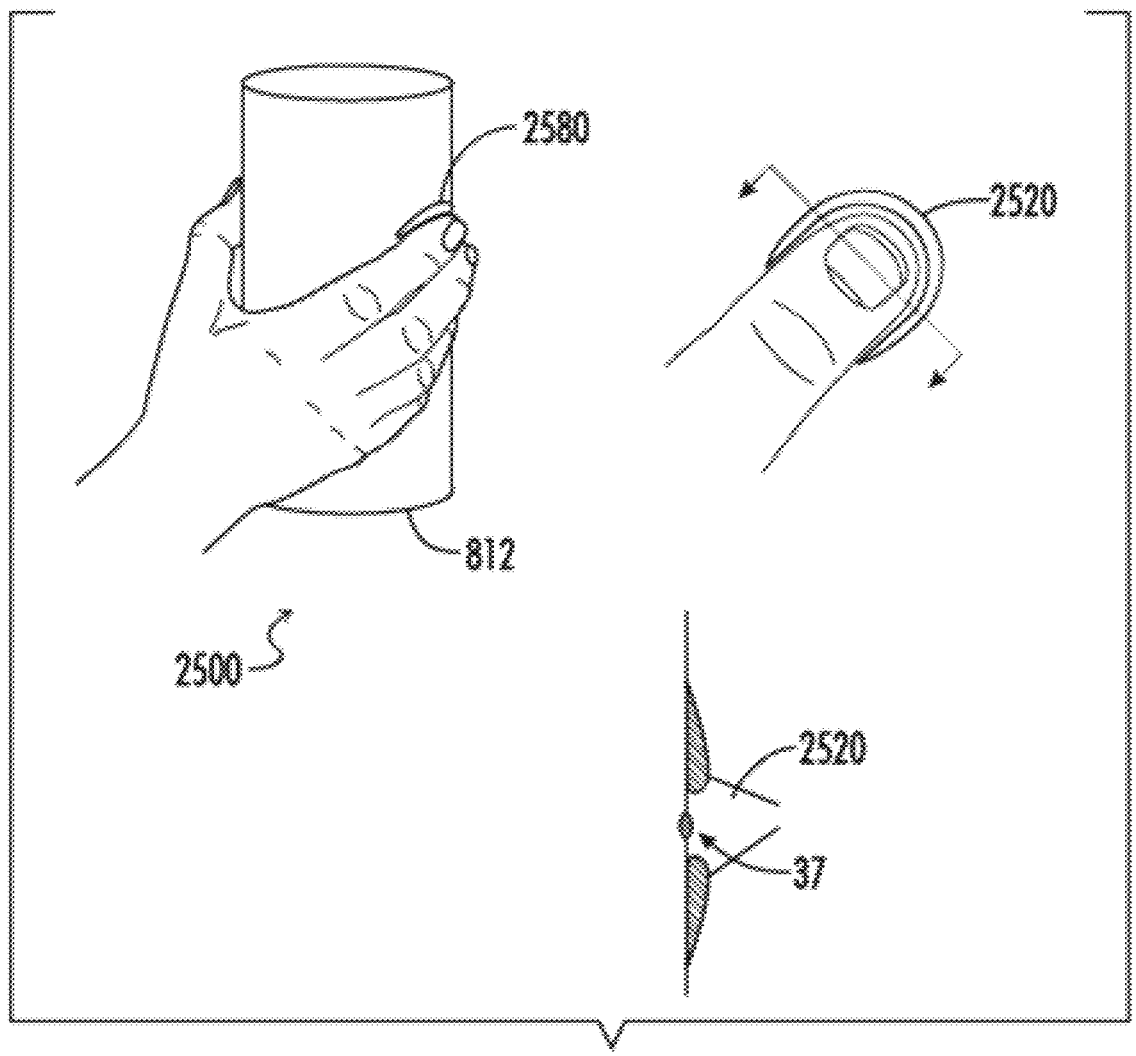
FIG. 25 depicts an exemplary embodiment of a smart container system having an optical sensor to detect physiological parameters of a user handling the smart container system.

FIG. 25 shows an exemplary embodiment of a smart container system 2500 in which an optical sensor 37, preferably a photoplethysmography sensor, is used to measure physiological parameters (e.g., heart rate) of the user handling the smart container system 2500. Referring now to FIGS. 3, 4, and 25 in combination, the optical sensor 37 is one of sensors 14, and communicates with the processing module 24 via the sensor interface 45. In one embodiment, the optical sensor 37 is located within a concave groove 2520 on the exterior surface of the outer container 812, wherein the concave groove 2520 is made sufficiently wide and sufficiently long in order to accept at least a portion of the user's finger. Thus, when a user grips the outer container 812 and inserts the distal end of a finger in the concave groove 2520, the optical sensor 37 illuminates the skin of user's finger with a light emitting diode (not shown) and then measures the amount of light either transmitted or reflected to a photodiode, also known as photoplethysmogram or PPG, (not shown). Further, based on the intensity and amount of light measured by the photodiode, the optical sensor 37 can detect changes in blood volume that occur for each heartbeat. In an embodiment, the light emitting diode can be a red, green or infrared light emitting diode.

In one embodiment, a first optical sensor 37 and a second optical sensor 37 are located within the concave groove 2520, and are separated by a predetermined length. When a user inserts her hand in the groove, both the first and second optical sensor 37 measure data based on the pulse wave that occurs during every cardiac cycle (i.e., heartbeat). Since the two sensors are separated by the predetermined length, data from either the first or second optical sensors 37 will have a time delay or latency relative to data from the other. However, dividing the predetermined length by the time delay yields the pulse wave velocity (PWV) of the blood pulse, which correlates with and can be used to estimate changes of blood pressure of the user. In addition, the interval of the PPG signal from the optical sensors 37 can be used to monitor the stress of the user.

In another exemplary embodiment, data from one or more optical sensors 37 of the smart object 10 is transmitted to an electronic device 70 and compared against similar data collected from a similar sensor on the electronic device 70 (or wearable device 75). Possible examples of an optical sensor on the electronic device 70 or the wearable device 75 could be a smartwatch that measures PPG on the wrist or an earring sensor that measures PPG on the earlobe. With a larger distance (e.g., at least 20 cm) between an optical sensor 37 on the smart object 10 that senses pulses on the tip of the finger and an optical sensor on an electronic device 70 or wearable device 75, PWV may be measured with greater accuracy. Further, if data from the optical sensor 37 of the smart object 10 closely or exactly matches data from the sensor on the electronic device 70 or the wearable device 75 in both time and pattern, then identity of the user can be confirmed based on blood pressure readings.

In another embodiment, multiple capacitive sensors 20 positioned at known distances with respect to a user can be used to measure pulse wave velocity of the blood pulse for each heartbeat of the user and assess the blood pressure (or changes in the blood pressure) for the user according to the changes in pulse wave velocity. For example, a first capacitive sensor 20 associated with a first object held by a user (e.g., a container, smartphone, etc.) can be used to detect a first pulse wave when a finger of the user is placed in contact with the first capacitive sensor 20. A second capacitive sensor 20 associated with a second object worn by a user (e.g., smartwatch, headband, etc.) can be used to detect a second pulse wave (corresponding to the first pulse wave) when the second capacitive sensor 20 is positioned in contact with the user. The two pulse wave determinations can then be used to determine the user's pulse wave velocity, since the distance between the capacitive sensors 20 is known (or can be determined) and the time delay between the first and second pulse waves is known. The blood pressure for the user can then be determined from the pulse wave velocity calculation and the measurements from the first and second capacitive sensors.

Figure 26:
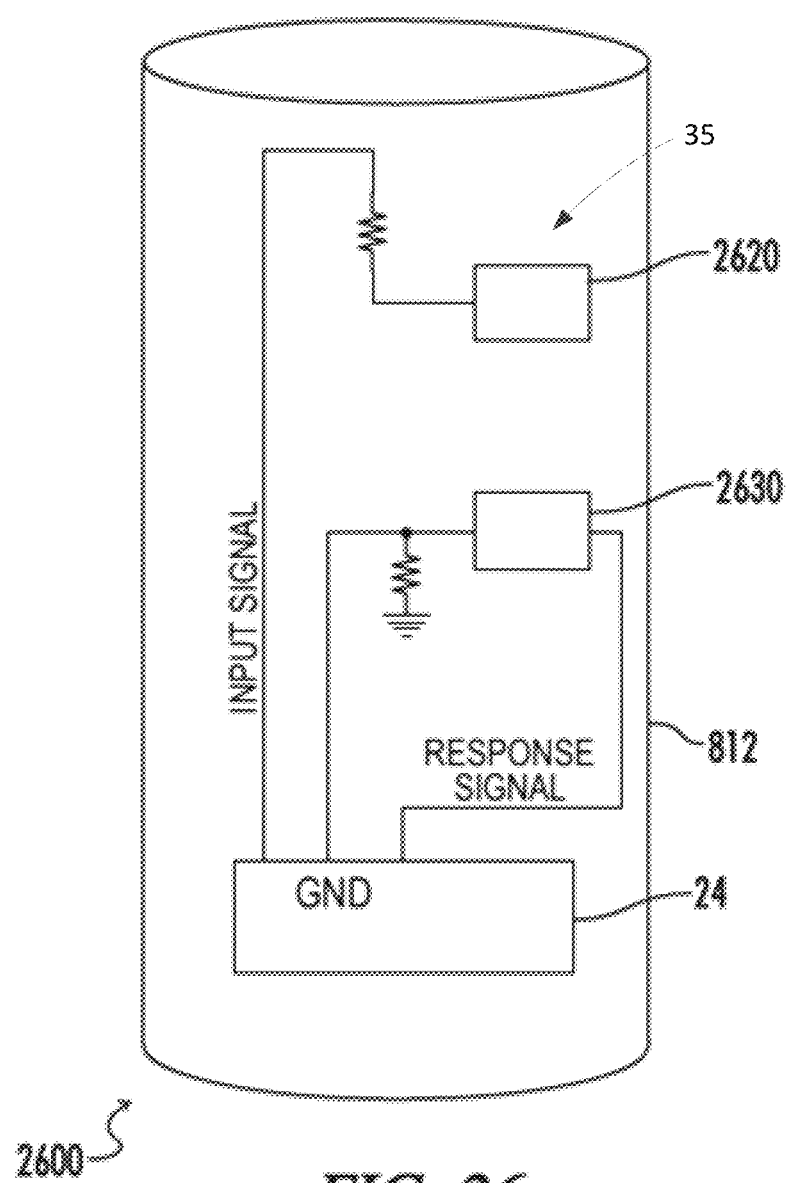
FIG. 26 depicts an exemplary embodiment of a circuit that non-invasively measures emotional response of a user handling the smart container system based on measurements of complex impedance from body tissue in contact with the smart container system.

FIG. 26 depicts an exemplary embodiment of a smart container system 2600 in which a first set of electrodes 2620 and a second set of electrodes 2630 are used to monitor the complex impedance of the skin of the user handling the smart container system 2600. More specifically, FIG. 26 shows one implementation of a circuit that indirectly measures emotional response of a user via changes in the galvanic skin resistance of the user's hand. Referring now to FIGS. 3 and 26 in combination, in one embodiment, a constant voltage or a sinusoidal input signal at a certain frequency is generated by the processing module 24 and propagates from the first set of electrodes 2620 into the skin of user's hand. The second set of electrodes 2630 measures a response signal that is, at least in part, caused by the sinusoidal input, and communicates the response signal to the processing module 24. The response signal represents a voltage divider between resistors R1 and R2 and resistance of the user's hand between electrodes 2620 and 2630. Control logic 40 determines, based on the magnitude of the response signal, a value indicative of the user's complex skin impedance for a given point in time. Changes of skin impedance may be used to monitor a user's emotional response, also known as galvanic skin resistance or GSR. Monitoring of complex impedance at several frequencies can be used to monitor changes in hydration of the user (Lawrence E. Armstrong, "Assessing Hydration Status: The Elusive Gold Standard," Journal of the American College of Nutrition, 2007, pp. 575 S-584 S).

Referring now to FIGS. 3 and 4 in combination, motion sensor 33 of the smart object 10 may be used to monitor hand tremors of a patient suffering from Parkinson's disease or other type of ailment. More specifically, motion sensor 33 can monitor motion of a smart container system or object (e.g., smartphone) each time the patient touches same. Hand tremor data from each event may be stored in memory 41, and periodically uploaded to electronic device 70 or server 60. Using data, an application on the electronic device 70 or server 60 can detect, based on a steady increase in magnitude of hand tremors, that medication is becoming less effective, and generate an alert on the electronic device 70 or user interface 12. Alternatively, the hand tremor data from the motion sensor 33 can be used by the electronic device 70 or the server 60 to detect a decrease in the magnitude of hand tremors indicating that newly prescribed medication is being effective. Further, hand tremor data may also be used by patient's physician to determine when and by how much to increase (or decrease) the daily dosage of medication.

In other embodiments, the capacitive sensor 20 may be incorporated into other objects or devices in addition to container 11. For example, the capacitive sensor 20 can be incorporated into a watch or bracelet worn by a user or into bands worn around the arms and/or legs of a user. In another example, the capacitive sensor 20 can be incorporated into a necklace or an object hanging from the necklace (e.g., a medical alert device or pendant) that is worn by a user, in a head band or hat worn by a user, or in the frame of glasses worn by a user to provide for continuous monitoring of vital signs of the user. The capacitive sensor 20 can be incorporated into a ring for continuous monitoring of heart activity of a user or incorporated into treadmills, elliptical machines, weights, or other exercise equipment to monitor heart rate during exercise by users. The capacitive sensor 20 can be incorporated into the handle of a cane for continuous monitoring of the elderly or injured users. The capacitive sensor 20 may also be incorporated into everyday objects (e.g., cups and glasses, silverware, kitchen utensils, toothbrushes, hairbrushes, etc.) to detect use and vital signs during the handling of the objects by a user.

In further embodiments, the capacitive sensor 20 can be incorporated into a blood pressure measurement cuff for the monitoring of physiological parameters of the user, such as heart rate, while performing a blood pressure measurement on the user. In another embodiment, the capacitive sensor 20 can continuously and non-invasively monitor the blood pressure of infants in situations where blood pressure measurement cuffs could not be used on the infant. The capacitive sensor 20 can be implemented around a fingerprint sensor to detect vital signs of the user during the fingerprint identification process. In addition, the morphology of the pulse received by the capacitive sensor 20 may assist in the identification of the user.

In an embodiment, physiological parameters (or vital signs) detected on multiple objects can be used to identify who is using a particular object at a particular moment in time. For example, a sequence of RR intervals on the smartwatch can be compared with RR intervals on weights in a fitness center to determine the person using the weights. In addition, once the person is identified, the type and intensity of exercise being performed by the person (or user) can be determined. Further, "smart" weights with capacitive sensors 20 can also integrate inertial sensors to determine the number and pace of repetitions being performed by the user during exercise.

In an embodiment, multiple smart objects 10 can be integrated into network 50 and communicate with server 60. The smart objects 10 can provide information to the server 60 regarding the use and/or operation of the smart objects 10. For example, the smart object 10 configured as a smart container can provide information on how much liquid has been consumed from the smart object 10, the last time the smart object 10 was used or handled, and/or the corresponding heart rate, respiratory rate, and/or oxygen saturation in the blood of the user of the smart object 10. A second user (e.g., a healthcare provider) can then access the information for one (or several) smart objects 10 directly from the server 60 and make corresponding evaluations regarding the user of the smart object 10 (e.g., the user needs to hydrate more). In addition, the second user can send alerts or notifications to one or more of the smart objects 10, as needed. In another embodiment, the server 60 can automatically send alerts or notifications to the smart objects 10 when certain data parameters from the smart objects 10 are identified.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

Now, therefore, the following is claimed:

1. A system for monitoring physiological parameters of a user, the system comprising:
    a beverage container to be held by a hand of the user;
    at least one first sensor positioned on an exterior surface of the beverage container to permit a tissue of a hand of a user to contact the at least one first sensor while the beverage container is held by the hand of the user, the at least one first sensor configured to sense at least one parameter indicative of capacitance while the at least one first sensor is in contact with the tissue; and
    at least one processor configured to calculate at least one physiological parameter of the user based on the at least one parameter from the at least one first sensor, the at least one processor further configured to analyze changes in capacitance from the at least one first sensor to determine the at least one physiological parameter.

2. The system of claim 1, wherein the at least one physiological parameter includes at least one of heart rate, respiration rate or inter-beat interval.

3. The system of claim 1, wherein the at least one first sensor comprises a first electrode and a second electrode, the at least one parameter corresponding to the capacitance between the first electrode and the second electrode.

4. The system of claim 3, wherein the first electrode and the second electrode are arranged one of substantially horizontally, substantially vertically, or to conform to a body tissue of the user.

5. The system of claim 3, wherein the at least one first sensor comprises a shield configured to reduce noise in the sensed capacitance, the shield being positioned adjacent at least one of the first electrode and the second electrode and opposite the tissue of the user.

6. The system of claim 1, wherein the at least one processor detects a heartbeat of a user in response to a determination that the capacitance from the at least one first sensor has changed by an amount greater than a dynamically determined threshold.

7. The system of claim 6, wherein the at least one processor determines a heart rate for the user based on the detected heartbeat.

8. The system of claim 1, wherein the at least one processor determines a respiratory rate for the user based on the changes in capacitance.

9. The system of claim 1, further comprising a controller coupled to the at least one first sensor, the controller configured to convert the at least one parameter measured by the at least one first sensor to a digital signal and provide the digital signal to the at least one processor.

10. The system of claim 1, wherein the at least one parameter is at least one first parameter, the system further comprises a wearable device configured to be worn by the user, the wearable device comprising at least one second sensor positioned to contact a tissue of the user when the wearable device is worn by the user, the at least one second sensor configured to sense at least one second parameter indicative of capacitance and the at least one processor configured to calculate at least one physiological parameter of the user based on the at least one second parameter from the at least one second sensor.

11. The system of claim 10, wherein the at least one processor is configured to determine an identity of a user in contact with the beverage container based on the at least one first parameter and the at least one second parameter.

12. The system of claim 10, wherein the at least one processor is configured to determine a blood pressure of a user in contact with the beverage container based on the at least one first parameter from the at least one first sensor and the at least one second parameter from the at least one second sensor.

13. The system of claim 1, wherein the at least one processor is configured to detect handling of the beverage container based on the at least one parameter from the at least one first sensor.

14. The system of claim 1, wherein the at least one parameter is at least one first parameter, the system further comprising:
at least one second sensor configured to sense at least one second parameter associated with one of the user or the beverage container, the at least one second sensor comprising one of an optical sensor or an inertial sensor;
a wearable device configured to be worn by the user, the wearable device comprising at least one third sensor, the at least one third sensor configured to sense at least one third parameter associated with one of the user or the wearable device and the at least one processor configured to determine an identity of a user handling the beverage container based on the at least one second parameter and the at least one third parameter.

15. The system of claim 1, further comprising at least one second sensor for sensing an amount of liquid within the beverage container, wherein the at least one processor is configured to track consumption of the liquid by the user based on the at least one second sensor.

16. The system of claim 15, wherein the at least one physiologic parameter comprises a complex impedance of skin of the user, and wherein the at least one processor is configured to assess hydration of the user based on the tracked consumption of the liquid by the user and the complex impedance.

17. A method for monitoring physiological parameters of a user, the method comprising:
receiving, by a processor, a signal from a capacitive sensor positioned on an exterior surface of a beverage container being held by a hand of the user, the signal indicative of capacitance measured by the capacitive sensor while a tissue of the hand is contacting the capacitive sensor;
processing, by the processor, the received signal to remove undesired elements from the received signal;
identifying, by the processor, a plurality of peaks in the processed signal; and
determining, by the processor, at least one physiological parameter of the user based on the identified peaks in the processed signal.

18. The method of claim 17, wherein the processing the received signal includes one or more of:
eliminating noise from the received signal;
removing a baseline from the received signal; or
filtering the received signal with a low pass filter.

19. The method of claim 17, wherein the determining at least one physiological parameter includes determining an inter-beat interval for the user.

20. The method of claim 17, further comprising digitizing the signal from the capacitive sensor.

21. The method of claim 17, further comprising performing signal differentiation on the processed signal to generate a differential signal.

22. The method of claim 21, wherein the identifying a plurality of peaks includes identifying positive and negative peaks in the differential signal.

23. A beverage container for monitoring physiological parameters of a user, the beverage container comprising:
a body having an exterior surface;
at least one capacitive sensor positioned on the exterior surface of the body such that a tissue of a hand of the user contacts the at least one capacitive sensor while the object beverage container is being held by a hand of the user, the at least one capacitive sensor configured to sense at least one parameter indicative of capacitance while the at least on capacitive sensor is in contact with the tissue;
at least one processor coupled to the body, the at least one processor configured to receive the at least one parameter from the at least one capacitive sensor and determine at least one physiological parameter of the user based on changes in capacitance in the received at least one parameter; and a communication interface coupled to the at least one processor, the communication interface configured to transmit the determined at least one physiological parameter to an electronic device accessible by a user.

24. A system for monitoring physiological parameters of a user, the system comprising:

an object to be held by a hand of the user:

at least one first sensor positioned on an exterior surface of the object to permit a tissue of a hand of a user to contact the at least one first sensor while the object is held by the hand of the user, the at least one first sensor configured to sense at least one first parameter indicative of capacitance while the at least one first sensor is in contact with the tissue;

at least one processor configured to calculate at least one physiological parameter of the user based on the at least one first parameter from the at least one first sensor, the at least one processor further configured to analyze changes in capacitance from the at least one first sensor to determine the at least one physiological parameter; and a wearable device configured to be worn by the user, the wearable device comprising at least one second sensor positioned to contact a tissue of the user when the wearable device is worn by the user, the at least one second sensor configured to sense at least one second parameter indicative of capacitance and the at least one processor configured to calculate at least one physiological parameter of the user based on the at least one second parameter from the at least one second sensor, wherein the at least one processor is configured to determine a blood pressure of a user in contact with the object based on the at least one first parameter from the at least one first sensor and the at least one second parameter from the at least one second sensor, wherein the at least one processor is configured to detect a first pulse wave based on the at least one first parameter from the at least one first sensor and detect a second pulse wave corresponding to the first pulse wave based on the at least one second parameter from the at least one second sensor, wherein the at least one processor is configured to determine a time delay between detection of the first pulse wave and the detection of the second pulse wave and to determine the blood pressure based on the time delay.

25. The system of claim 24, wherein the at least one first sensor is in contact with a finger of the user for detection of the first pulse wave.

26. The system of claim 25, wherein the object is a smartphone.

27. A method for monitoring physiological parameters of a user, the method comprising:

holding an object with a hand of the user such that a tissue of the hand contacts at least one first sensor positioned on an exterior surface of the object;

sensing, with the at least one first sensor, at least one first parameter indicative of capacitance while the at least one first sensor is in contact with the tissue;

calculating, with at least one processor, at least one physiological parameter of the user based on the at least one first parameter from the at least one first sensor;

analyzing, with the at least one processor, changes in capacitance from the at least one first sensor to determine the at least one physiological parameter;

wearing, by the user, a wearable device such that at least one second sensor of the wearable device contacts a tissue of the user;

sensing, with the at least one second sensor, at least one second parameter indicative of capacitance;

calculating, with the at least one processor, at least one physiological parameter of the user based on the at least one second parameter from the at least one second sensor;

determining, with the at least one processor, a blood pressure of a user in contact with the object based on the at least one first parameter from the at least one first sensor and the at least one second parameter from the at least one second sensor;

detecting, with the at least one processor, a first pulse wave based on the at least one first parameter from the at least one first sensor; and detecting, with the at least one processor, a second pulse wave corresponding to the first pulse wave based on the at least one second parameter from the at least one second sensor;

determining, with the at least one processor, a time delay between detection of the first pulse wave and the detection of the second pulse wave, wherein the determining the blood pressure is based on the time delay.

* * * * *